US012262892B2

(12) United States Patent
Smith et al.

(10) Patent No.: US 12,262,892 B2
(45) Date of Patent: *Apr. 1, 2025

(54) POWERED SURGICAL CUTTING AND STAPLING APPARATUS WITH MANUALLY RETRACTABLE FIRING SYSTEM

(71) Applicant: Cilag GmbH International, Zug (CH)

(72) Inventors: Bret W. Smith, Kings Mills, OH (US); Daniel J. Abbott, Maple Valley, WA (US); Richard F. Schwemberger, Cincinnati, OH (US); Frederick E. Shelton, IV, Hillsboro, OH (US); Chad P. Boudreaux, Cincinnati, OH (US); Brett E. Swensgard, West Chester, OH (US); Ryan J. Laurent, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/467,214

(22) Filed: Sep. 14, 2023

(65) Prior Publication Data
US 2024/0122598 A1    Apr. 18, 2024

Related U.S. Application Data

(63) Continuation of application No. 17/182,383, filed on Feb. 23, 2021, now Pat. No. 11,793,521, which is a
(Continued)

(51) Int. Cl.
*A61B 17/072* (2006.01)
*A61B 17/068* (2006.01)
(Continued)

(52) U.S. Cl.
CPC .......... *A61B 17/105* (2013.01); *A61B 17/068* (2013.01); *A61B 17/0686* (2013.01);
(Continued)

(58) Field of Classification Search
CPC .............. A61B 17/068; A61B 17/0686; A61B 17/072; A61B 17/07207; A61B 17/115;
(Continued)

(56) References Cited

U.S. PATENT DOCUMENTS 5,433,721 A * 7/1995 Hooven ............... A61B 17/068
606/139
5,465,895 A    11/1995 Knodel et al.
(Continued)

FOREIGN PATENT DOCUMENTS

EP     1621138 A2    2/2006
EP     2044890 A1    4/2009
(Continued)

OTHER PUBLICATIONS

Brazilian Examination Report dated Sep. 2, 2020 for Application No. BR PI0920403-2, 4 pgs.
(Continued)

*Primary Examiner* — Scott A Smith
(74) *Attorney, Agent, or Firm* — Frost Brown Todd LLP

(57) ABSTRACT

In one general aspect, various embodiments of the present invention can include a motorized surgical cutting and fastening instrument having a drive shaft, a motor selectively engageable with the drive shaft, and a manual return mechanism configured to operably disengage the motor from the drive shaft and retract the drive shaft. In at least one embodiment, a surgeon, or other operator of the surgical instrument, can utilize the manual return mechanism to retract the drive shaft after it has been advanced, especially when the motor, or a power source supplying the motor, has failed or is otherwise unable to provide a force sufficient to retract the drive shaft.

20 Claims, 63 Drawing Sheets

Related U.S. Application Data continuation of application No. 16/158,529, filed on Oct. 12, 2018, now Pat. No. 10,932,778, which is a continuation of application No. 15/054,751, filed on Feb. 26, 2016, now Pat. No. 10,149,683, which is a continuation of application No. 13/785,432, filed on Mar. 5, 2013, now Pat. No. 9,370,364, which is a continuation of application No. 12/249,117, filed on Oct. 10, 2008, now Pat. No. 8,608,045.

(51) Int. Cl.
*A61B 17/10* (2006.01)
*G16Z 99/00* (2019.01)
*A61B 17/00* (2006.01)
*A61B 17/29* (2006.01)
*A61B 17/32* (2006.01)

(52) U.S. Cl.
CPC ........ *A61B 17/07207* (2013.01); *A61B 17/10* (2013.01); *G16Z 99/00* (2019.02); *A61B 2017/00398* (2013.01); *A61B 2017/00734* (2013.01); *A61B 17/072* (2013.01); *A61B 2017/07214* (2013.01); *A61B 2017/2923* (2013.01); *A61B 2017/2927* (2013.01); *A61B 2017/2946* (2013.01); *A61B 2017/320052* (2013.01)

(58) Field of Classification Search
CPC .... A61B 17/00234; A61B 2017/00017; A61B 2017/00734; A61B 2017/00398; A61B 2017/07214; A61B 2017/2923; A61B 2017/2927; A61B 2017/2946; A61B 2017/320052
USPC .............. 227/19, 175.1, 176.1, 175.2, 180.1; 606/1, 139, 153, 219
See application file for complete search history.

(56) References Cited

U.S. PATENT DOCUMENTS

| | | | |
|---|---|---|---|
| 5,653,374 A * | 8/1997 | Young | A61B 17/07207 227/176.1 |
| 5,688,270 A | 11/1997 | Yates et al. | |
| 5,709,680 A | 1/1998 | Yates et al. | |
| 5,954,259 A * | 9/1999 | Viola | A61B 17/07207 227/176.1 |
| 6,905,057 B2 | 6/2005 | Swayze et al. | |
| 6,978,921 B2 | 12/2005 | Shelton, IV et al. | |
| 7,044,353 B2 * | 5/2006 | Mastri | A61B 17/07207 227/176.1 |
| 7,364,061 B2 | 4/2008 | Swayze et al. | |
| 7,422,136 B1 * | 9/2008 | Marczyk | A61B 17/07207 227/176.1 |
| 7,448,525 B2 | 11/2008 | Shelton, IV et al. | |
| 7,464,846 B2 * | 12/2008 | Shelton, IV | A61B 17/07207 227/19 |
| 7,464,849 B2 | 12/2008 | Shelton, IV et al. | |
| 7,588,175 B2 * | 9/2009 | Timm | A61B 17/07207 227/19 |
| 7,607,557 B2 | 10/2009 | Shelton, IV et al. | |
| 7,670,334 B2 | 3/2010 | Hueil et al. | |
| 7,673,783 B2 | 3/2010 | Morgan et al. | |
| 7,766,210 B2 | 8/2010 | Shelton, IV et al. | |
| 7,959,050 B2 * | 6/2011 | Smith | A61B 17/115 227/176.1 |
| 8,006,885 B2 * | 8/2011 | Marczyk | A61B 17/07207 227/176.1 |
| 8,210,411 B2 | 7/2012 | Yates et al. | |
| 8,608,045 B2 | 12/2013 | Smith et al. | |
| 9,370,364 B2 | 6/2016 | Smith et al. | |
| 10,149,683 B2 | 12/2018 | Smith et al. | |
| 10,932,778 B2 | 3/2021 | Smith et al. | |
| 11,291,443 B2 | 4/2022 | Viola et al. | |
| 11,413,041 B2 | 8/2022 | Viola et al. | |
| 11,793,521 B2 | 10/2023 | Shelton, IV et al. | |
| 2008/0245842 A1 | 10/2008 | Marczyk | |

FOREIGN PATENT DOCUMENTS

| | | |
|---|---|---|
| JP | H09-164144 A | 6/1997 |
| JP | 2001-515401 A | 9/2001 |
| JP | 2005-103279 A | 4/2005 |
| JP | 2006-015150 A | 1/2006 |
| JP | 2006-218296 A | 8/2006 |
| JP | 2008-036424 A | 2/2008 |
| WO | WO 2009/046394 A1 | 4/2009 |

OTHER PUBLICATIONS

Chinese Office Action, The First Office Action, dated Jan. 11, 2013 for Application No. CN 200980139932.1, 5 pgs.
European Examination Report dated Jun. 6, 2017 for Application No. EP 09806214.4, 4 pgs.
International Search Report and Written Opinion dated Apr. 26, 2010 for Application No. PCT/US2009/060109, 11 pgs.
Japanese Search Report by Registered Search Organization dated Aug. 7, 2013 for Application No. JP 2011-531197, 10 pgs.
Japanese Office Action, Decision to Grant a Patent, dated Aug. 13, 2013 for Application No. JP 2011-531197, 2 pgs.

* cited by examiner

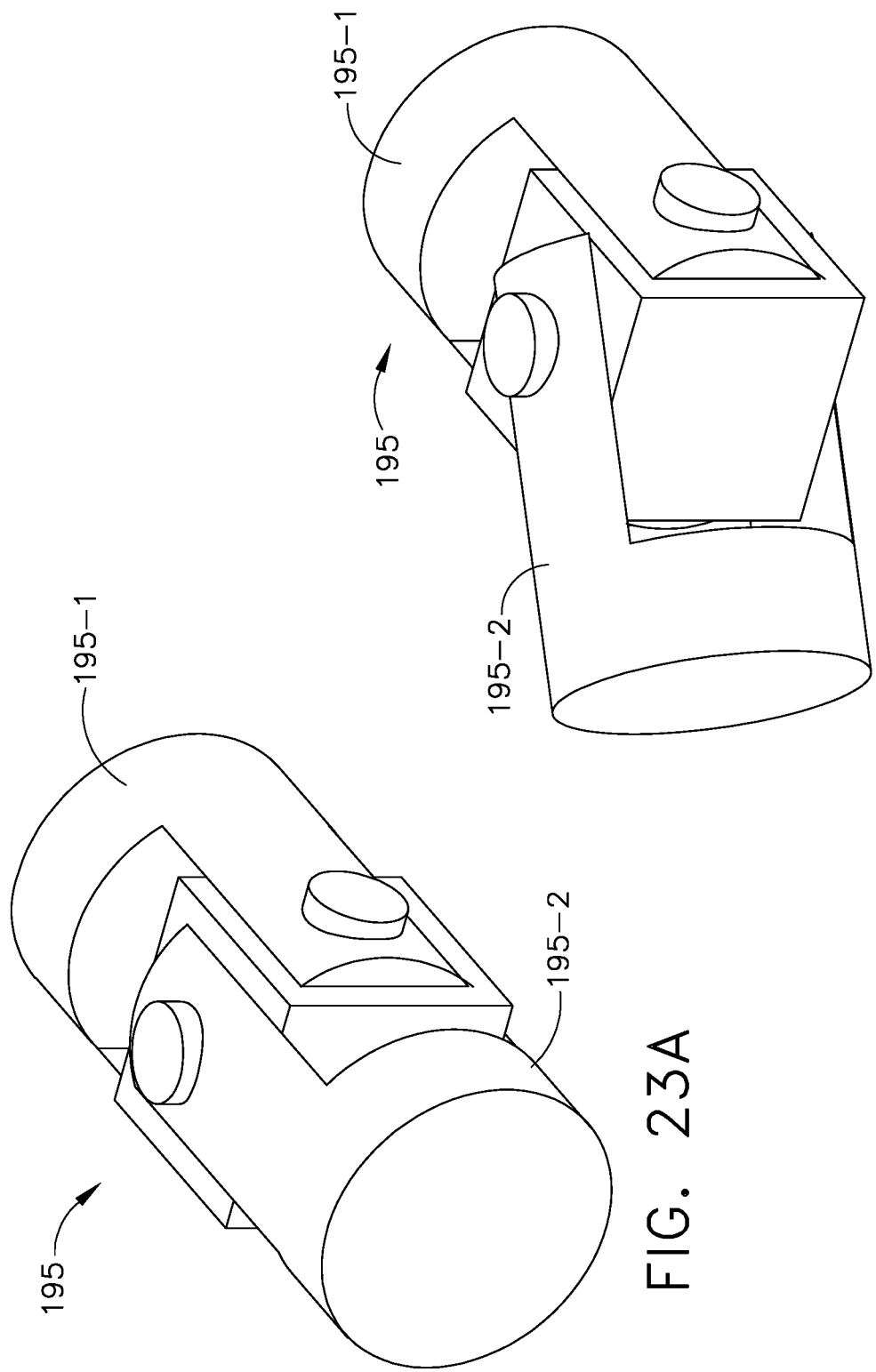

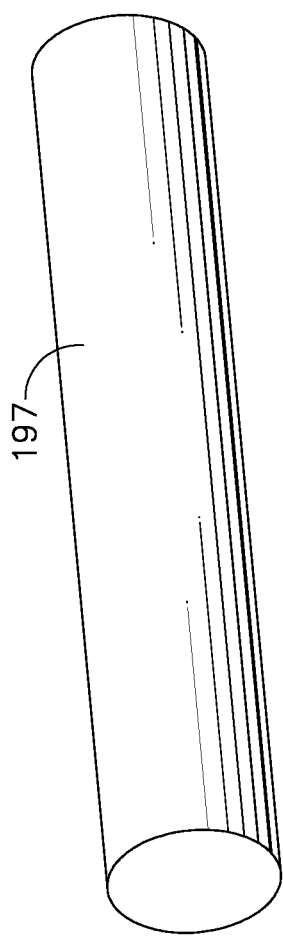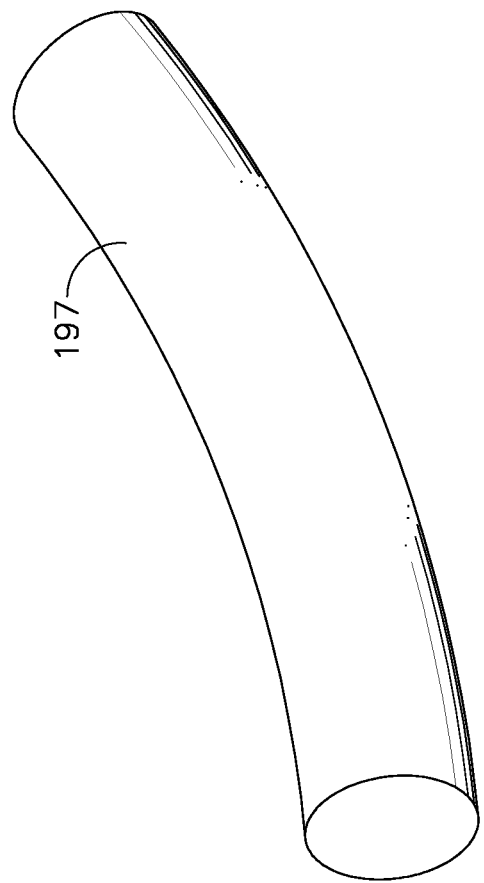
FIG. 24A
FIG. 24B

POWERED SURGICAL CUTTING AND STAPLING APPARATUS WITH MANUALLY RETRACTABLE FIRING SYSTEM

CROSS-REFERENCE TO RELATED APPLICATIONS

This application is a continuation application claiming priority under 35 U.S.C. § 120 to U.S. patent application Ser. No. 17/182,383, entitled POWERED SURGICAL CUTTING AND STAPLING APPARATUS WITH MANUALLY RETRACTABLE FIRING SYSTEM, filed Feb. 23, 2021, issued as U.S. Pat. No. 11,793,521 on Oct. 24, 2023, which is a continuation application claiming priority under 35 U.S.C. § 120 to U.S. patent application Ser. No. 16/158,529, entitled POWERED SURGICAL CUTTING AND STAPLING APPARATUS WITH MANUALLY RETRACTABLE FIRING SYSTEM, filed Oct. 12, 2018, issued as U.S. Pat. No. 10,932,778 on Mar. 2, 2021, which is a continuation application claiming priority under 35 U.S.C. § 120 to U.S. patent application Ser. No. 15/054,751, entitled POWERED SURGICAL CUTTING AND STAPLING APPARATUS WITH MANUALLY RETRACTABLE FIRING SYSTEM, filed Feb. 26, 2016, which issued on Dec. 11, 2018 as U.S. Pat. No. 10,149,683, which is a continuation application claiming priority under 35 U.S.C. § 120 to U.S. patent application Ser. No. 13/785,432, entitled POWERED SURGICAL CUTTING AND STAPLING APPARATUS WITH MANUALLY RETRACTABLE FIRING SYSTEM, filed Mar. 5, 2013, which issued on Jun. 21, 2016 as U.S. Pat. No. 9,370,364, which is a continuation application claiming priority under 35 U.S.C. § 120 to U.S. patent application Ser. No. 12/249,117, entitled POWERED SURGICAL CUTTING AND STAPLING APPARATUS WITH MANUALLY RETRACTABLE FIRING SYSTEM, filed on Oct. 10, 2008, which issued on Dec. 17, 2013 as U.S. Pat. No. 8,608,045, the entire disclosures of which are hereby incorporated by reference herein.

BACKGROUND

1. Field of the Invention

The present invention generally concerns surgical cutting and fastening instruments and, more particularly, motor-driven surgical cutting and fastening instruments.

2. Description of the Related Art

Endoscopic surgical instruments are often preferred over traditional open surgical devices since a smaller incision, or incisions, associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of movable wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, the disclosure of which is hereby incorporated by reference in its entirety, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, or multiple firing strokes, depending on the device. Firing the surgical stapler causes severing and stapling of the tissue. The simultaneous severing and stapling avoids complications that may arise when performing such actions sequentially with different surgical tools that respectively only sever or staple.

SUMMARY

In one general aspect, various embodiments of the present invention can include a motorized surgical cutting and fastening instrument having a drive shaft, a motor selectively engageable with the drive shaft, and a manual return mechanism configured to retract the drive shaft and operably disengage the motor from the drive shaft. In at least one embodiment, a surgeon, or other operator of the surgical instrument, can utilize the manual return mechanism to retract the drive shaft after it has been advanced, especially when the motor, or a power source supplying the motor, has failed or is otherwise unable to provide a force sufficient to retract the drive shaft. In various embodiments, the operation of the manual return mechanism can operably disconnect the motor from the drive shaft via mechanical, electrical, electronic, and/or electro-mechanical arrangements, for example.

In at least one embodiment, the instrument can include an end effector comprising a movable cutting member for cutting an object positioned in the end effector, wherein the drive shaft can be operably coupled with the cutting member and can be movable between a proximal position and a distal position. In at least one such embodiment, the drive shaft can include a plurality of first drive teeth and a plurality of second drive teeth, wherein the instrument can further include a pinion gear selectively engageable with the plurality of first drive teeth, a motor configured to rotate the pinion gear, and a firing trigger configured such that the operation of the firing trigger actuates the motor.

In at least one embodiment, the instrument can further include a pivot, a lever rotatable about the pivot in a first direction and a second direction, a cam, wherein the lever is configured to move the cam between a first position and a second position, and a pinion spring configured to bias the pinion gear into operative engagement with the drive shaft when the cam is in its first position. In various embodiments, the cam can be configured to engage the pinion gear when the cam is moved from its first position to its second position and move the pinion gear away from the drive shaft such that the pinion gear is operably disengaged from the plurality of first drive teeth.

In at least one embodiment, the instrument can further include a pawl rotatably mounted to the lever and a pawl spring operably engaged with the pawl, wherein the pawl spring can be configured to move the pawl between a disengaged position in which the pawl is operably disengaged from the plurality of second drive teeth and an engaged position in which the pawl is operably engaged with the plurality of second drive teeth. In various embodiments, the pawl spring can move the pawl between its disengaged and engaged positions when the cam is moved from its first position to its second position. Once the pawl is in its engaged position, the pawl can be configured to move the drive shaft from its distal position toward its proximal position when the lever is rotated in the first direction. The pawl can also be configured to slide over the plurality of second teeth when the lever is rotated in the second direction.

This Summary is intended be briefly outline certain embodiments of the subject application. It should be understood that the subject application is not limited to the embodiments disclosed in this Summary, and is intended to cover modifications that are within its spirit and scope, as defined by the claims. It should be further understood that this Summary should not be read or construed in a manner that will act to narrow the scope of the claims.

BRIEF DESCRIPTION OF THE FIGURES

Various embodiments of the present invention are described herein by way of example in conjunction with the following figures, wherein

FIGS. 23A-B show a universal joint ("u-joint") that may be employed at the articulation point of the instrument;

FIGS. 24A-B shows a torsion cable that may be employed at the articulation point of the instrument;

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Figure 1:
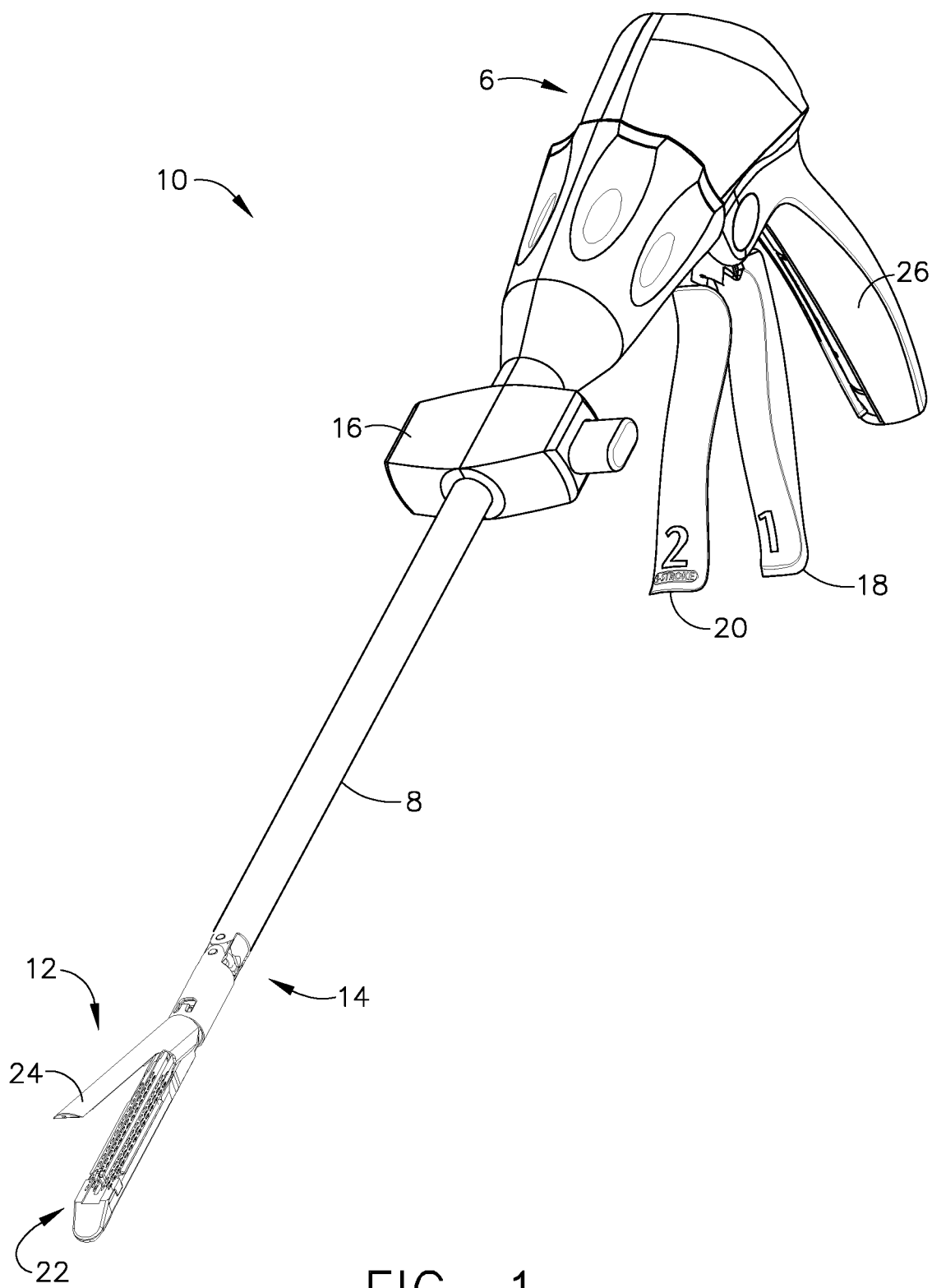
FIGS. 1 and 2 are perspective views of a surgical cutting and fastening instrument.

Preferred embodiments of the presently disclosed endoscopic surgical stapling apparatus will now be described in detail with reference to the drawings, in which like reference numerals designate identical or corresponding elements in each of the several views. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 2:
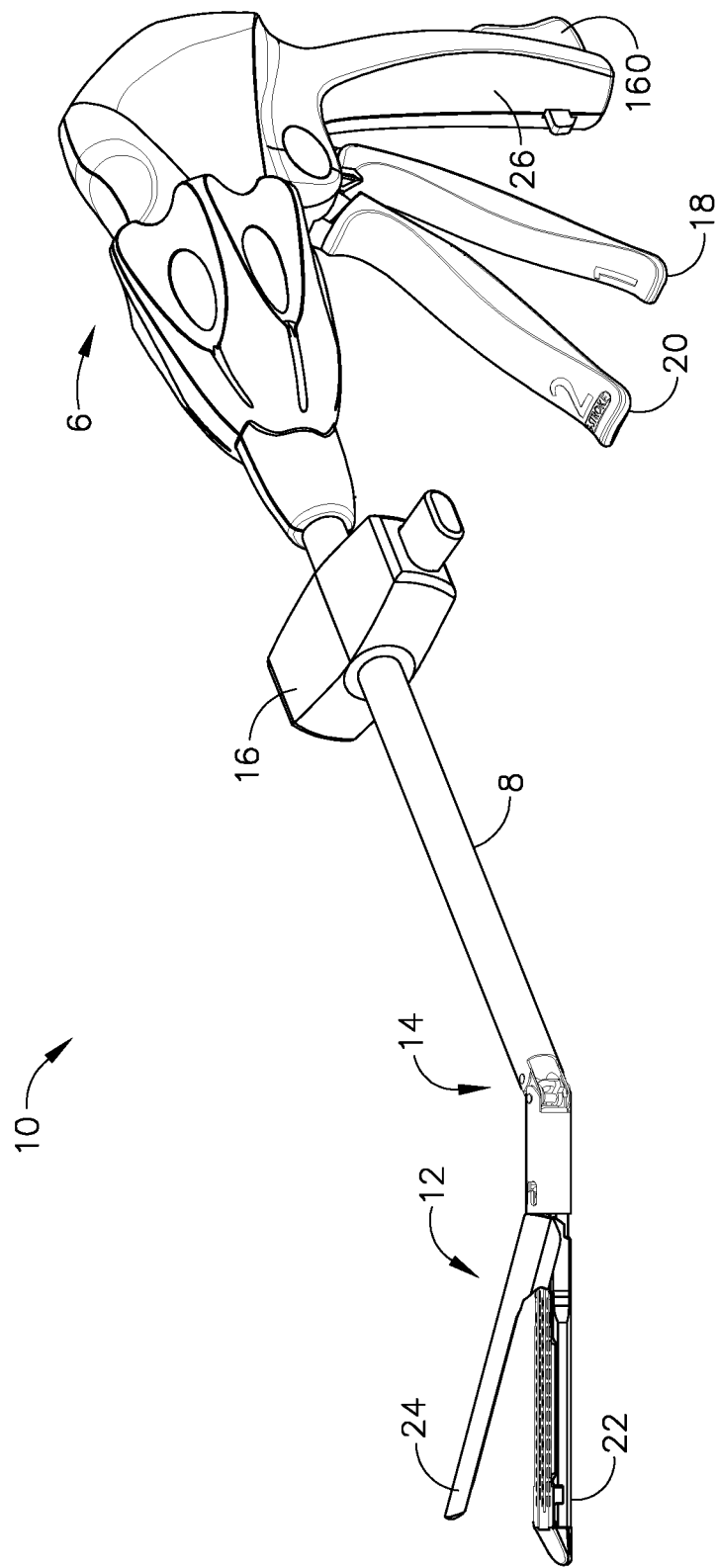

FIGS. 1 and 2 depict a surgical cutting and fastening instrument 10. The illustrated embodiment is an endoscopic instrument and, in general, the embodiments of the instrument 10 described herein are endoscopic surgical cutting and fastening instruments. It should be noted, however, that according to various embodiments of the present invention, the instrument may be a non-endoscopic surgical cutting and fastening instrument, such as a laparoscopic instrument, for example. Various surgical instruments are disclosed in U.S. patent application Ser. No. 10/674,026, entitled SURGICAL STAPLING INSTRUMENT INCORPORATING A MULTISTROKE FIRING POSITION INDICATOR WITH RETRACTION MECHANISM, filed on Sep. 29, 2003, now U.S. Pat. No. 7,364,061; U.S. patent application Ser. No. 11/343,498, entitled MOTOR-DRIVEN SURGICAL CUTTING AND FASTENING INSTRUMENT WITH USER FEEDBACK SYSTEM, filed on Jan. 31, 2006, now U.S. Pat. No. 7,766,210; and U.S. patent application Ser. No. 11/497,936, entitled PNEUMATICALLY POWERED SURGICAL CUTTING AND FASTENING INSTRUMENT WITH MANUALLY OPERATED RETRACTION APPARATUS, filed on Aug. 2, 2006, now U.S. Pat. No. 7,448,525, the entire disclosures of which are incorporated herein by reference.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in U.S. patent application Ser. No. 11/329,020, filed Jan. 10, 2006, entitled SURGICAL INSTRUMENT HAVING AN ARTICULATING END EFFECTOR, now U.S. Pat. No. 7,670,334, the entire disclosure of which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, as a slide release button 160 shown in FIG. 14, and/or button 172 shown in FIG. 16.

Figure 3:
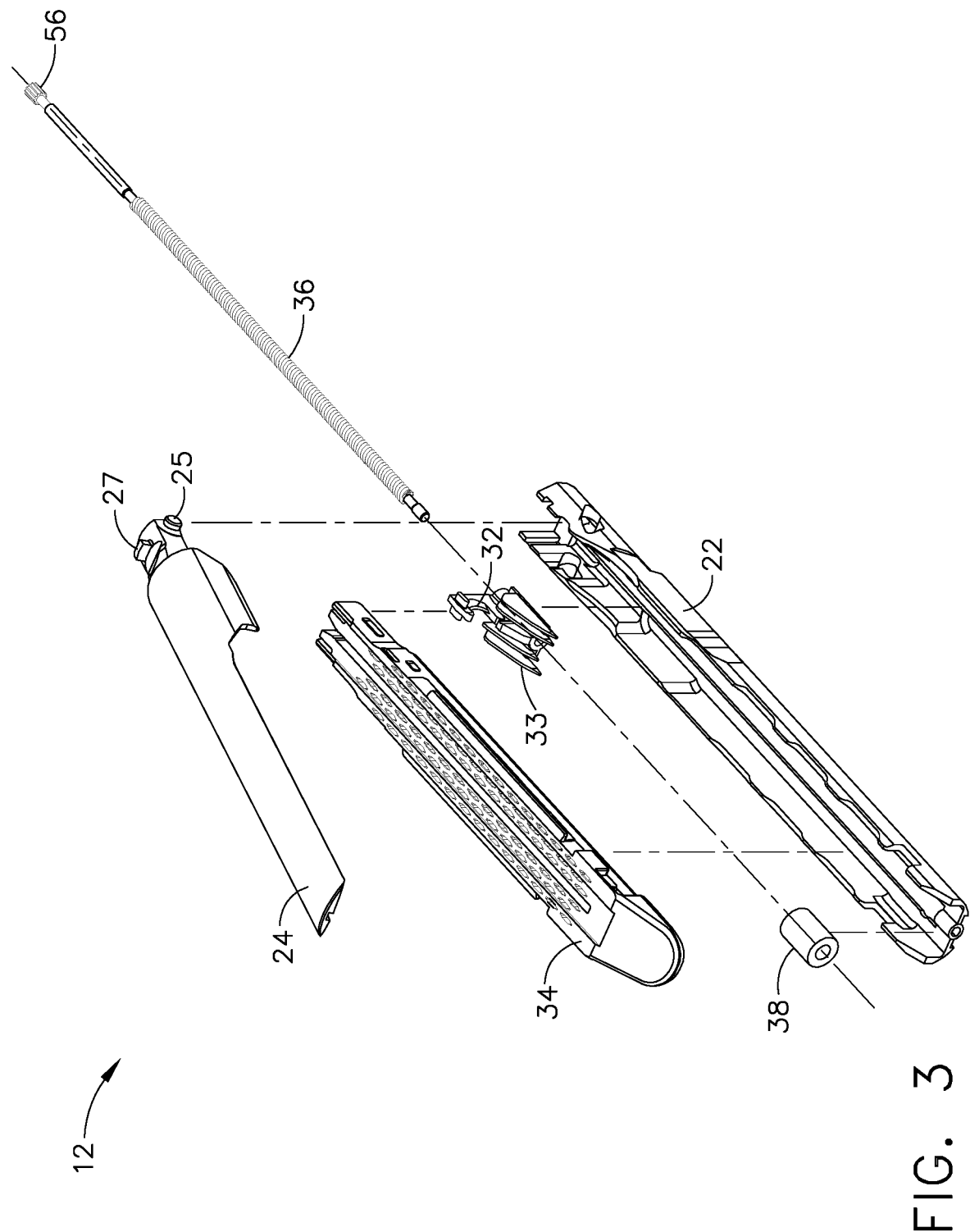
FIGS. 3-5 are exploded views of an end effector and shaft of the instrument of FIG. 1.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled SURGICAL STAPLING INSTRUMENT INCORPORATING AN E-BEAM FIRING MECHANISM, filed on May 20, 2003, the entire disclosure of which is incorporated herein by reference, provides more details about such two-stroke cutting and fastening instruments. The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled ELECTROSURGICAL HEMOSTATIC DEVICE, filed on Dec. 22, 1994; and U.S. Pat. No. 5,688,270 entitled ELECTROSURGICAL HEMOSTATIC DEVICE WITH RECESSED AND/OR OFFSET ELECTRODES, filed on Jan. 18, 1995, the entire disclosures of which are incorporated herein by reference, disclose an endoscopic cutting instrument that uses RF energy to seal the severed tissue. U.S. patent application Ser. No. 11/267,811 entitled SURGICAL STAPLING INSTRUMENTS STRUCTURED FOR DELIVERY OF MEDICAL AGENTS, filed on Nov. 4, 2005, now U.S. Pat. No. 7,673,783; and U.S. patent application Ser. No. 11/267,383 entitled SURGICAL STAPLING INSTRUMENTS STRUCTURED FOR PUMP-ASSISTED DELIVERY OF MEDICAL AGENTS, filed on Nov. 4, 2005, now U.S. Pat. No. 7,607,557, the entire disclosures of which are also incorporated herein by reference, disclose an endoscopic cutting instrument that uses adhesives to fasten the severed tissue. Accordingly, although the description herein refers to cutting/stapling operations and the like below, it should be recognized that this is an exemplary embodiment and is not meant to be limiting. Other tissue-fastening techniques may also be used.

Figure 4:
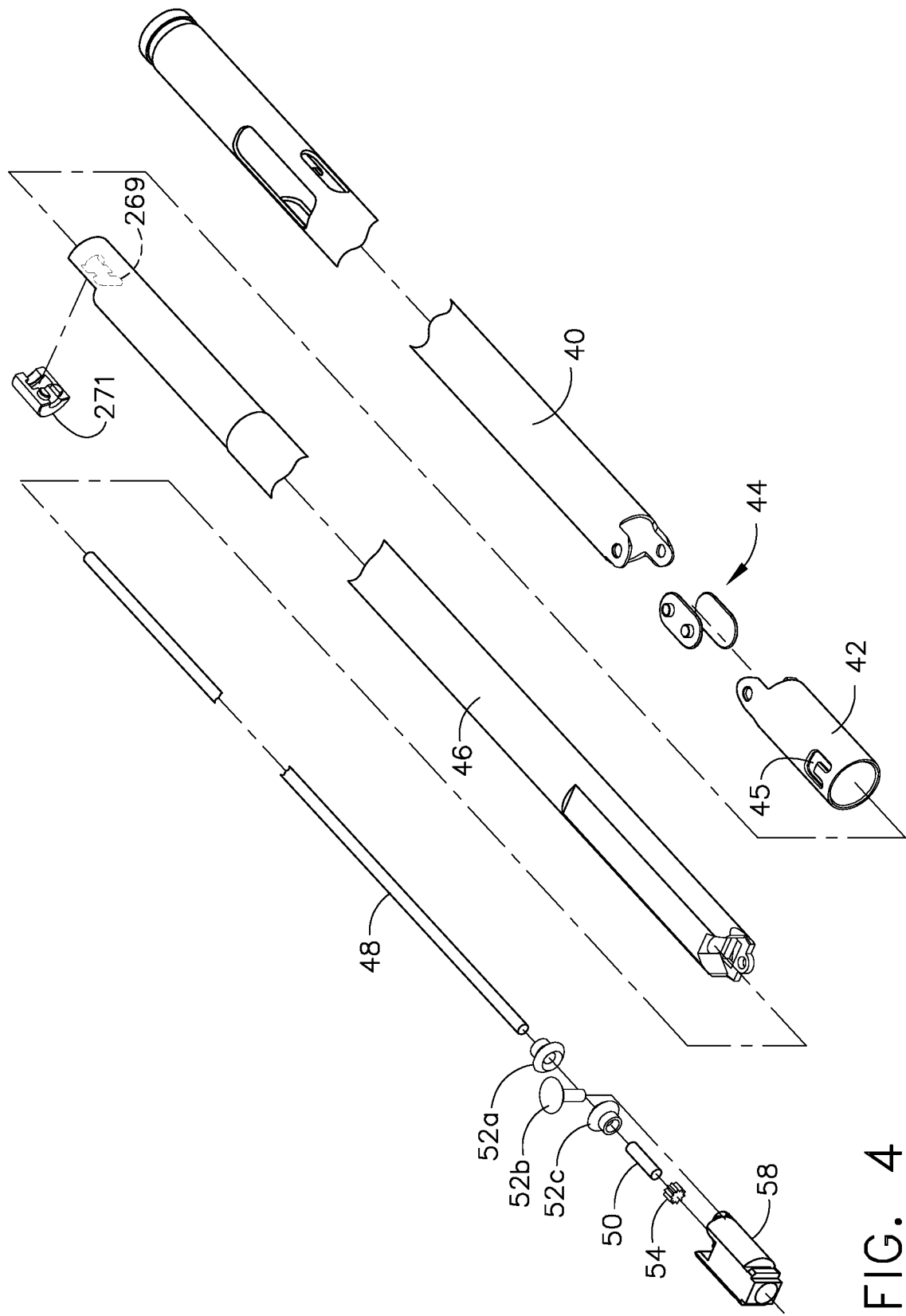
Figure 5:
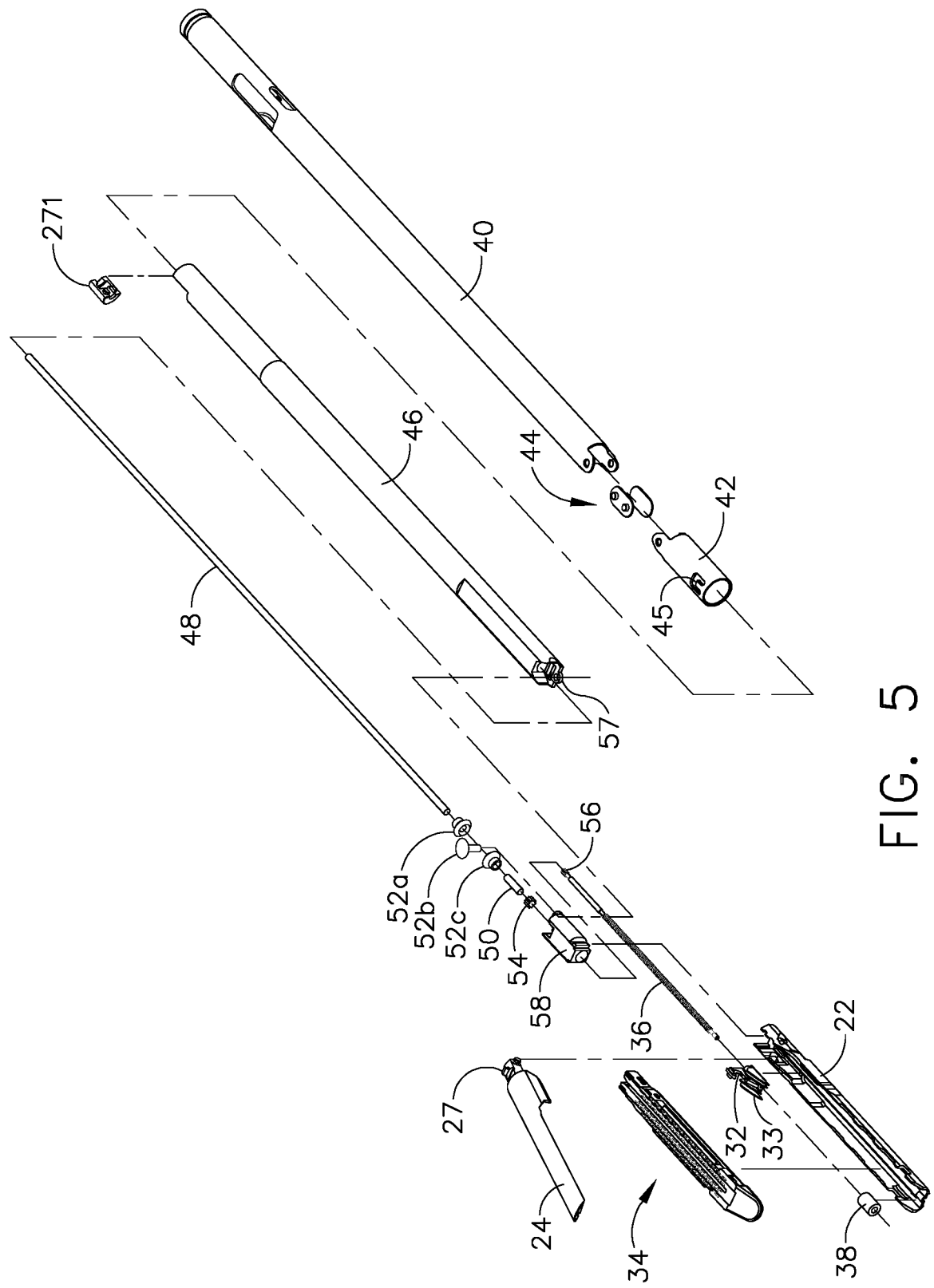
Figure 6:
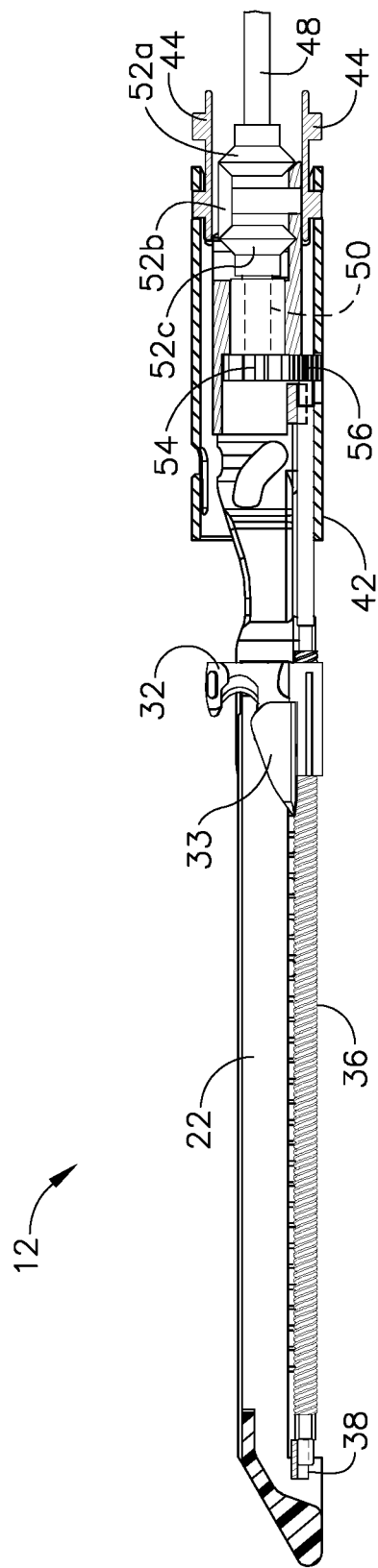
FIG. 6 is a side view of the end effector according of FIG. 3.
Figure 7:
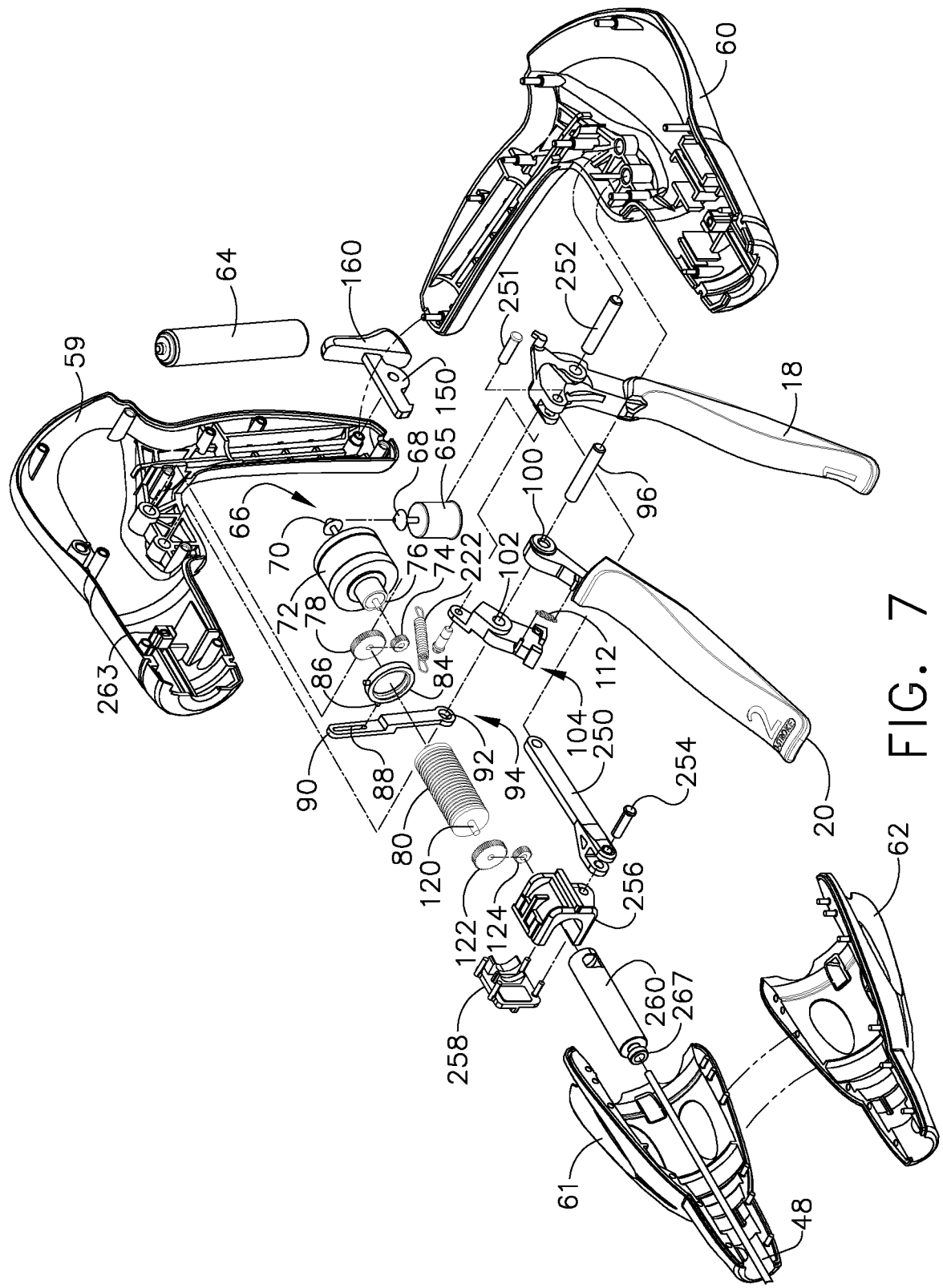
FIG. 7 is an exploded view of the handle of the instrument of FIG. 1.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52*b* may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52*a-c*) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52*a-c* causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector. The sled 33 may be made of, for example, plastic, and may have a sloped distal surface. As the sled 33 traverse the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

FIGS. 7-10 illustrate an exemplary embodiment of a motor-driven endocutter, and in particular the handle thereof, that provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. In some embodiments, the battery may comprise a LiMnO2 and/or NiCd battery, for example. In certain embodiments, the battery may be external to pistol grip portion 26 and/or the surgical instrument altogether, for example. The battery 64 powers a motor 65 disposed in an upper portion of the pistol grip portion 26 of the handle 6. According to various embodiments, the motor 65 may be a DC brushed driving motor having a maximum rotation of, approximately, 5000 RPM, for example. In certain embodiments, the rotation can be approximately 20000 RPM, for example, less than 20000, greater 20000, and/or suitable speed for the required load and/or operational parameters. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat, variable resistor, and/or limit switch. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65 at, for example, a rate proportional to how hard the operator pulls back the firing trigger 20. The forward rotation of the motor 65 in turn causes the gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
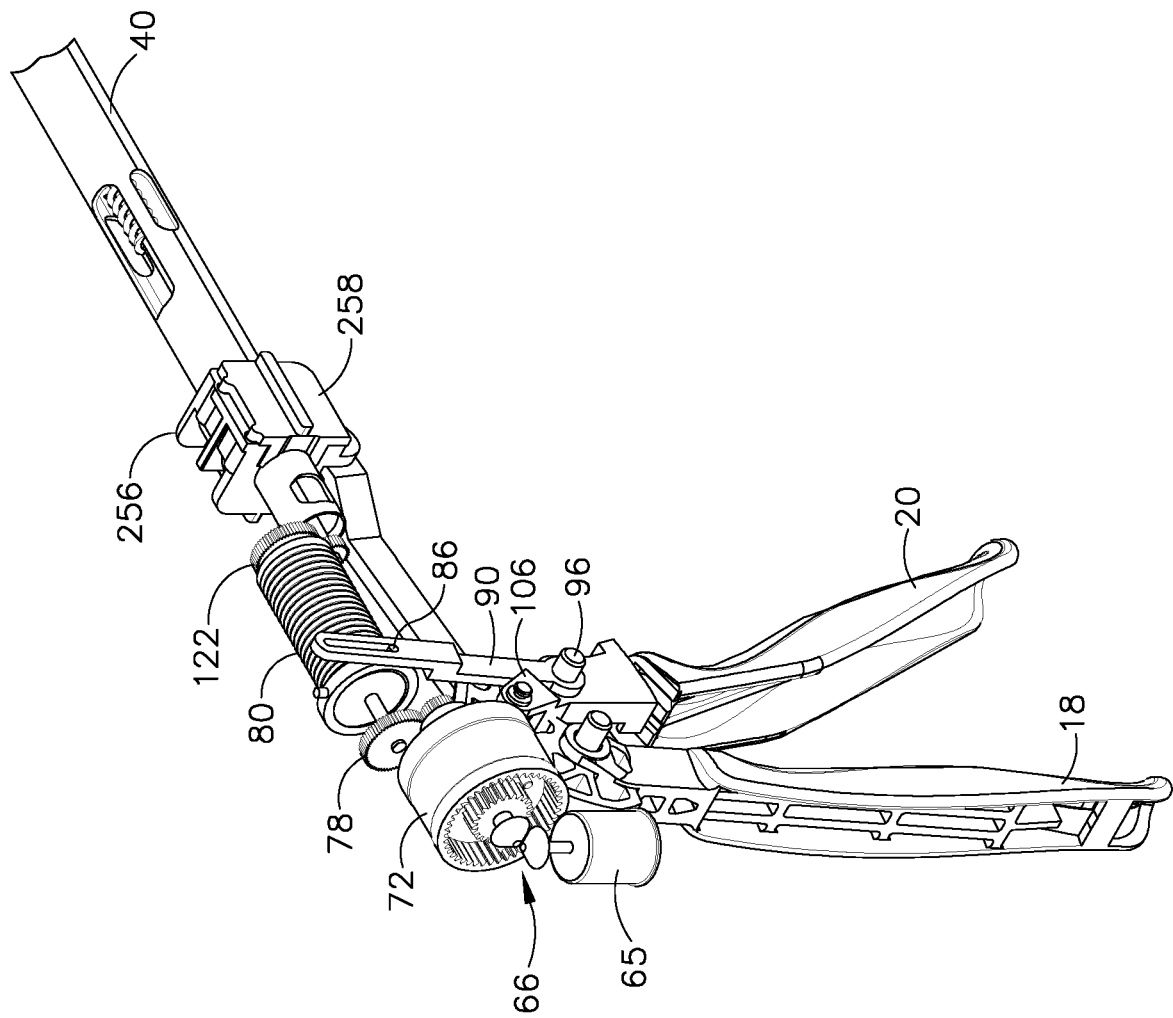
FIGS. 8 and 9 are partial perspective views of the handle of FIG. 7.
Figure 9:
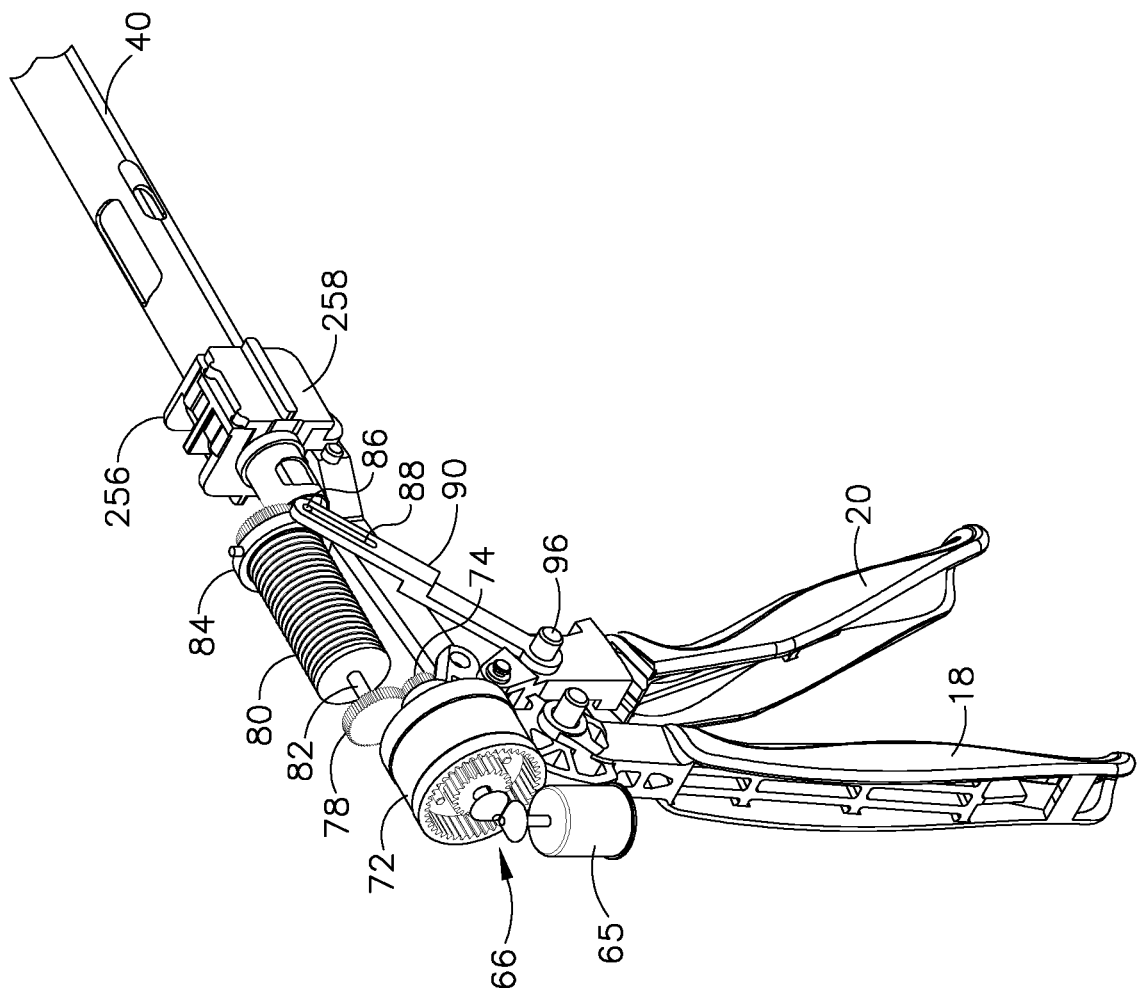
Figure 10:
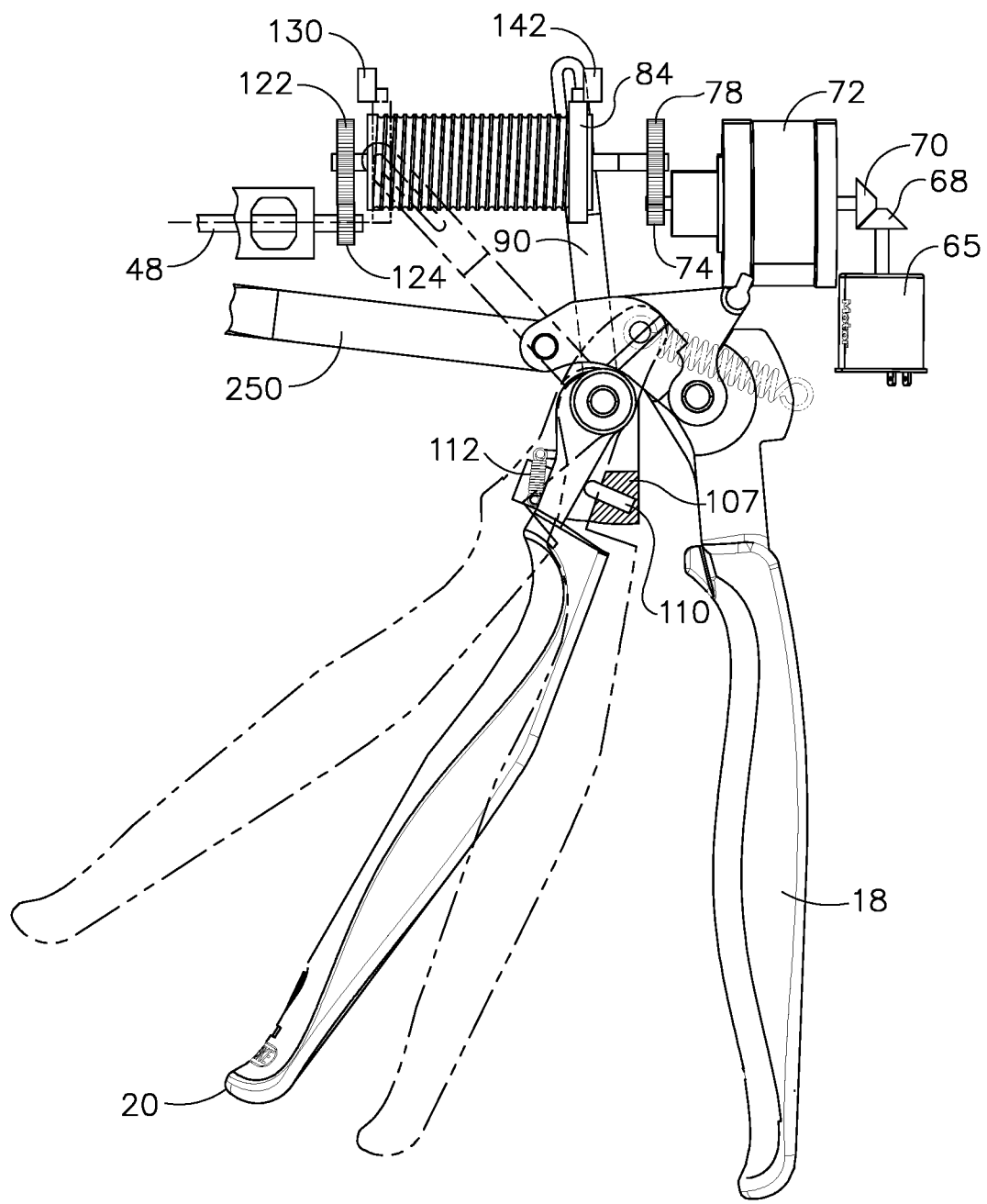
FIG. 10 is a side view of the handle of FIG. 7.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Figure 41:
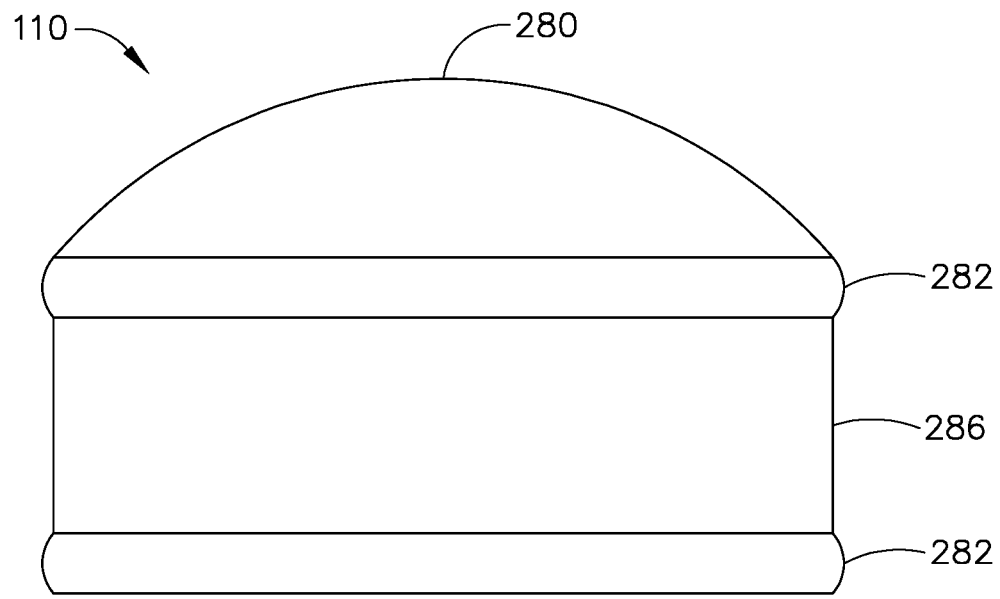
FIGS. 41-42 illustrate a proportional sensor that may be used according to various embodiments.
Figure 42:
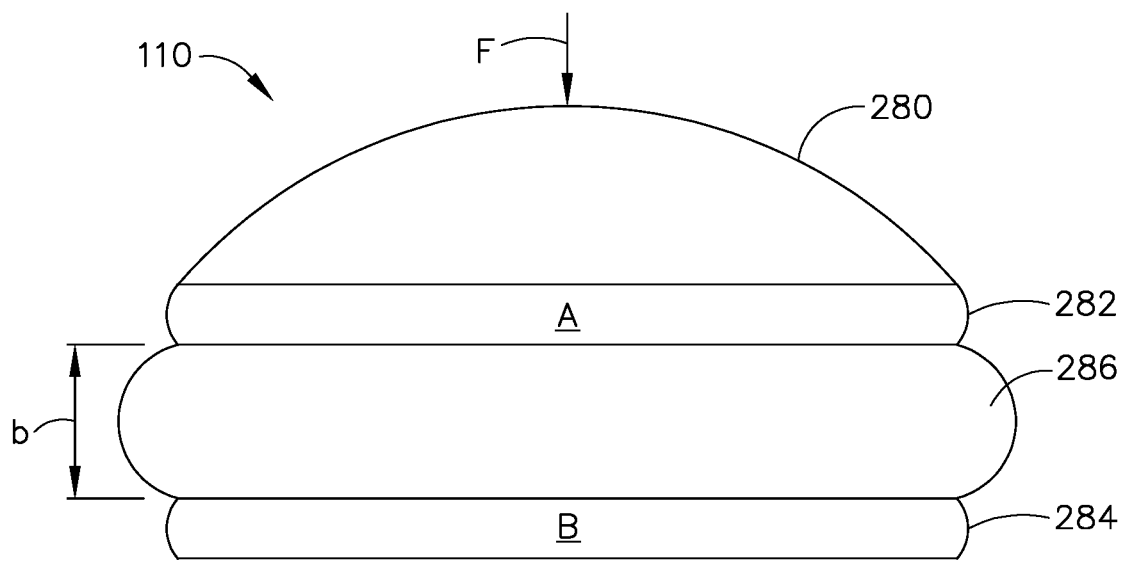

FIGS. 41 and 42 illustrate two states of a variable sensor that may be used as the run motor sensor 110. The sensor 110 may include a face portion 280, a first electrode (A) 282, a second electrode (B) 284, and a compressible dielectric material 286 (e.g., EAP) between the electrodes 282, 284. The sensor 110 may be positioned such that the face portion 280 contacts the firing trigger 20 when retracted. Accordingly, when the firing trigger 20 is retracted, the dielectric material 286 is compressed, as shown in FIG. 42, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric 286 is compressed due to retraction of the firing trigger 20 (denoted as force "F" in FIG. 42) is proportional to the impedance between the electrodes 282, 284, which can be used to proportionally control the motor 65.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
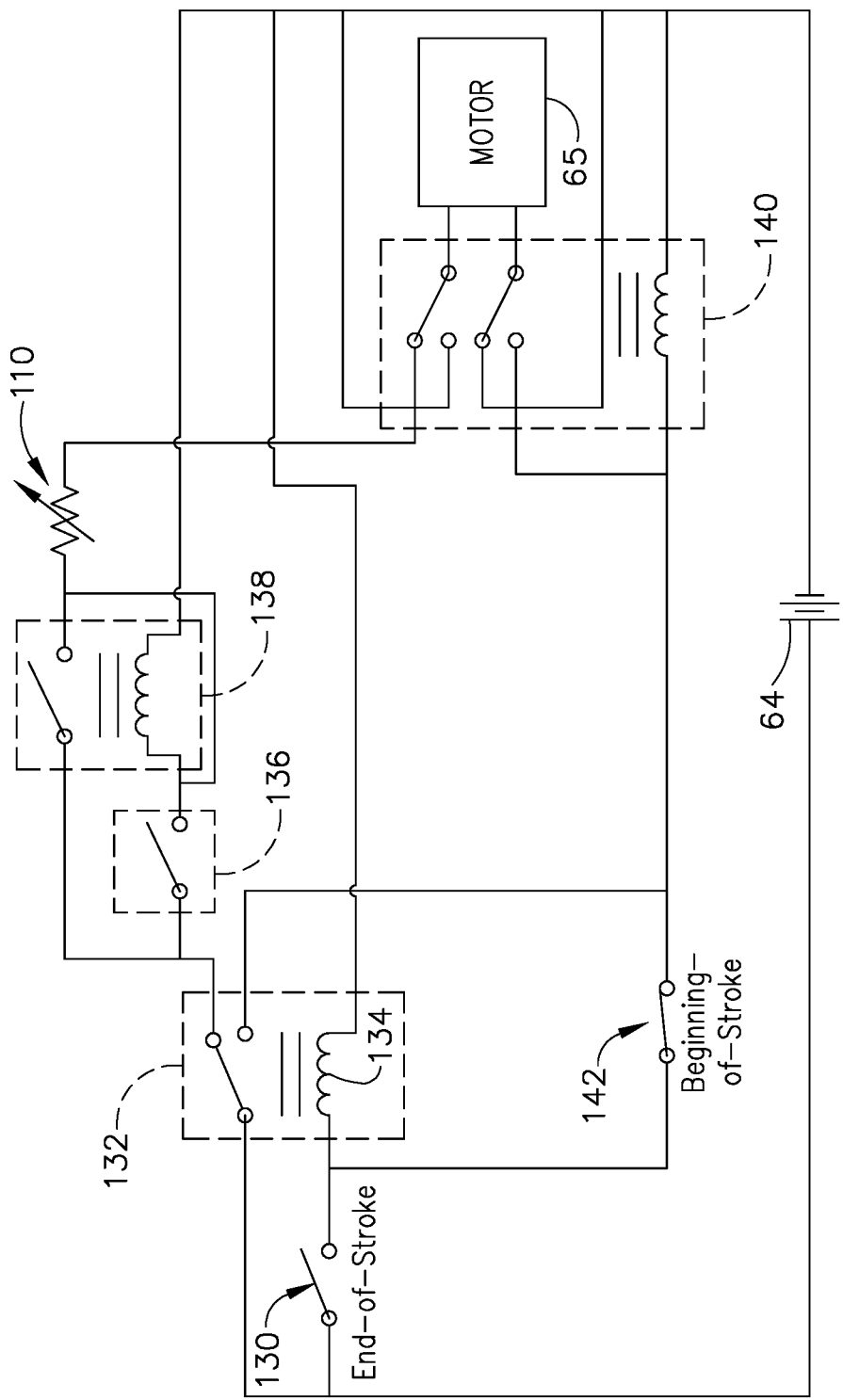
FIG. 11 is a schematic diagram of a circuit used in the instrument according to various embodiments.

FIG. 11 is a schematic diagram of an electrical circuit of the instrument 10. When an operator initially pulls in the firing trigger 20 after locking the closure trigger 18, the sensor 110 is activated, allowing current to flow there through. If the normally-open reverse motor sensor switch 130 is open (meaning the end of the end effector stroke has not been reached), current may flow to a single pole, double throw relay 132. Since the reverse motor sensor switch 130 is not closed, the inductor 134 of the relay 132 may not be energized, so the relay 132 will be in its non-energized state. In certain embodiments, current may be reversed via a switch, such as a single pole, double throw switch, for example. In at least one embodiment, the motor may be reversed without the use of a relay at all. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 134. This causes the relay 134 to assume its energized state (not shown in FIG. 13), which causes current to bypass the cartridge lockout sensor 136 and variable resistor 110, and instead causes current to flow to both the normally-closed double pole, double throw relay 142 and back to the motor 65, but in a manner, via the relay 140, that causes the motor 65 to reverse its rotational direction.

Because the stop motor sensor switch 142 is normally-closed, current will flow back to the relay 134 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 12:
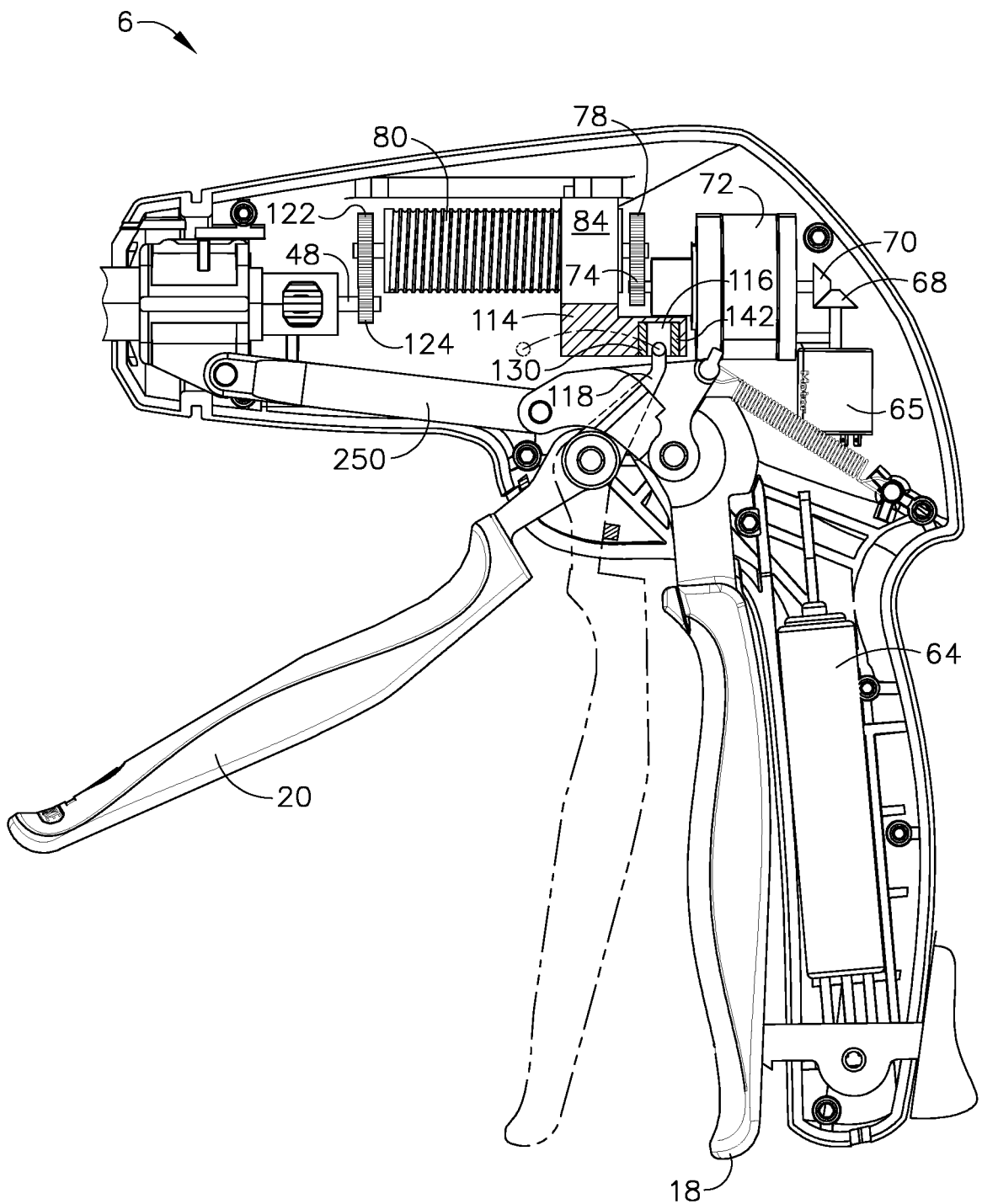
FIGS. 12-13 are side views of the handle according to other embodiments.

FIG. 12 is a side-view of the handle 6 of a power-assist motorized endocutter according to another embodiment. The embodiment of FIG. 12 is similar to that of FIGS. 7-10 except that in the embodiment of FIG. 12, there is not a slotted arm connected to the ring 84 threaded on the helical gear drum 80. Instead, in the embodiment of FIG. 12, the ring 84 includes a sensor portion 114 that moves with the ring 84 as the ring 84 advances down (and back) on the helical gear drum 80. The sensor portion 114 includes a notch 116. The reverse motor sensor 130 may be located at the distal end of the notch 116 and the stop motor sensor 142 may be located at the proximate end of the notch 116. As the ring 84 moves down the helical gear drum 80 (and back), the sensor portion 114 moves with it. Further, as shown in FIG. 12, the middle piece 104 may have an arm 118 that extends into the notch 12.

In operation, as an operator of the instrument 10 retracts in the firing trigger 20 toward the pistol grip 26, the run motor sensor 110 detects the motion and sends a signal to power the motor 65, which causes, among other things, the helical gear drum 80 to rotate. As the helical gear drum 80 rotates, the ring 84 threaded on the helical gear drum 80 advances (or retracts, depending on the rotation). Also, due to the pulling in of the firing trigger 20, the middle piece 104 is caused to rotate CCW with the firing trigger 20 due to the forward motion stop 107 that engages the firing trigger 20. The CCW rotation of the middle piece 104 cause the arm 118 to rotate CCW with the sensor portion 114 of the ring 84 such that the arm 118 stays disposed in the notch 116. When the ring 84 reaches the distal end of the helical gear drum 80, the arm 118 will contact and thereby trip the reverse motor sensor 130. Similarly, when the ring 84 reaches the proximate end of the helical gear drum 80, the arm will contact and thereby trip the stop motor sensor 142. Such actions may reverse and stop the motor 65, respectively, as described above.

Figure 13:
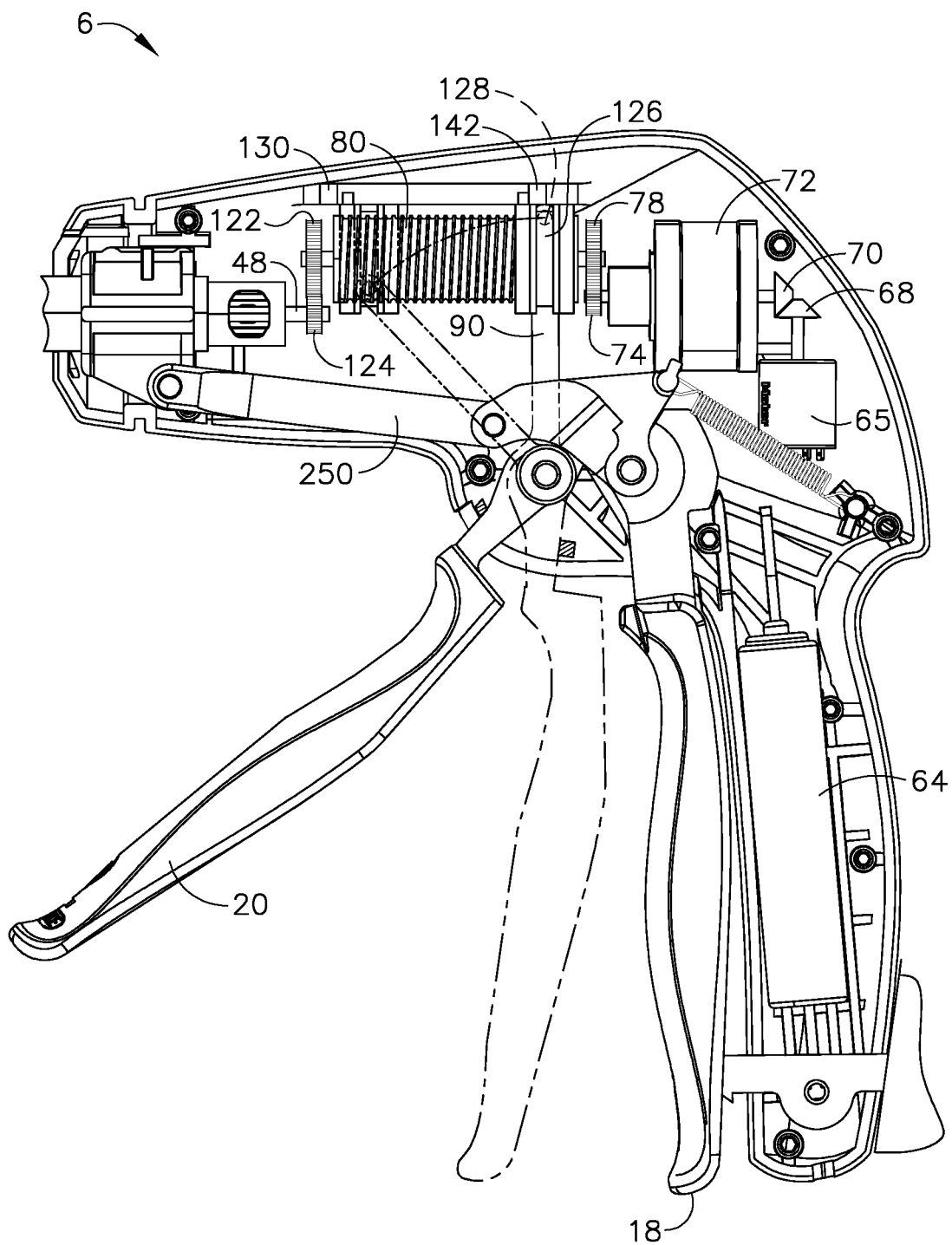

FIG. 13 is a side-view of the handle 6 of a power-assist motorized endocutter according to another embodiment. The embodiment of FIG. 13 is similar to that of FIGS. 7-10 except that in the embodiment of FIG. 13, there is no slot in the arm 90. Instead, the ring 84 threaded on the helical gear drum 80 includes a vertical channel 126. Instead of a slot, the arm 90 includes a post 128 that is disposed in the channel 126. As the helical gear drum 80 rotates, the ring 84 threaded on the helical gear drum 80 advances (or retracts, depending on the rotation). The arm 90 rotates CCW as the ring 84 advances due to the post 128 being disposed in the channel 126, as shown in FIG. 13.

Figure 14:
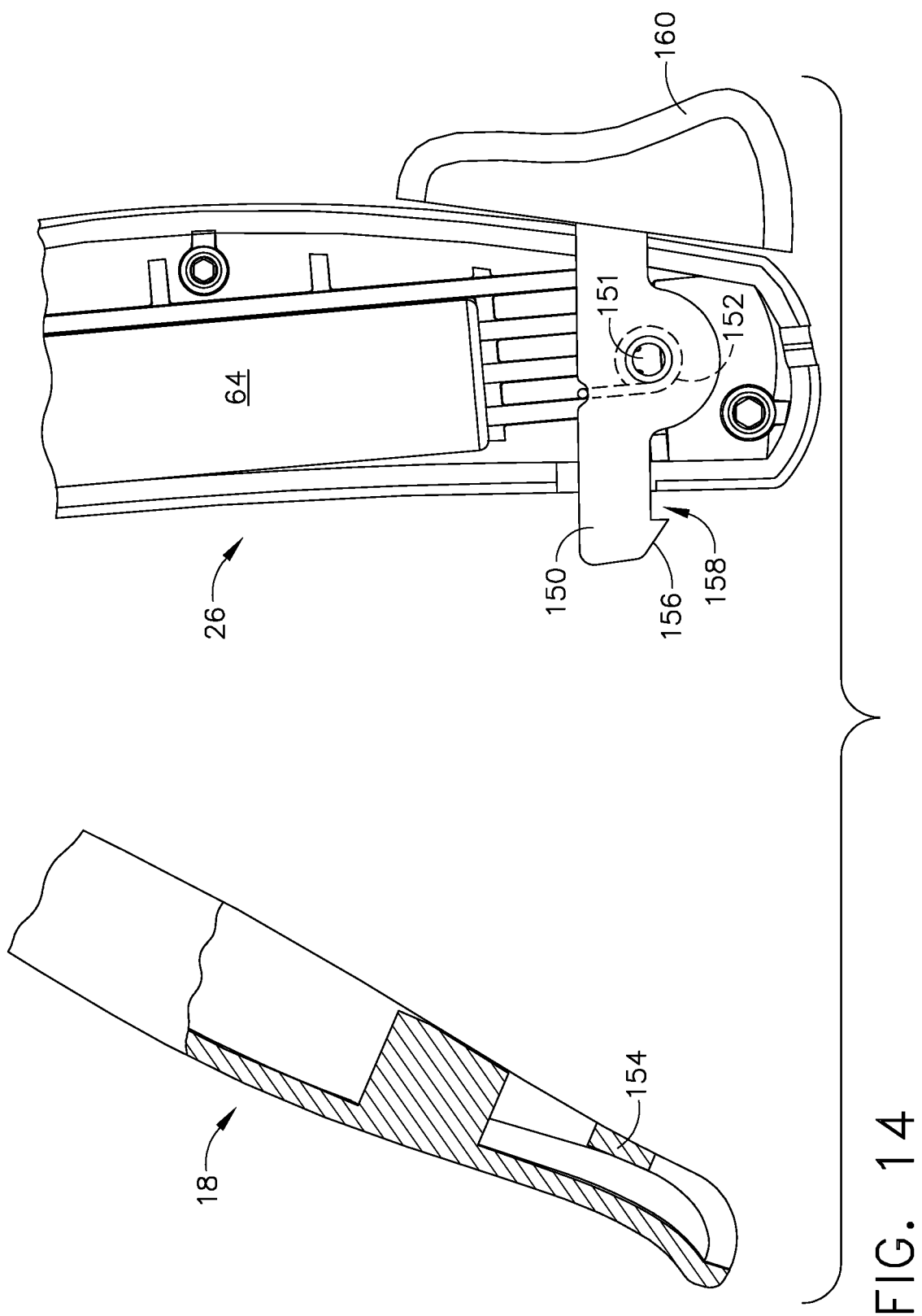
FIGS. 14-22 illustrate different mechanisms for locking the closure trigger according to various embodiments.
Figure 15:
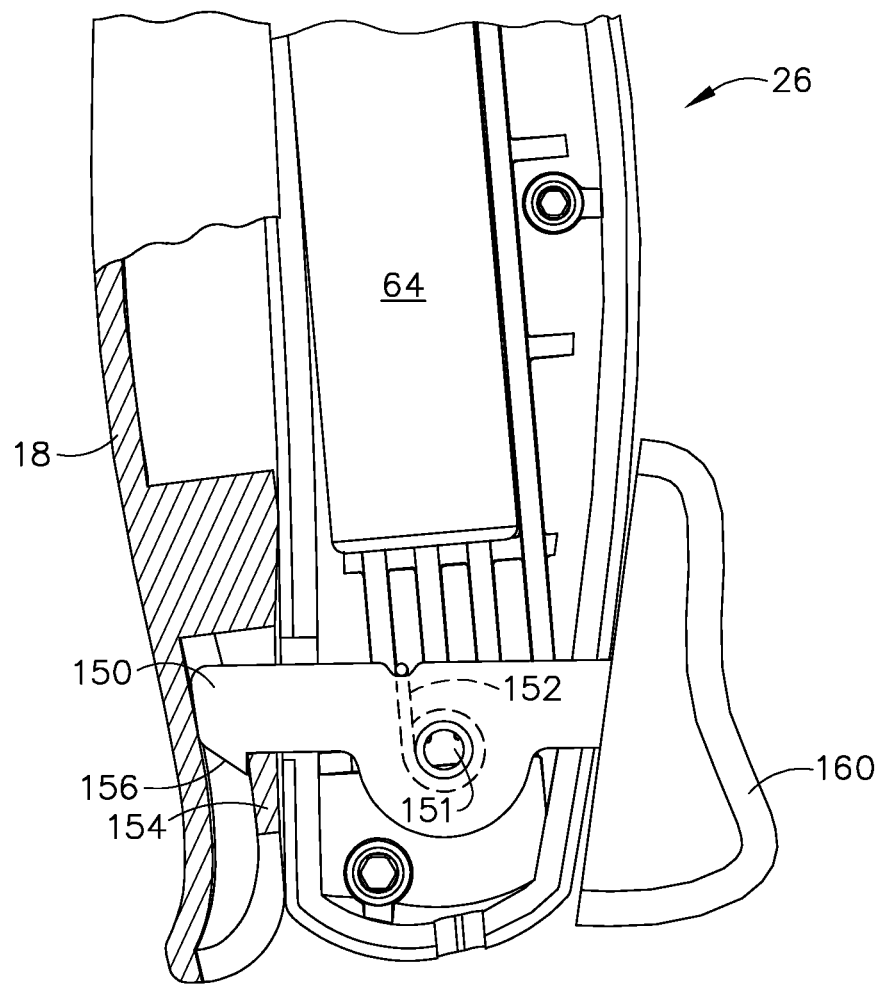

As mentioned above, in using a two-stroke motorized instrument, the operator first pulls back and locks the closure trigger 18. FIGS. 14 and 15 show one embodiment of a way to lock the closure trigger 18 to the pistol grip portion 26 of the handle 6. In the illustrated embodiment, the pistol grip portion 26 includes a hook 150 that is biased to rotate CCW about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or CW in FIGS. 12-13) until the closure bar 154 completely passes the sloped portion 156 passes into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 CW such that the closure bar 154 is released from the recessed notch 158.

Figure 16:
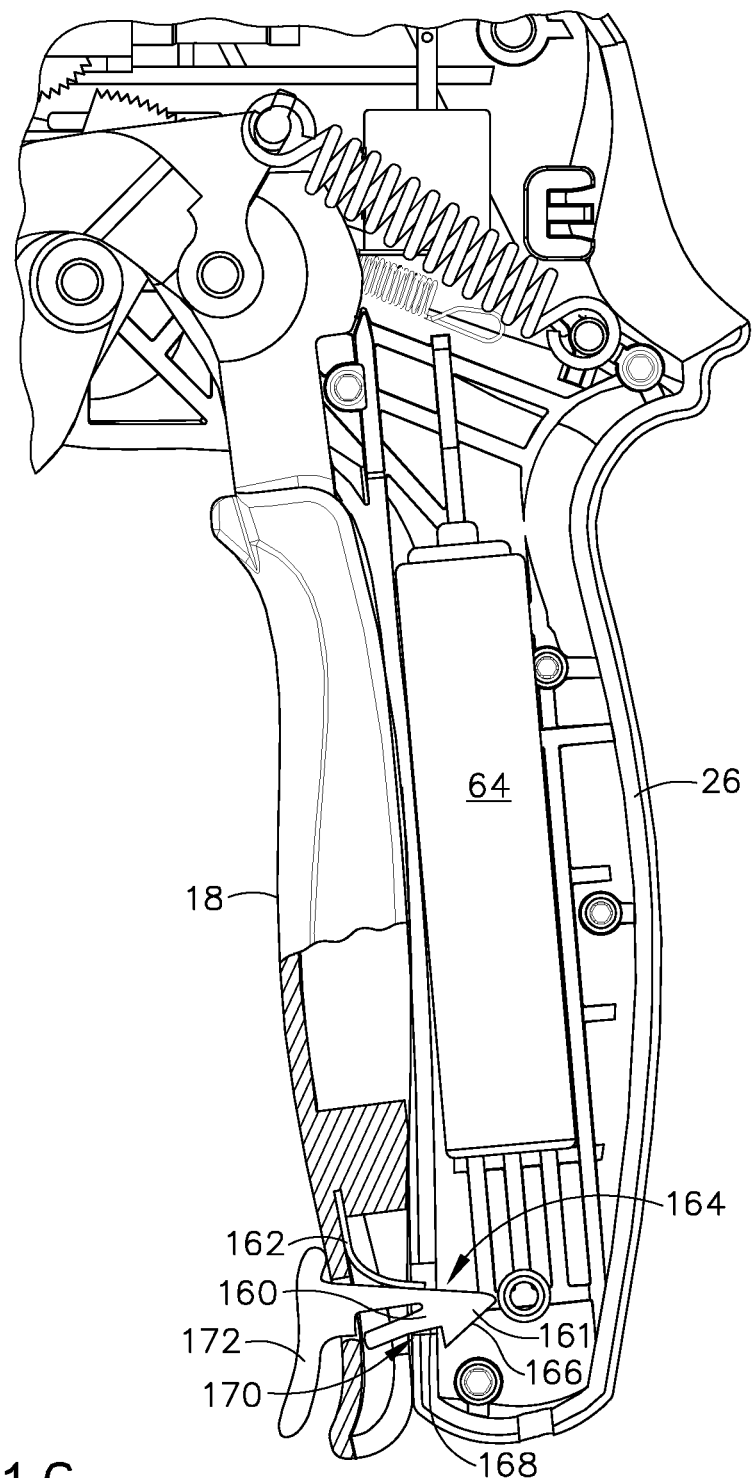

FIG. 16 shows another closure trigger locking mechanism according to various embodiments. In the embodiment of FIG. 16, the closure trigger 18 includes a wedge 160 having an arrow-head portion 161. The arrow-head portion 161 is biased downward (or CW) by a leaf spring 162. The wedge 160 and leaf spring 162 may be made from, for example, molded plastic. When the closure trigger 18 is retracted, the arrow-head portion 161 is inserted through an opening 164 in the pistol grip portion 26 of the handle 6. A lower chamfered surface 166 of the arrow-head portion 161 engages a lower sidewall 168 of the opening 164, forcing the arrow-head portion 161 to rotate CCW. Eventually the lower chamfered surface 166 fully passes the lower sidewall 168, removing the CCW force on the arrow-head portion 161, causing the lower sidewall 168 to slip into a locked position in a notch 170 behind the arrow-head portion 161.

To unlock the closure trigger 18, a user presses down on a button 172 on the opposite side of the closure trigger 18, causing the arrow-head portion 161 to rotate CCW and allowing the arrow-head portion 161 to slide out of the opening 164.

Figure 17:
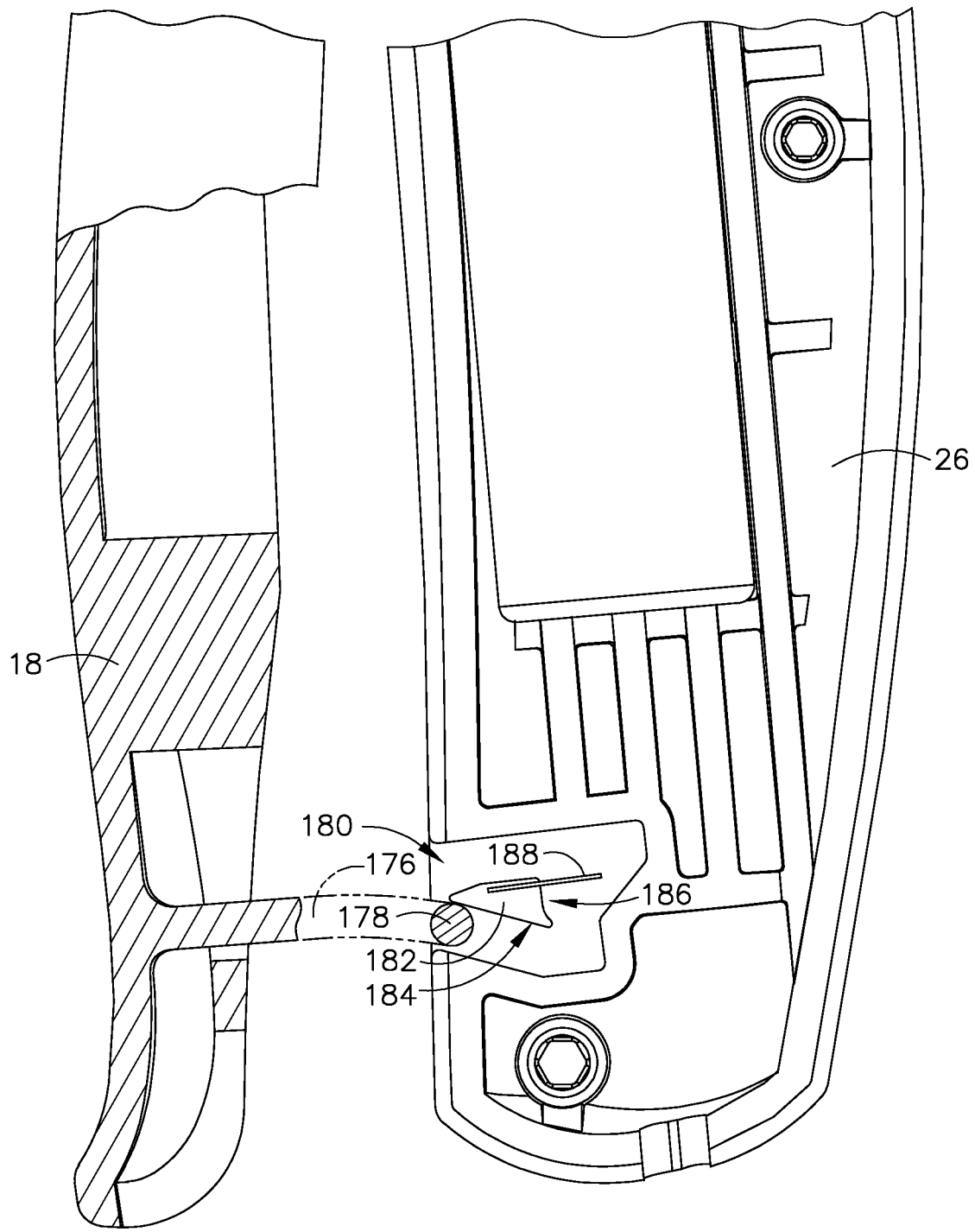
Figure 18:
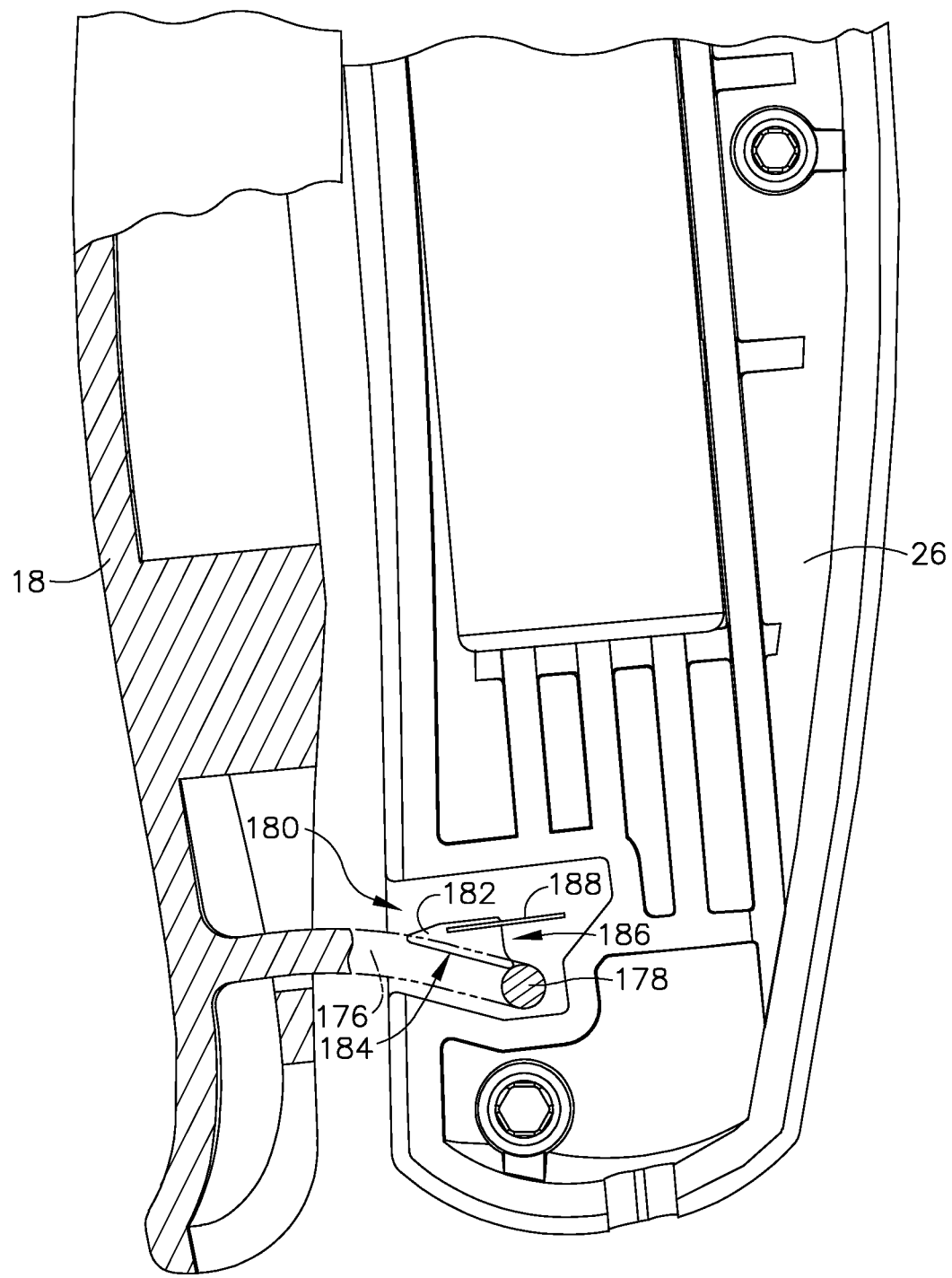
Figure 19:
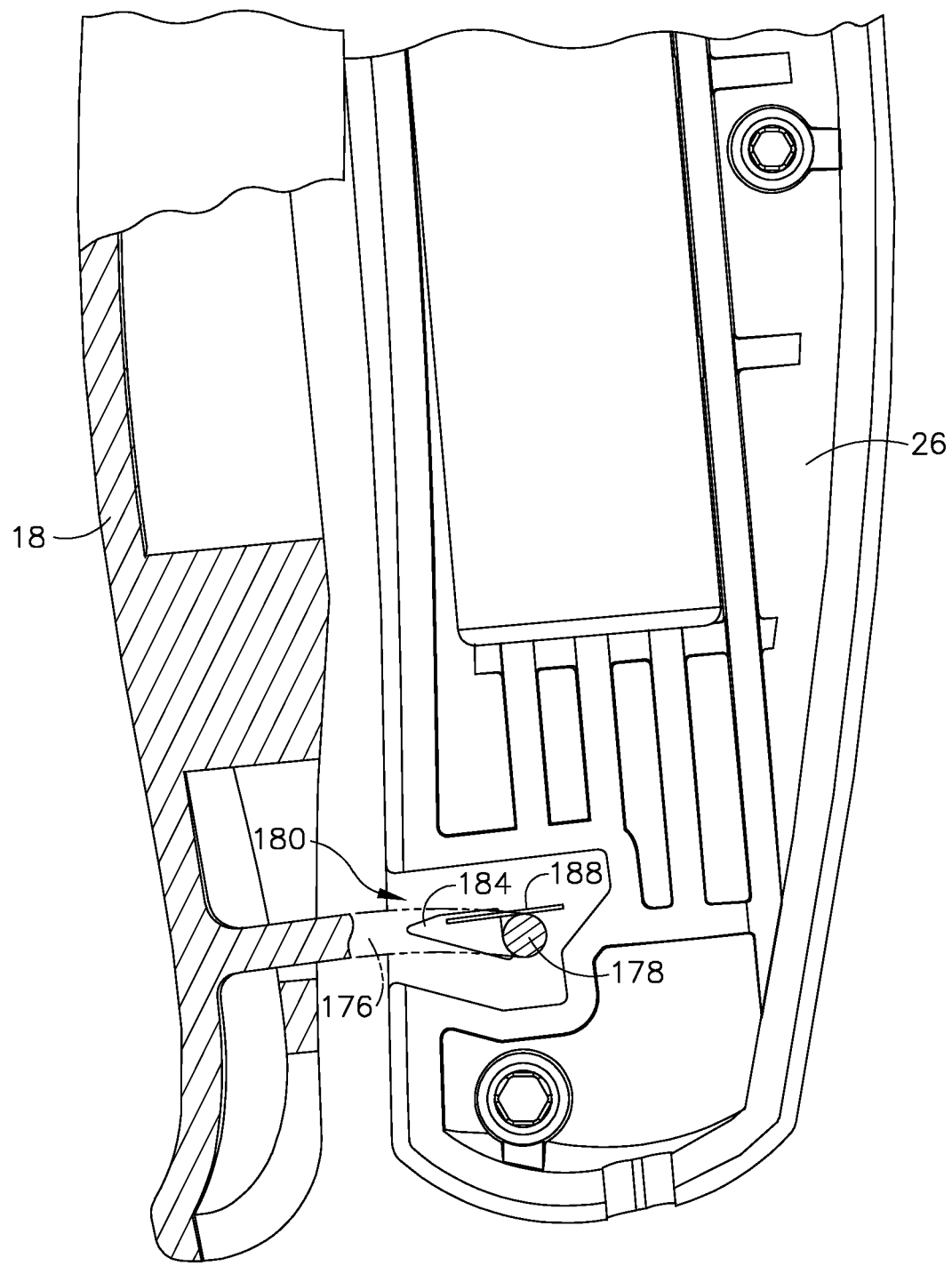

FIGS. 17-22 show a closure trigger locking mechanism according to another embodiment. As shown in this embodiment, the closure trigger 18 includes a flexible longitudinal arm 176 that includes a lateral pin 178 extending therefrom. The arm 176 and pin 178 may be made from molded plastic, for example. The pistol grip portion 26 of the handle 6 includes an opening 180 with a laterally extending wedge 182 disposed therein. When the closure trigger 18 is retracted, the pin 178 engages the wedge 182, and the pin 178 is forced downward (i.e., the arm 176 is rotated CW) by the lower surface 184 of the wedge 182, as shown in FIGS. 17 and 18. When the pin 178 fully passes the lower surface 184, the CW force on the arm 176 is removed, and the pin 178 is rotated CCW such that the pin 178 comes to rest in a notch 186 behind the wedge 182, as shown in FIG. 19, thereby locking the closure trigger 18. The pin 178 is further held in place in the locked position by a flexible stop 188 extending from the wedge 184.

Figure 20:
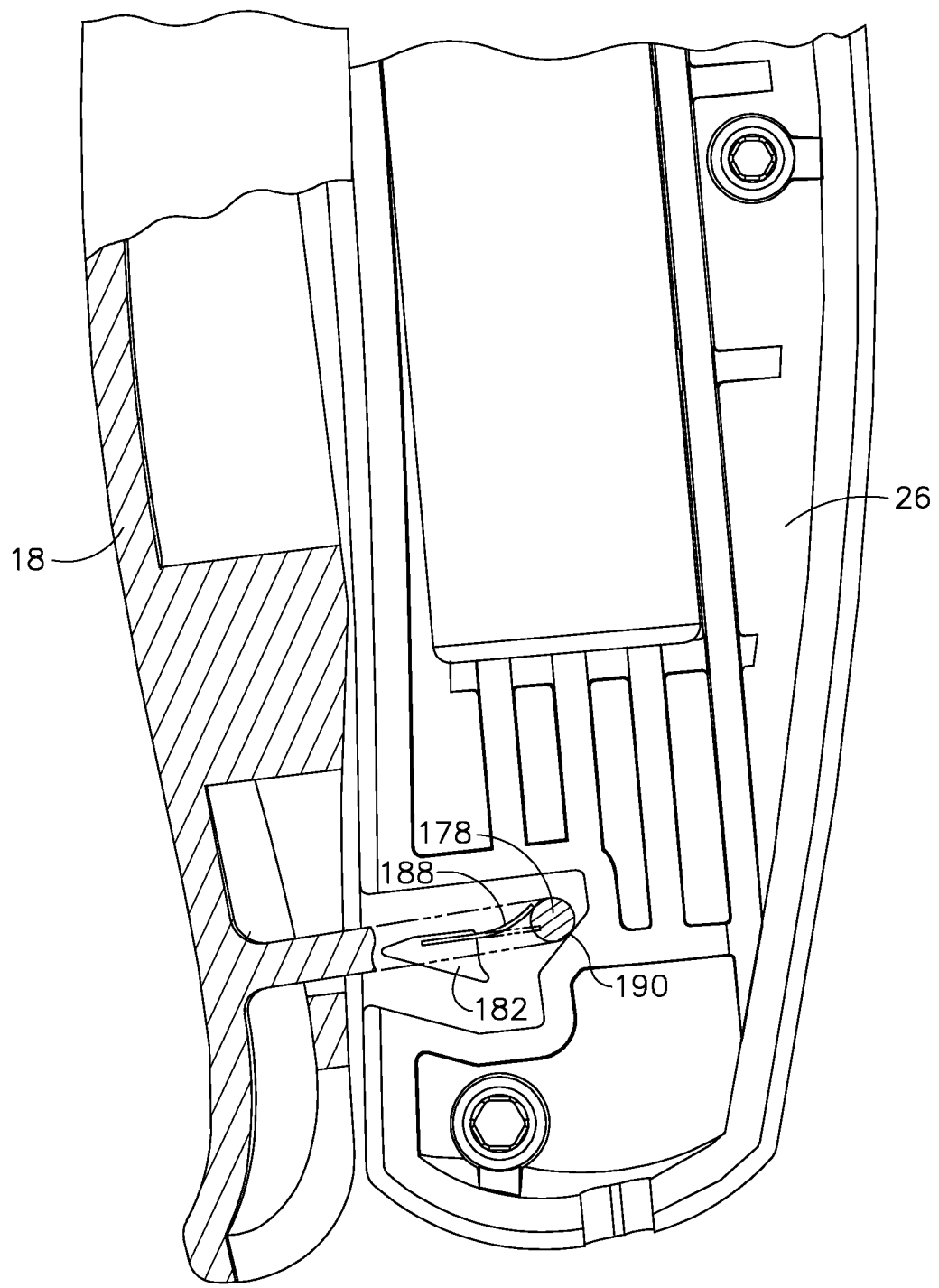
Figure 21:
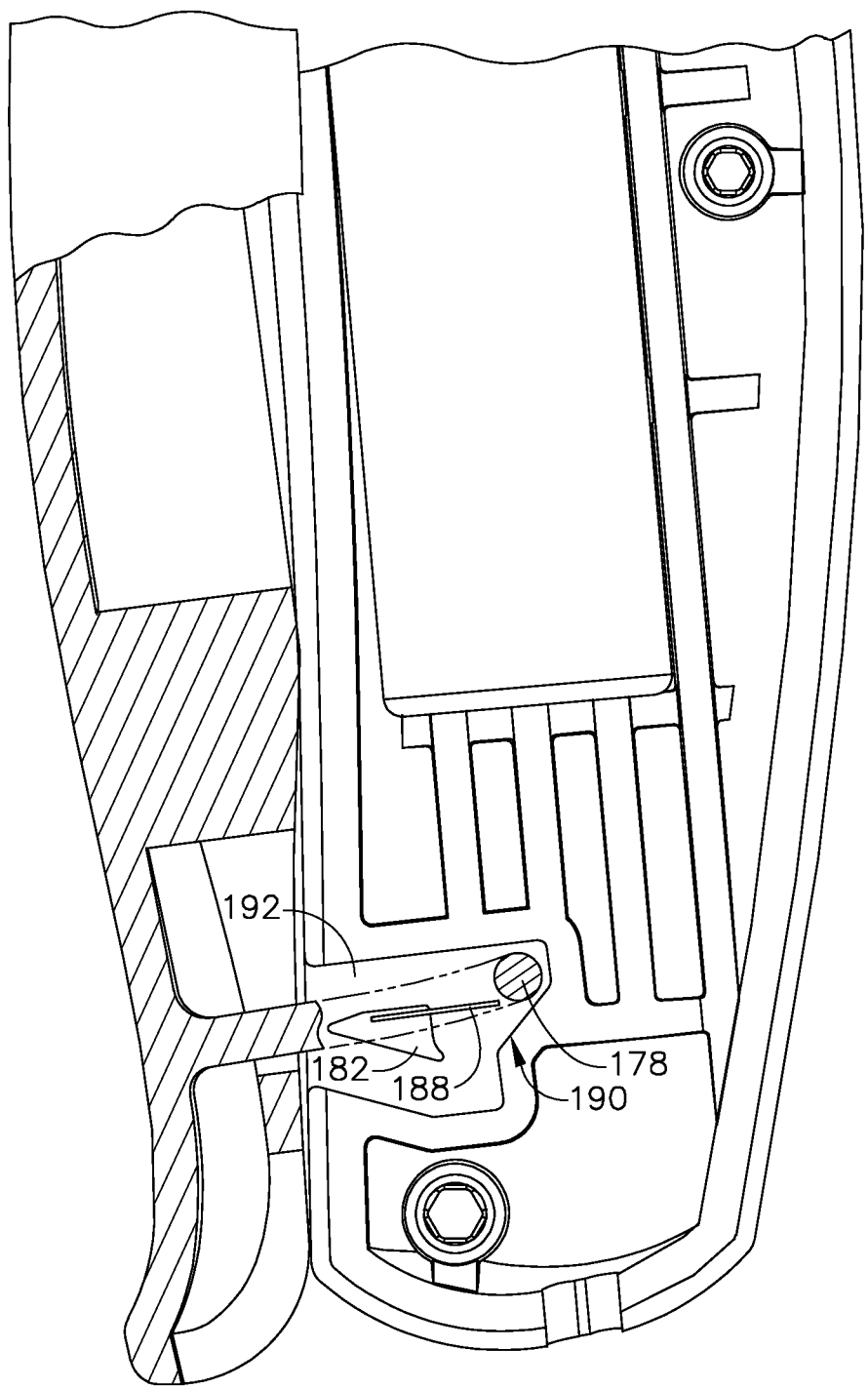
Figure 22:
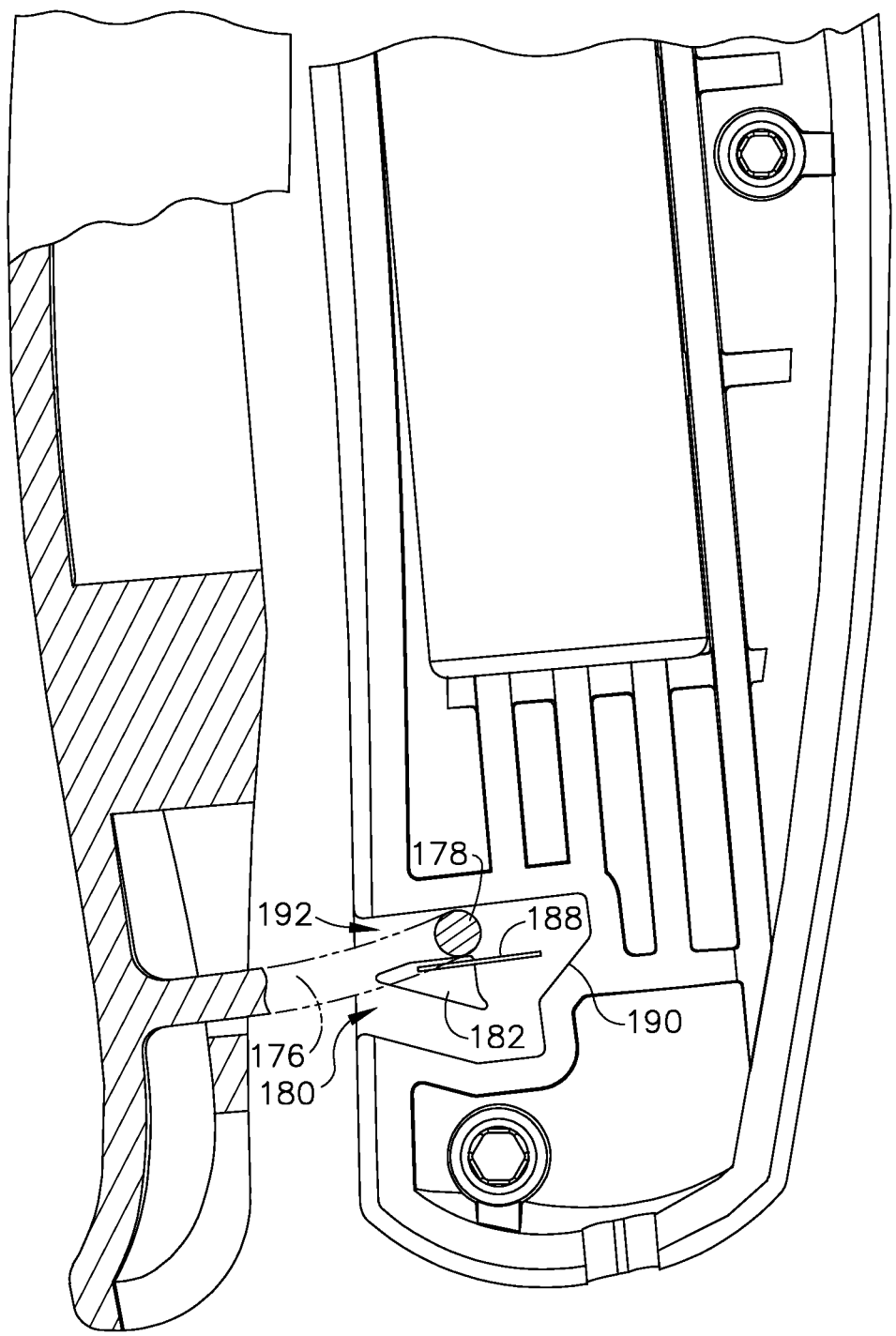
Figure 25:
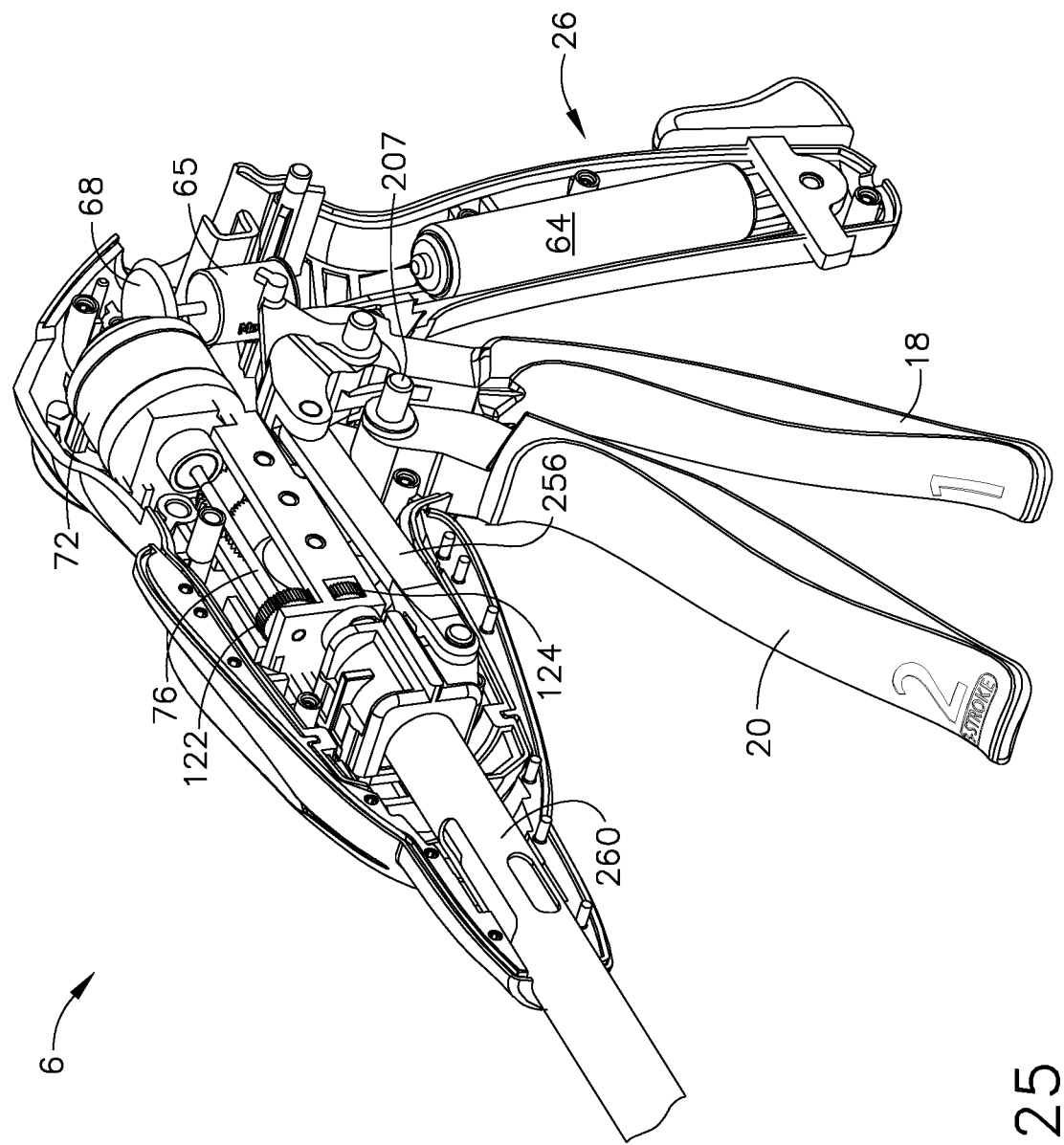
FIGS. 25-31 illustrate a surgical cutting and fastening instrument with power assist according to various embodiments.
Figure 26:
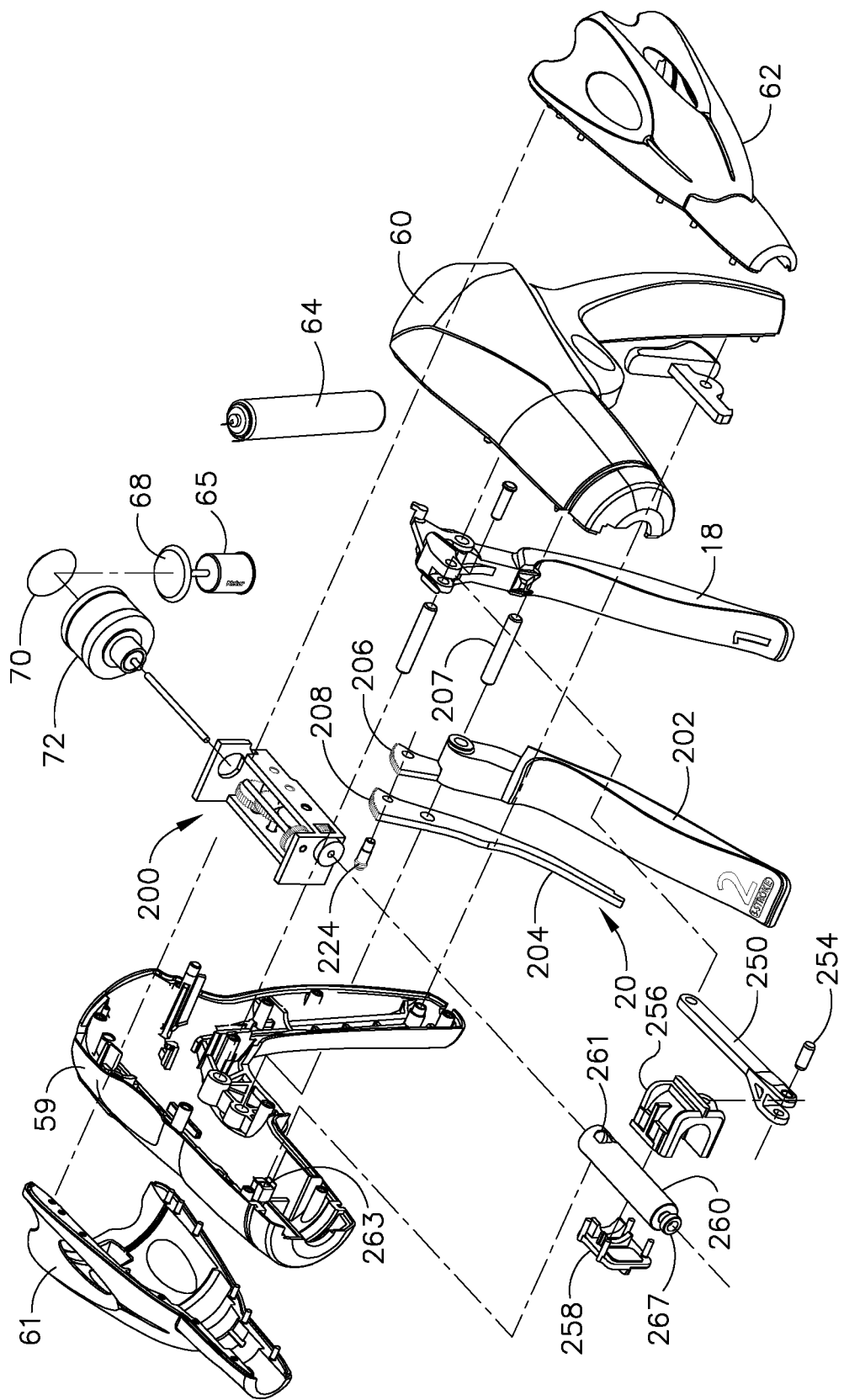
Figure 27:
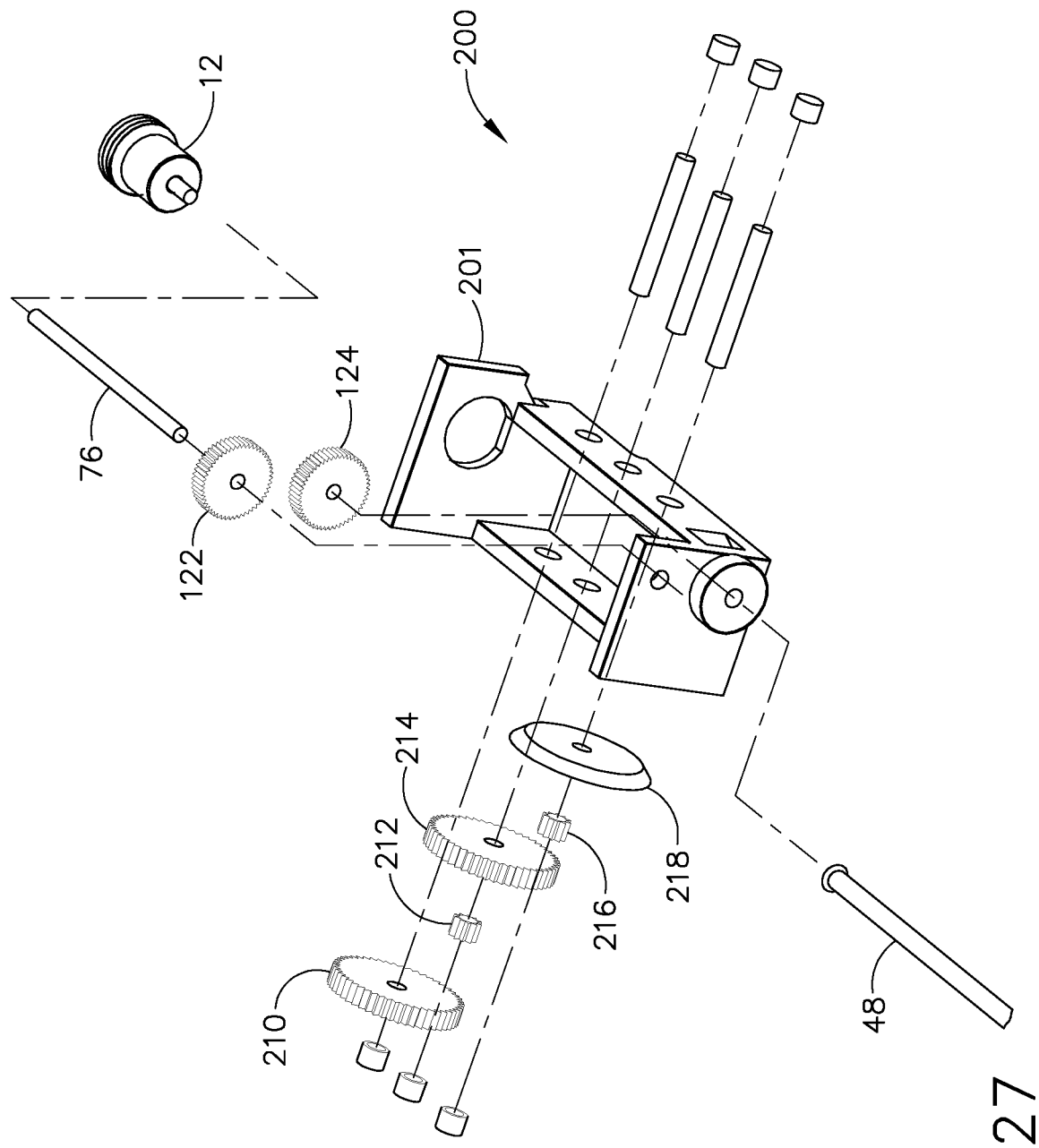
Figure 28:
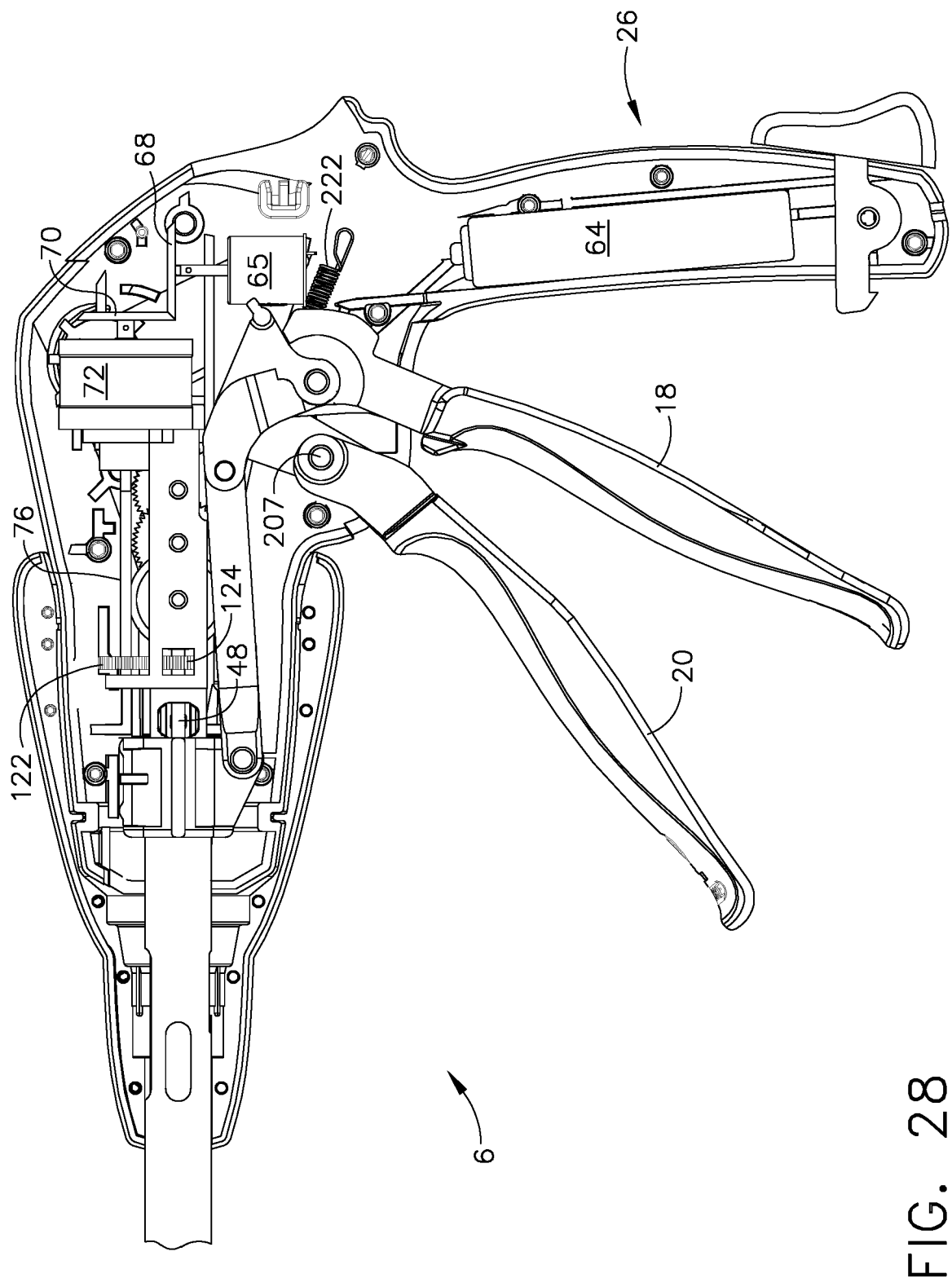
Figure 29:
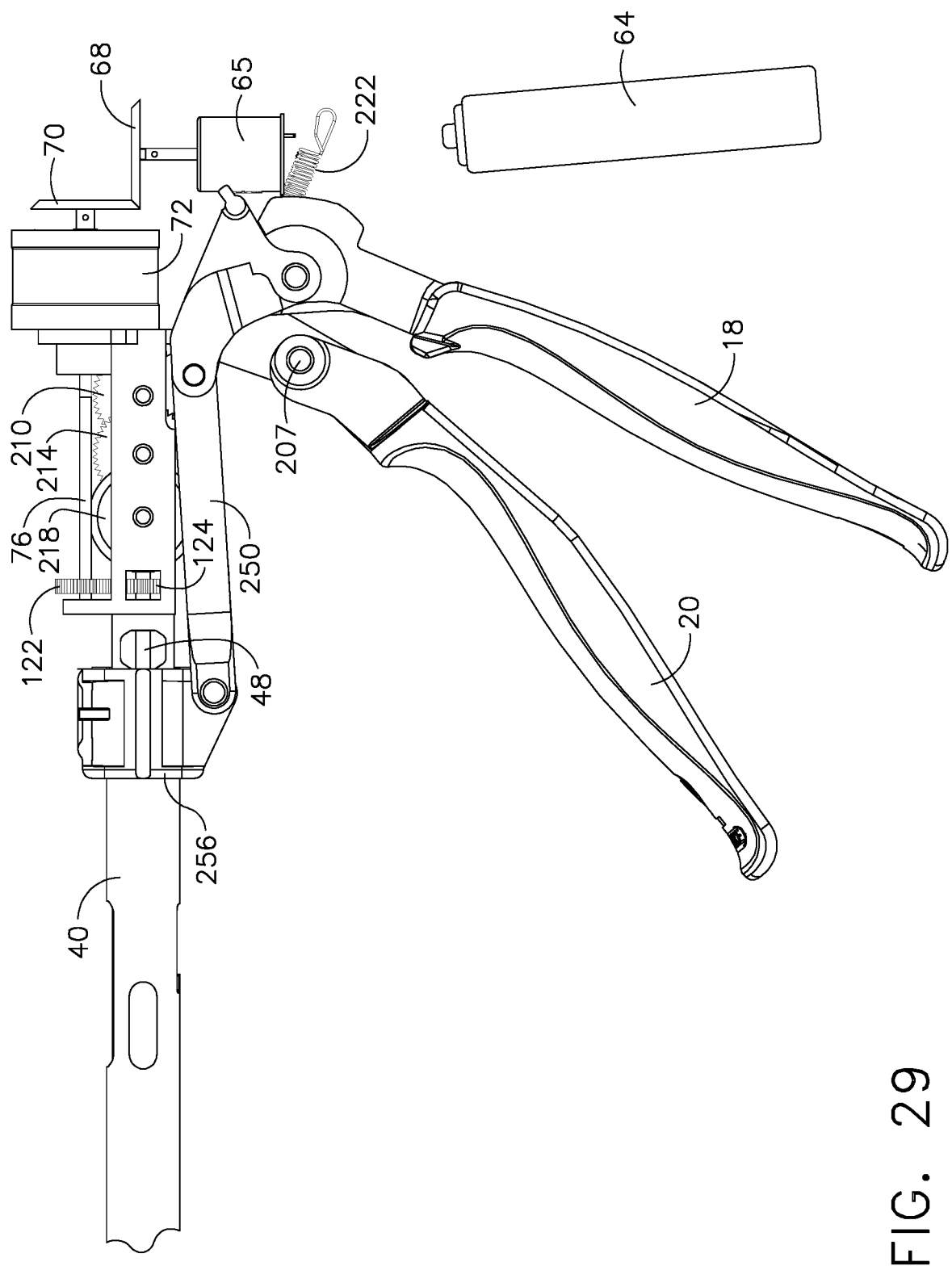
Figure 30:
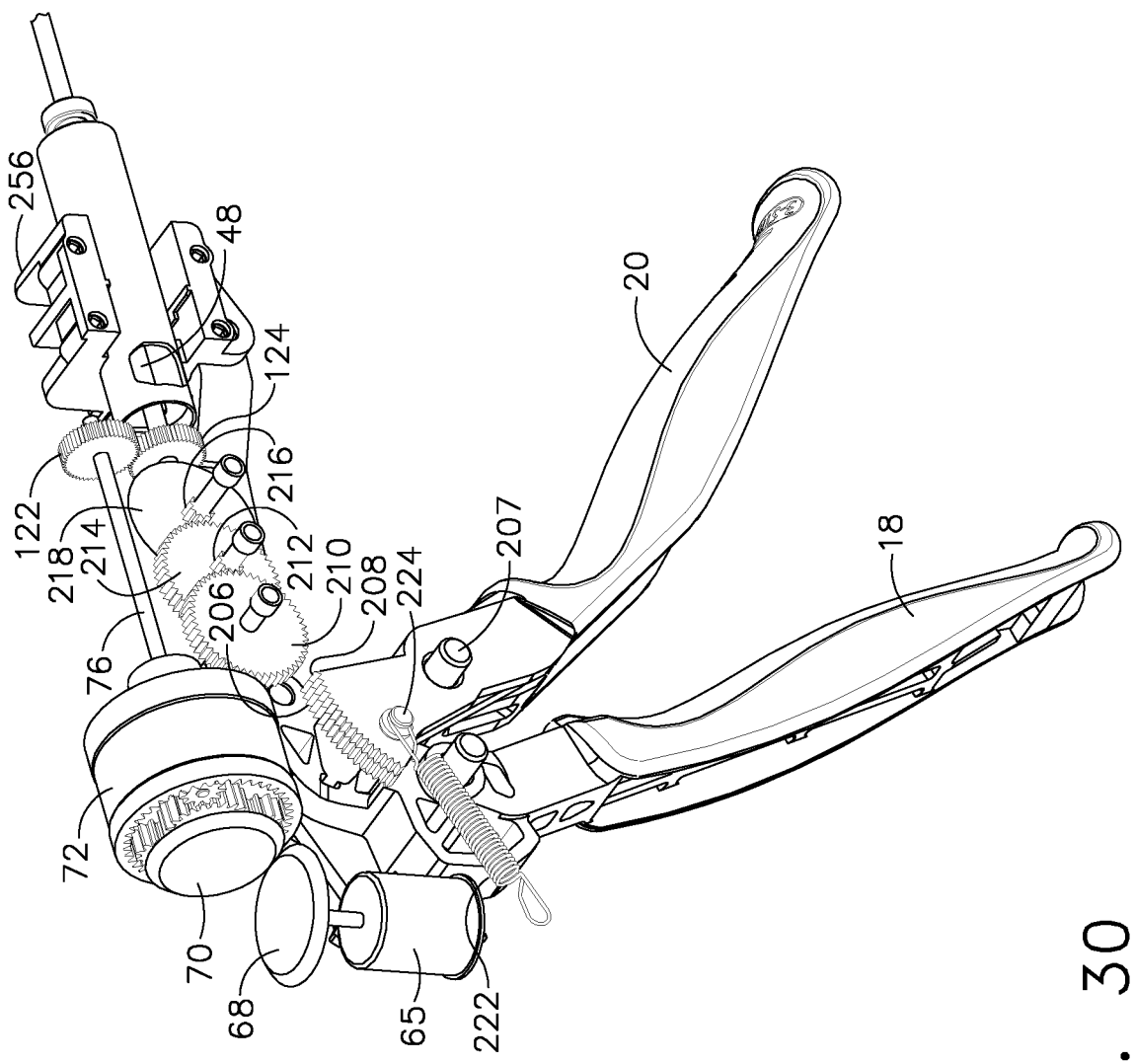
Figure 31:
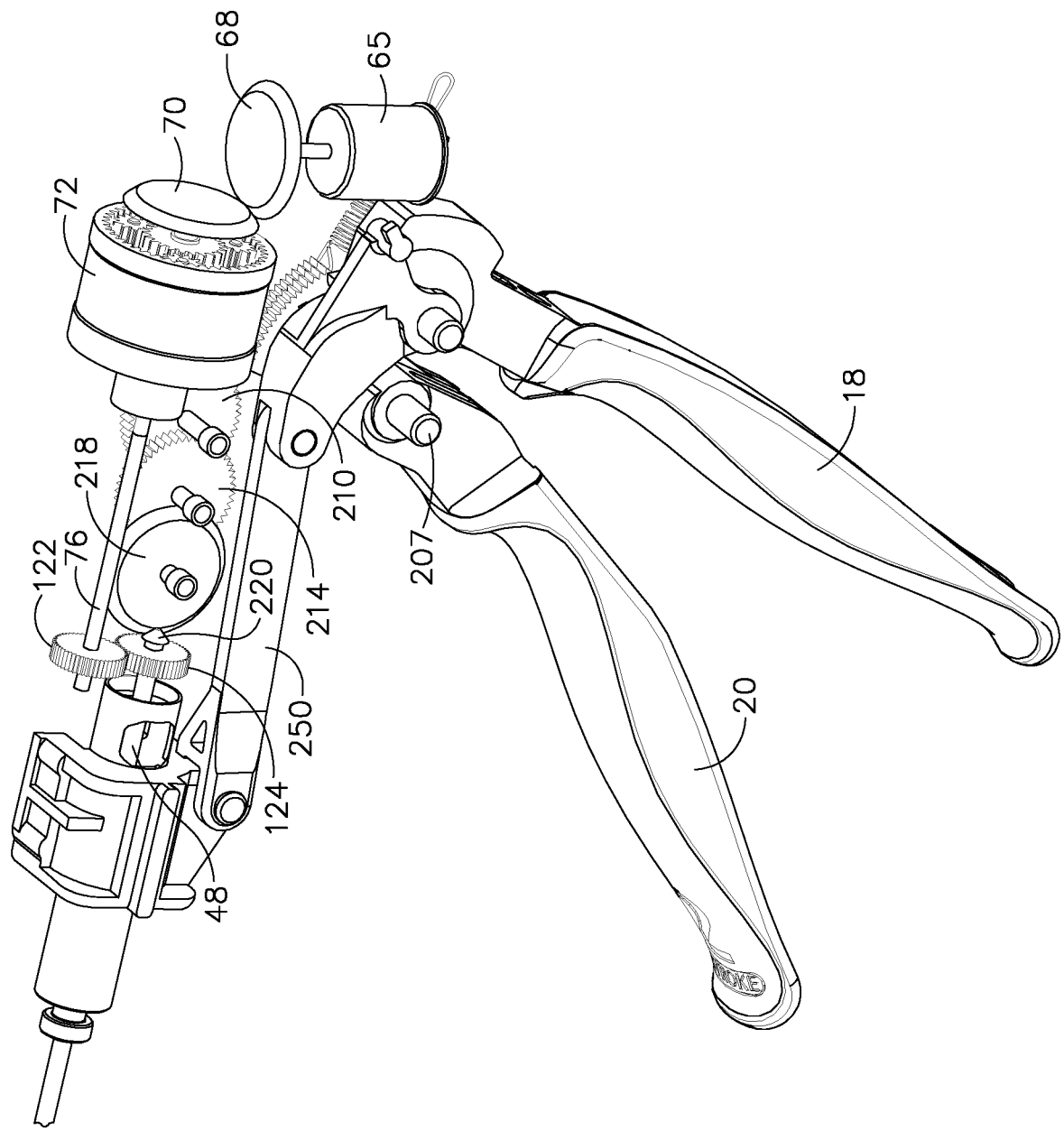

To unlock the closure trigger 18, the operator may further squeeze the closure trigger 18, causing the pin 178 to engage a sloped backwall 190 of the opening 180, forcing the pin 178 upward past the flexible stop 188, as shown in FIGS. 20 and 21. The pin 178 is then free to travel out an upper channel 192 in the opening 180 such that the closure trigger 18 is no longer locked to the pistol grip portion 26, as shown in FIG. 22.

FIGS. 23A-B show a universal joint ("u-joint") 195. The second piece 195-2 of the u-joint 195 rotates in a horizontal plane in which the first piece 195-1 lies. FIG. 23A shows the u-joint 195 in a linear (180°) orientation and FIG. 23B shows the u-joint 195 at approximately a 150° orientation. The u-joint 195 may be used instead of the bevel gears 52a-c (see FIG. 4, for example) at the articulation point 14 of the main drive shaft assembly to articulate the end effector 12. FIGS. 24A-B show a torsion cable 197 that may be used in lieu of both the bevel gears 52a-c and the u-joint 195 to realize articulation of the end effector 12.

FIGS. 25-31 illustrate another embodiment of a motorized, two-stroke surgical cutting and fastening instrument 10 with power assist. The embodiment of FIGS. 25-31 is similar to that of FIGS. 6-10 except that instead of the helical gear drum 80, the embodiment of FIGS. 23-28 includes an alternative gear drive assembly. The embodiment of FIGS. 25-31 includes a gear box assembly 200 including a number of gears disposed in a frame 201, wherein the gears are connected between the planetary gear 72 and the pinion gear 124 at the proximate end of the drive shaft 48. As explained further below, the gear box assembly 200 provides feedback to the user via the firing trigger 20 regarding the deployment and loading force of the end effector 12. Also, the user may provide power to the system via the gear box assembly 200 to assist the deployment of the end effector 12. In that sense, like the embodiments described above, the embodiment of FIGS. 23-32 is another power assist, motorized instrument 10 that provides feedback to the user regarding the loading force experienced by the cutting instrument.

In the illustrated embodiment, the firing trigger 20 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 209 may be inserted through openings in the firing trigger pieces 202, 204 and may be the point about which the firing trigger 20 rotates. In addition, a spring 222 may bias the firing trigger 20 to rotate in a CCW direction. The spring 222 may have a distal end connected to a pin 224 that is connected to the pieces 202, 204 of the firing trigger 20. The proximate end of the spring 222 may be connected to one of the handle exterior lower side pieces 59, 60.

In the illustrated embodiment, both the main body portion 202 and the stiffening portion 204 includes gear portions 206, 208 (respectively) at their upper end portions. The gear portions 206, 208 engage a gear in the gear box assembly 200, as explained below, to drive the main drive shaft assembly and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 20. In addition, the first gear 210 engages a smaller second gear 212, the smaller second gear 212 being coaxial with a large third gear 214. The third gear 214 engages a smaller fourth gear 216, the smaller fourth gear being coaxial with a fifth gear 218. The fifth gear 218 is a 90° bevel gear that engages a mating 90° bevel gear 220 (best shown in FIG. 31) that is connected to the pinion gear 124 that drives the main drive shaft 48.

In operation, when the user retracts the firing trigger 20, a run motor sensor (not shown) is activated, which may provide a signal to the motor 65 to rotate at a rate proportional to the extent or force with which the operator is retracting the firing trigger 20. This causes the motor 65 to rotate at a speed proportional to the signal from the sensor. The sensor is not shown for this embodiment, but it could be similar to the run motor sensor 110 described above. The sensor could be located in the handle 6 such that it is depressed when the firing trigger 20 is retracted. Also, instead of a proportional-type sensor, an on/off type sensor may be used.

Rotation of the motor 65 causes the bevel gears 66, 70 to rotate, which causes the planetary gear 72 to rotate, which causes, via the drive shaft 76, the gear 122 to rotate. The gear 122 meshes with the pinion gear 124, which is connected to the main drive shaft 48. Thus, rotation of the pinion gear 124 drives the main drive shaft 48, which causes actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate CCW when the motor 65 provides forward drive for the end effector 12 (and to rotate CCW when the motor 65 rotates in reverse to retract the end effector 12). In that way, the user experiences feedback regarding loading force and deployment of the end effector 12 by way of the user's grip on the firing trigger 20. Thus, when the user retracts the firing trigger 20, the operator will experience a resistance related to the load force experienced by the end effector 12. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portions 206, 208 to rotate CCW, which causes the gears of the gear box assembly 200 to rotate, thereby causing the pinion gear 124 to rotate, which causes the main drive shaft 48 to rotate.

Although not shown in FIGS. 25-31, the instrument 10 may further include reverse motor and stop motor sensors. As described above, the reverse motor and stop motor sensors may detect, respectively, the end of the cutting stroke (full deployment of the knife/sled driving member 32) and the end of retraction operation (full retraction of the knife/sled driving member 32). A similar circuit to that described above in connection with FIG. 11 may be used to appropriately power the motor 65.

FIGS. 32-36 illustrate a two-stroke, motorized surgical cutting and fastening instrument 10 with power assist according to another embodiment. The embodiment of FIGS. 32-36 is similar to that of FIGS. 25-31 except that in the embodiment of FIGS. 32-36, the firing trigger 20 includes a lower portion 228 and an upper portion 230. Both portions 228, 230 are connected to and pivot about a pivot pin 207 that is disposed through each portion 228, 230. The upper portion 230 includes a gear portion 232 that engages the first gear 210 of the gear box assembly 200. The spring 222 is connected to the upper portion 230 such that the upper portion is biased to rotate in the CW direction. The upper portion 230 may also include a lower arm 234 that contacts an upper surface of the lower portion 228 of the firing trigger 20 such that when the upper portion 230 is caused to rotate CW the lower portion 228 also rotates CW, and when the lower portion 228 rotates CCW the upper portion 230 also rotates CCW. Similarly, the lower portion 228 includes a rotational stop 238 that engages a lower shoulder of the upper portion 230. In that way, when the upper portion 230 is caused to rotate CCW the lower portion 228 also rotates CCW, and when the lower portion 228 rotates CW the upper portion 230 also rotates CW.

The illustrated embodiment also includes the run motor sensor 110 that communicates a signal to the motor 65 that, in various embodiments, may cause the motor 65 to rotate at a speed proportional to the force applied by the operator when retracting the firing trigger 20. The sensor 110 may be, for example, a rheostat or some other variable resistance sensor, as explained herein. In addition, the instrument 10 may include a reverse motor sensor 130 that is tripped or switched when contacted by a front face 242 of the upper portion 230 of the firing trigger 20. When activated, the reverse motor sensor 130 sends a signal to the motor 65 to reverse direction. Also, the instrument 10 may include a stop motor sensor 142 that is tripped or actuated when contacted by the lower portion 228 of the firing trigger 20. When activated, the stop motor sensor 142 sends a signal to stop the reverse rotation of the motor 65.

Figure 32:
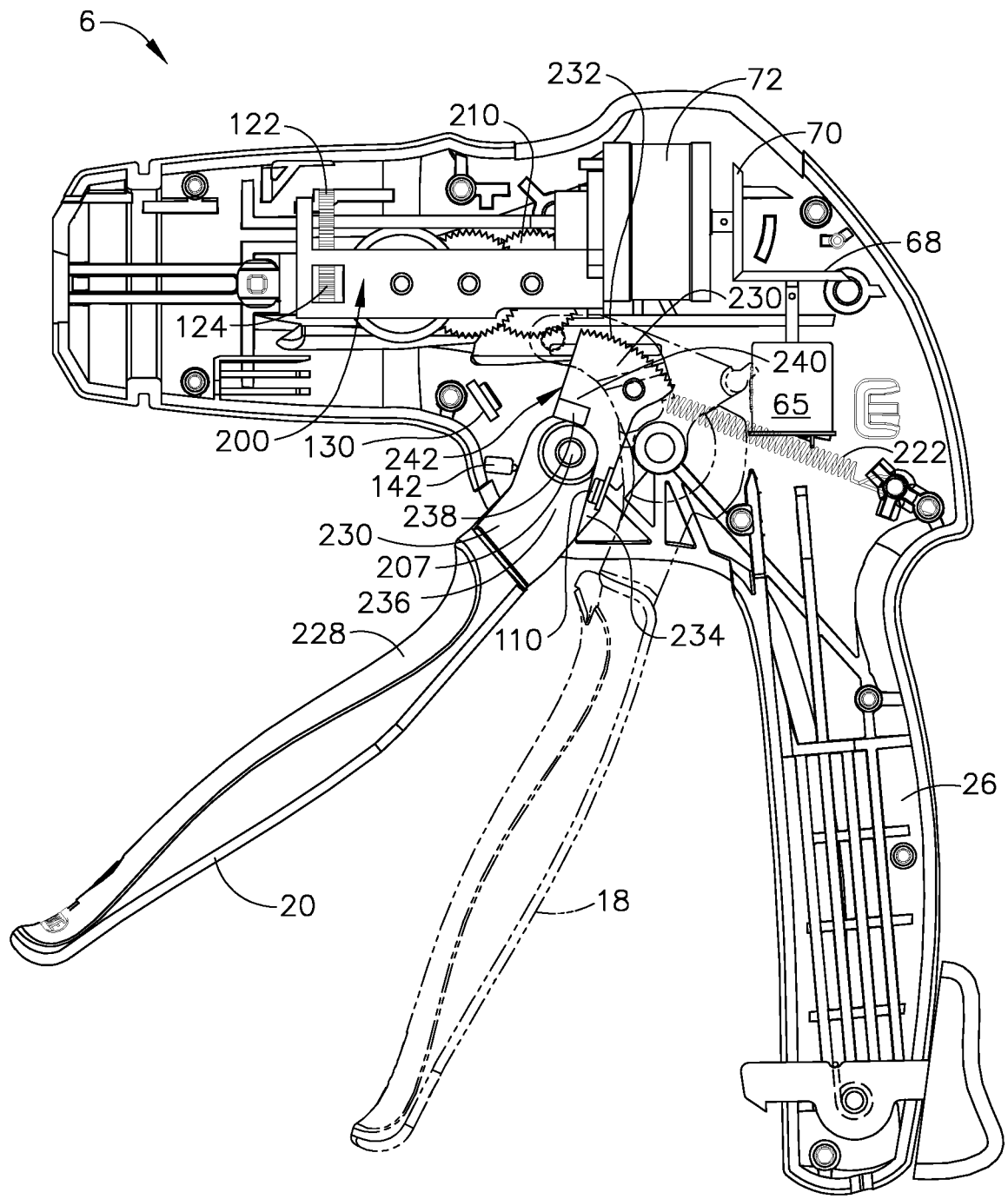
FIGS. 32-36 illustrate a surgical cutting and fastening instrument with power assist according to yet other various embodiments.
Figure 33:
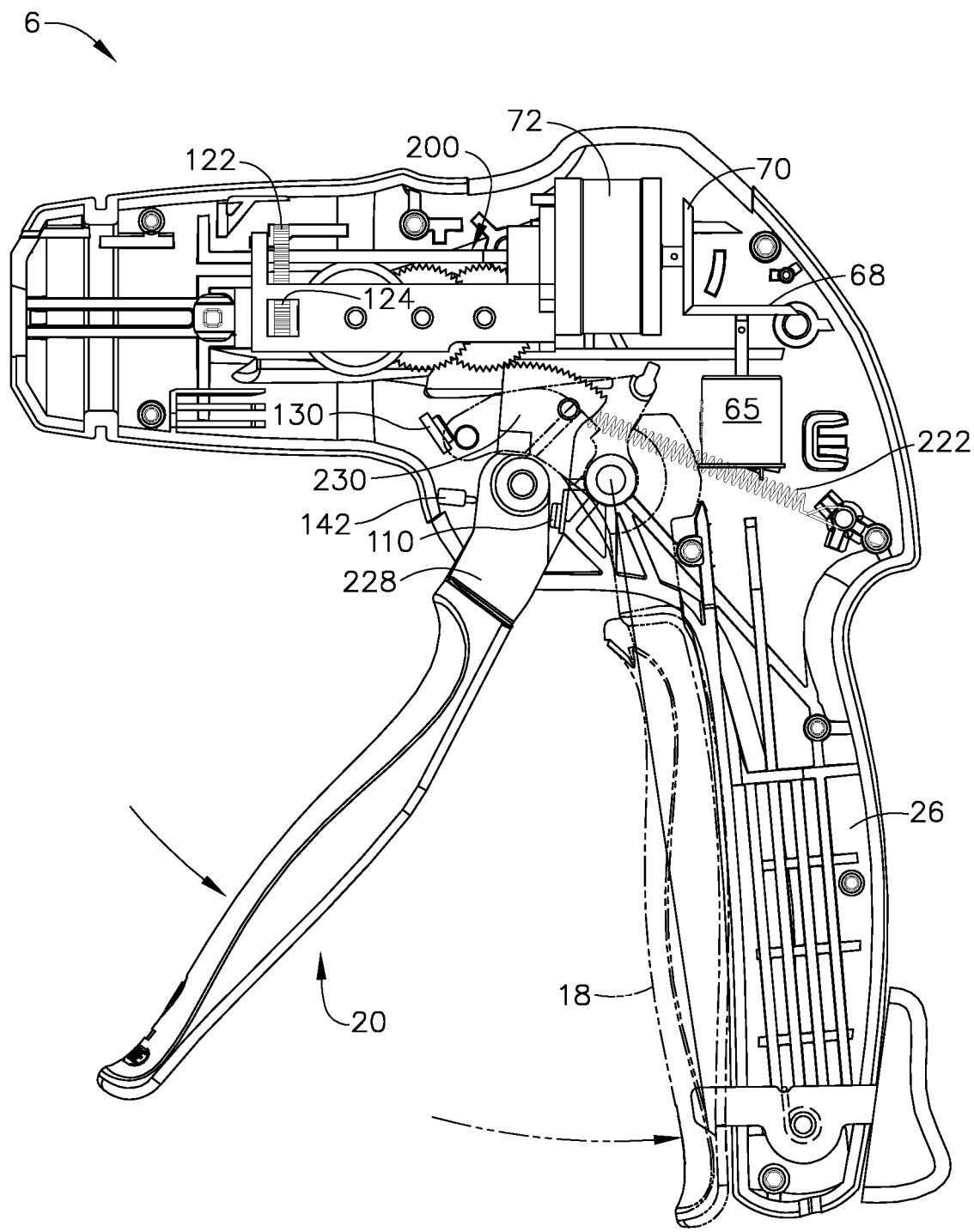
Figure 34:
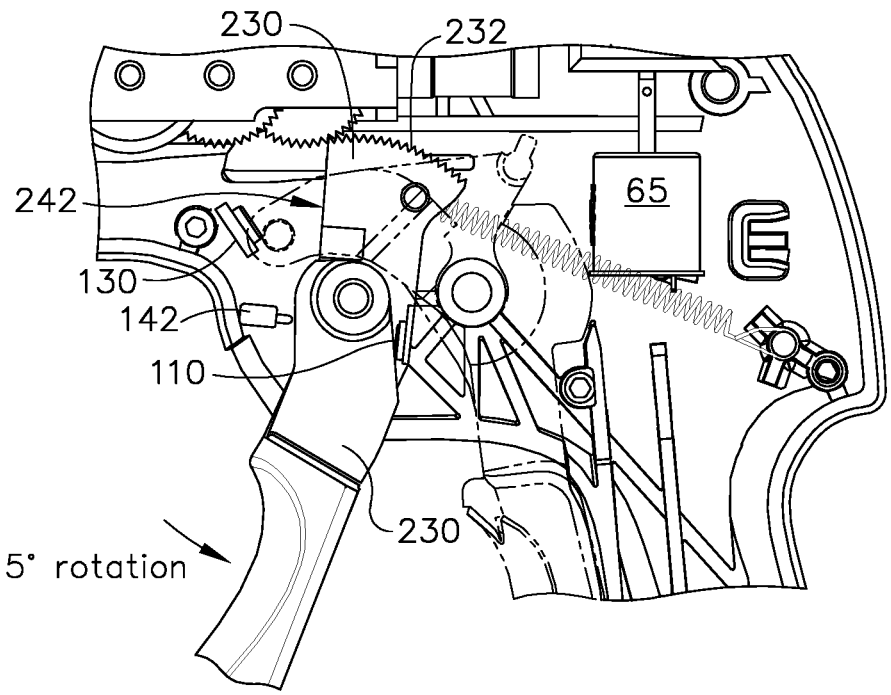
Figure 35:
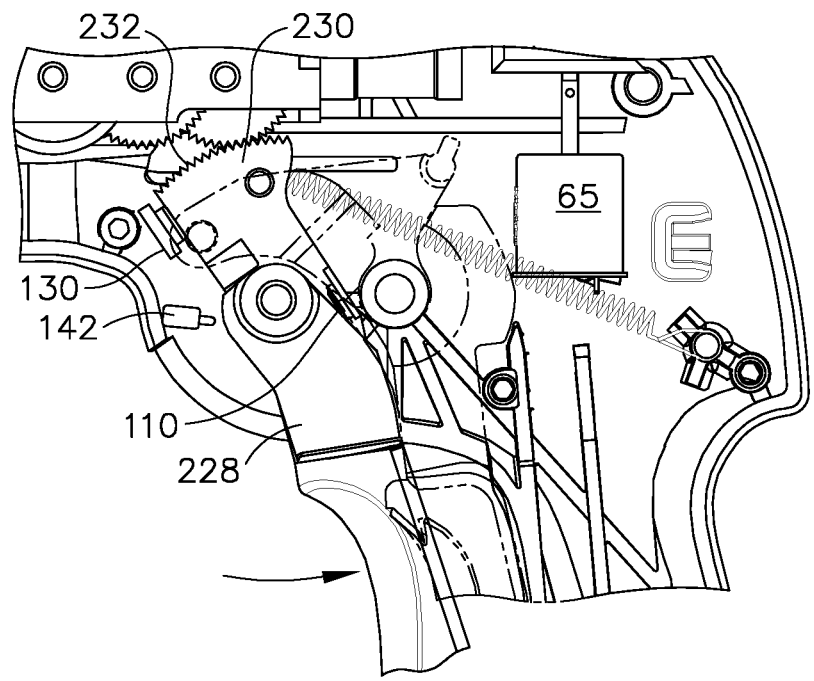
Figure 36:
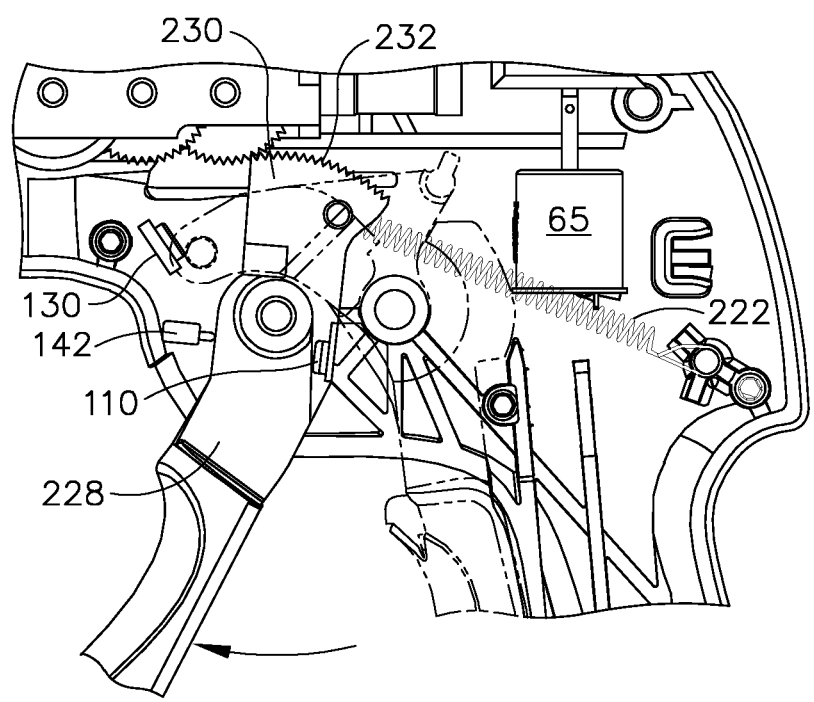

In operation, when an operator retracts the closure trigger 18 into the locked position, the firing trigger 20 is retracted slightly (through mechanisms known in the art, including U.S. Pat. No. 6,978,921 entitled SURGICAL STAPLING INSTRUMENT INCORPORATING AN E-BEAM FIRING MECHANISM, filed on May 20, 2003, and U.S. Pat. No. 6,905,057 entitled SURGICAL STAPLING INSTRUMENT INCORPORATING A FIRING MECHANISM HAVING A LINKED RACK TRANSMISSION, filed on Sep. 29, 2003, the entire disclosures of which are incorporated herein by reference, so that the user can grasp the firing trigger 20 to initiate the cutting/stapling operation, as shown in FIGS. 32 and 33. At that point, as shown in FIG. 33, the gear portion 232 of the upper portion 230 of the firing trigger 20 moves into engagement with the first gear 210 of the gear box assembly 200. When the operator retracts the firing trigger 20, according to various embodiments, the firing trigger 20 may rotate a small amount, such as five degrees, before tripping the run motor sensor 110, as shown in FIG. 34. Activation of the sensor 110 causes the motor 65 to forward rotate at a rate proportional to the retraction force applied by the operator. The forward rotation of the motor 65 causes, as described above, the main drive shaft 48 to rotate, which causes the knife 32 in the end effector 12 to be deployed (i.e., begin traversing the channel 22). Rotation of the pinion gear 124, which is connected to the main drive shaft 48, causes the gears 210-220 in the gear box assembly 200 to rotate. Since the first gear 210 is in engagement with the gear portion 232 of the upper portion 230 of the firing trigger 20, the upper portion 232 is caused to rotate CCW, which causes the lower portion 228 to also rotate CCW.

When the knife 32 is fully deployed (i.e., at the end of the cutting stroke), the front face 242 of the upper portion 230 trips the reverse motor sensor 130, which sends a signal to the motor 65 to reverse rotational directional. This causes the main drive shaft assembly to reverse rotational direction to retract the knife 32. Reverse rotation of the main drive shaft assembly causes the gears 210-220 in the gear box assembly to reverse direction, which causes the upper portion 230 of the firing trigger 20 to rotate CW, which causes the lower portion 228 of the firing trigger 20 to rotate CW until the lower portion 228 trips or actuates the stop motor sensor 142 when the knife 32 is fully retracted, which causes the motor 65 to stop. In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particular, to the loading force experienced by the knife 32. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portion 232 of the upper portion 230 to rotate CCW, which causes the gears of the gear box assembly 200 to rotate, thereby causing the pinion gear 124 to rotate, which causes the main drive shaft assembly to rotate.

The above-described embodiments employed power-assist user feedback systems, with or without adaptive control (e.g., using a sensor 110, 130, and 142 outside of the closed loop system of the motor, gear drive train, and end effector) for a two-stroke, motorized surgical cutting and fastening instrument. That is, force applied by the user in retracting the firing trigger 20 may be added to the force applied by the motor 65 by virtue of the firing trigger 20 being geared into (either directly or indirectly) the gear drive train between the motor 65 and the main drive shaft 48. In other embodiments, the user may be provided with tactile feedback regarding the position of the knife 32 in the end effector, but without having the firing trigger 20 geared into the gear drive train. FIGS. 37-40 illustrate a motorized surgical cutting and fastening instrument with such a tactile position feedback system.

In the illustrated embodiment of FIGS. 37-40, the firing trigger 20 may have a lower portion 228 and an upper portion 230, similar to the instrument 10 shown in FIGS. 32-36. Unlike the embodiment of FIGS. 32-36, however, the upper portion 230 does not have a gear portion that mates with part of the gear drive train. Instead, the instrument includes a second motor 265 with a threaded rod 266 threaded therein. The threaded rod 266 reciprocates longitudinally in and out of the motor 265 as the motor 265 rotates, depending on the direction of rotation. The instrument 10 also includes an encoder 268 that is responsive to the rotations of the main drive shaft 48 for translating the incremental angular motion of the main drive shaft 48 (or other component of the main drive assembly) into a corresponding series of digital signals, for example. In the illustrated embodiment, the pinion gear 124 includes a proximate drive shaft 270 that connects to the encoder 268.

The instrument 10 also includes a control circuit (not shown), which may be implemented using a microcontroller or some other type of integrated circuit, that receives the digital signals from the encoder 268. Based on the signals from the encoder 268, the control circuit may calculate the stage of deployment of the knife 32 in the end effector 12. That is, the control circuit can calculate if the knife 32 is fully deployed, fully retracted, or at an intermittent stage. Based on the calculation of the stage of deployment of the end effector 12, the control circuit may send a signal to the second motor 265 to control its rotation to thereby control the reciprocating movement of the threaded rod 266.

Figure 37:
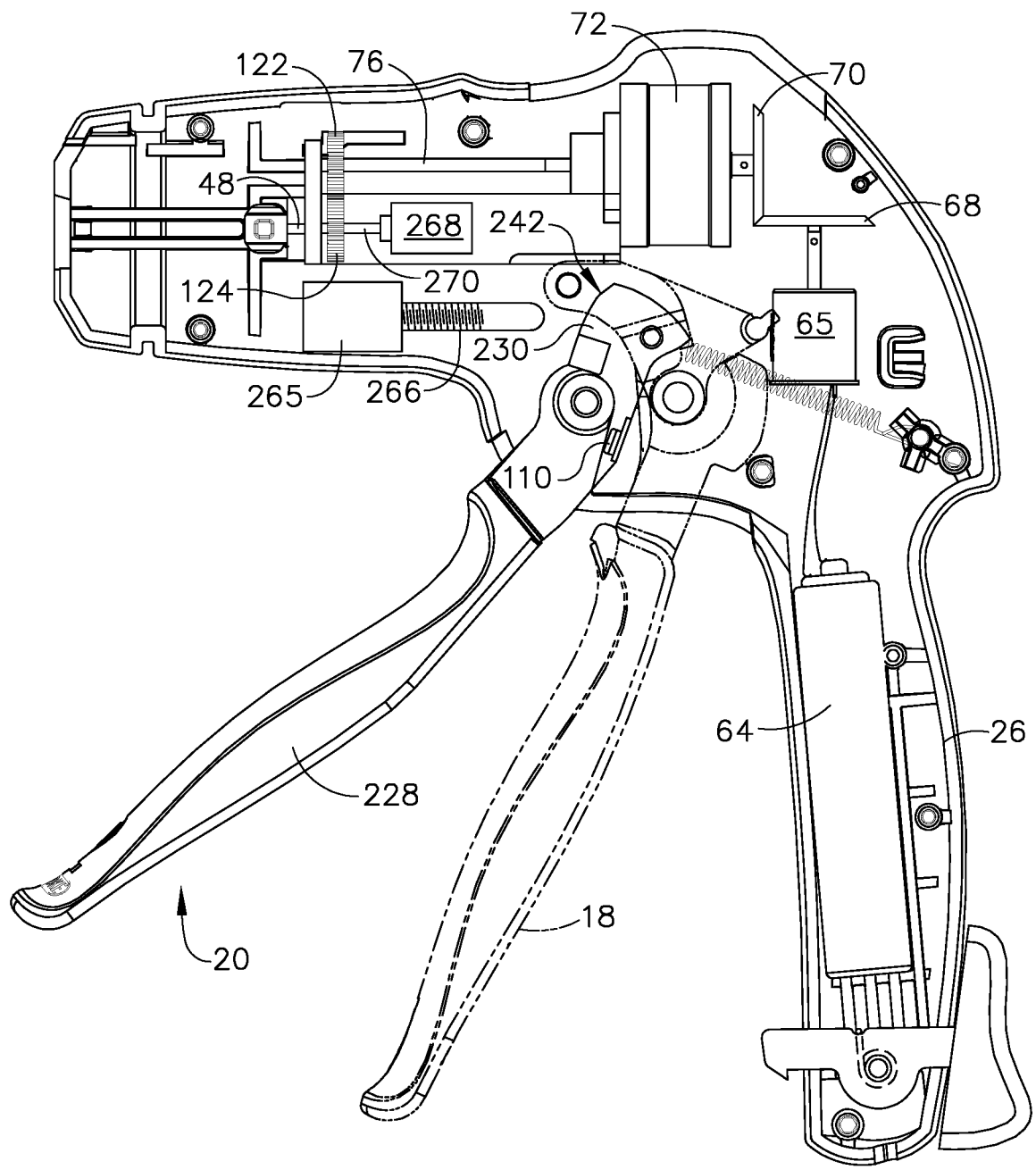
FIGS. 37-40 illustrate a surgical cutting and fastening instrument with tactile feedback according to various embodiments.
Figure 38:
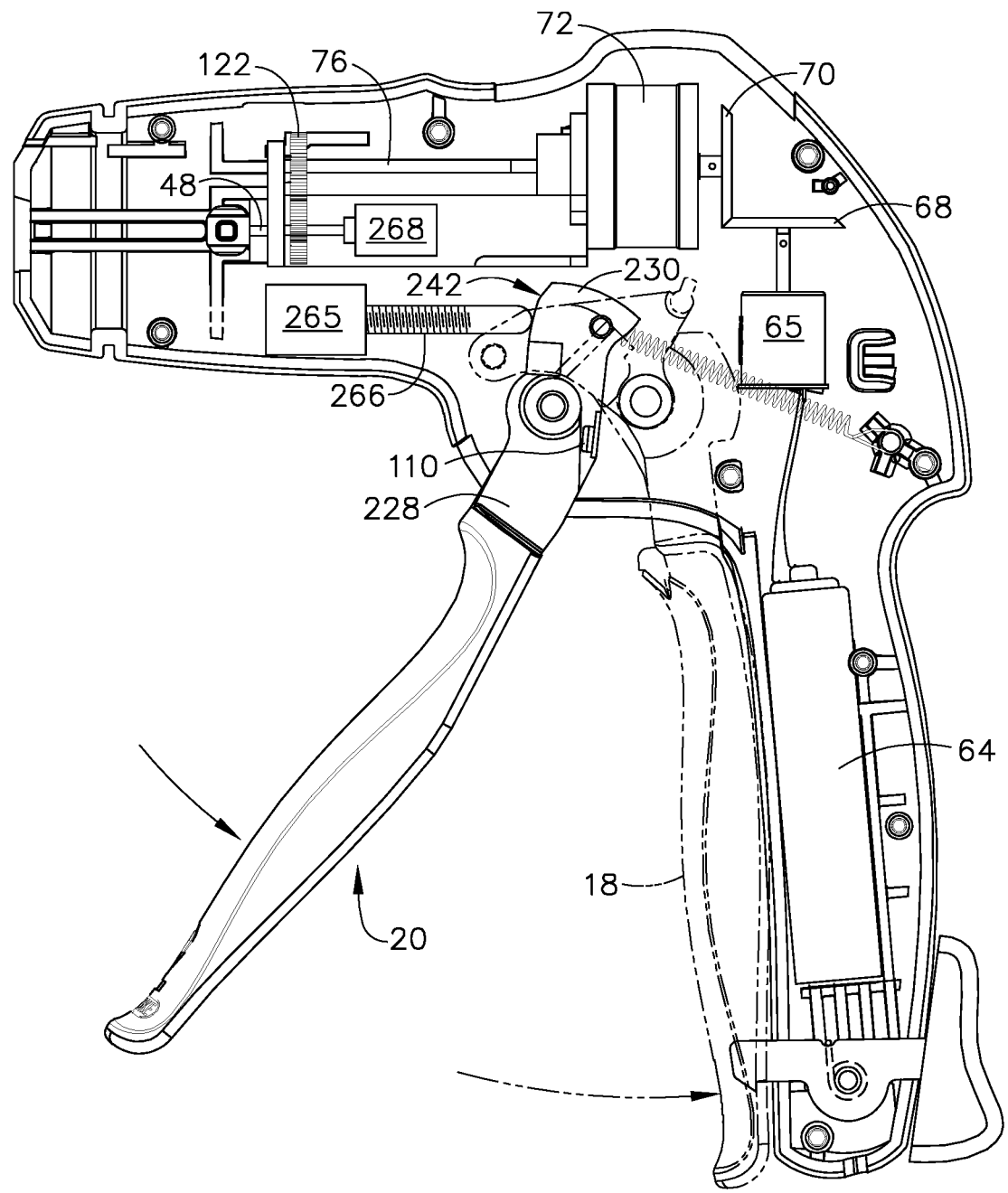
Figure 39:
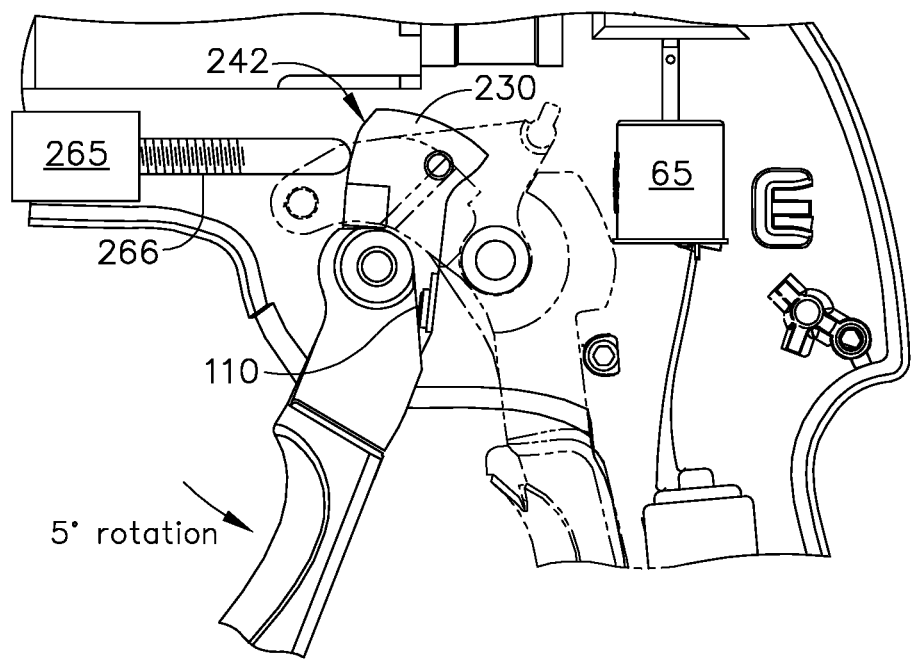
Figure 40:
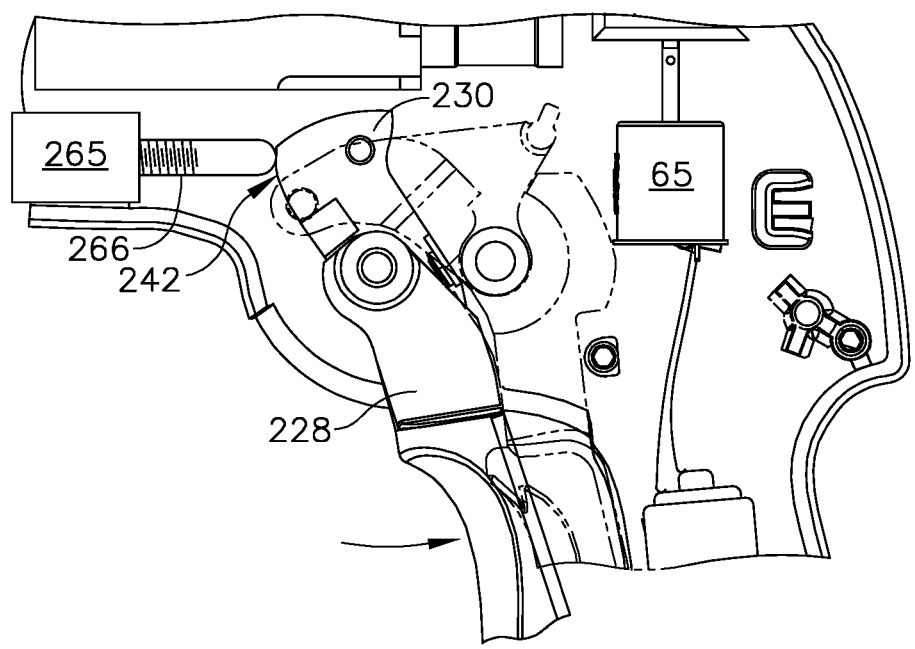

In operation, as shown in FIG. 37, when the closure trigger 18 is not locked into the clamped position, the firing trigger 20 rotated away from the pistol grip portion 26 of the handle 6 such that the front face 242 of the upper portion 230 of the firing trigger 20 is not in contact with the proximate end of the threaded rod 266. When the operator retracts the closure trigger 18 and locks it in the clamped position, the firing trigger 20 rotates slightly towards the closure trigger 20 so that the operator can grasp the firing trigger 20, as shown in FIG. 38. In this position, the front face 242 of the upper portion 230 contacts the proximate end of the threaded rod 266.

As the user then retracts the firing trigger 20, after an initial rotational amount (e.g., 5 degrees of rotation) the run motor sensor 110 may be activated such that, as explained above, the sensor 110 sends a signal to the motor 65 to cause it to rotate at a forward speed proportional to the amount of retraction force applied by the operator to the firing trigger 20. Forward rotation of the motor 65 causes the main drive shaft 48 to rotate via the gear drive train, which causes the knife 32 and sled 33 to travel down the channel 22 and sever tissue clamped in the end effector 12. The control circuit receives the output signals from the encoder 268 regarding the incremental rotations of the main drive shaft assembly and sends a signal to the second motor 265 to caused the second motor 265 to rotate, which causes the threaded rod 266 to retract into the motor 265. This allows the upper portion 230 of the firing trigger 20 to rotate CCW, which allows the lower portion 228 of the firing trigger to also rotate CCW. In that way, because the reciprocating movement of the threaded rod 266 is related to the rotations of the main drive shaft assembly, the operator of the instrument 10, by way of his/her grip on the firing trigger 20, experiences tactile feedback as to the position of the end effector 12. The retraction force applied by the operator, however, does not directly affect the drive of the main drive shaft assembly because the firing trigger 20 is not geared into the gear drive train in this embodiment.

By virtue of tracking the incremental rotations of the main drive shaft assembly via the output signals from the encoder 268, the control circuit can calculate when the knife 32 is fully deployed (i.e., fully extended). At this point, the control circuit may send a signal to the motor 65 to reverse direction to cause retraction of the knife 32. The reverse direction of the motor 65 causes the rotation of the main drive shaft assembly to reverse direction, which is also detected by the encoder 268. Based on the reverse rotation detected by the encoder 268, the control circuit sends a signal to the second motor 265 to cause it to reverse rotational direction such that the threaded rod 266 starts to extend longitudinally from the motor 265. This motion forces the upper portion 230 of the firing trigger 20 to rotate CW, which causes the lower portion 228 to rotate CW. In that way, the operator may experience a CW force from the firing trigger 20, which provides feedback to the operator as to the retraction position of the knife 32 in the end effector 12. The control circuit can determine when the knife 32 is fully retracted. At this point, the control circuit may send a signal to the motor 65 to stop rotation.

According to other embodiments, rather than having the control circuit determine the position of the knife 32, reverse motor and stop motor sensors may be used, as described above. In addition, rather than using a proportional sensor 110 to control the rotation of the motor 65, an on/off switch or sensor can be used. In such an embodiment, the operator would not be able to control the rate of rotation of the motor 65. Rather, it would rotate at a preprogrammed rate.

In various embodiments, as described above, a motor can be utilized to advance a cutting member and/or staple-driving sled distally within an end effector of a surgical instrument. In at least one such embodiment, as also described above, the motor can be utilized to retract the cutting member and/or sled proximally. In some circumstances, however, the motor may be incapable of generating or supplying a sufficient force, or torque, to retract the cutting member and/or sled. Such circumstances may arise when the motor becomes defective or when the cutting member becomes stuck within the end effector. Other such circumstances may arise when the battery, or other suitable power source, supplying the motor cannot provide sufficient power to the motor. In any event, various embodiments of the present invention can comprise a manual return system which can be utilized to retract the cutting member and/or sled, for example. In certain circumstances, such manual return systems can be referred to as "bail-out mechanisms". In various embodiments, a manual return mechanism can be configured to operably disengage, or disconnect, the motor from the cutting member and/or sled at the same time, prior to, and/or after the manual return mechanism is operably engaged with the cutting member and/or sled. In at least one such embodiment, as a result, the cutting member and/or sled can be retracted without interference from a broken motor and/or a dysfunctional motor attempting to advance the cutting member and/or sled, for example.

Figure 43:
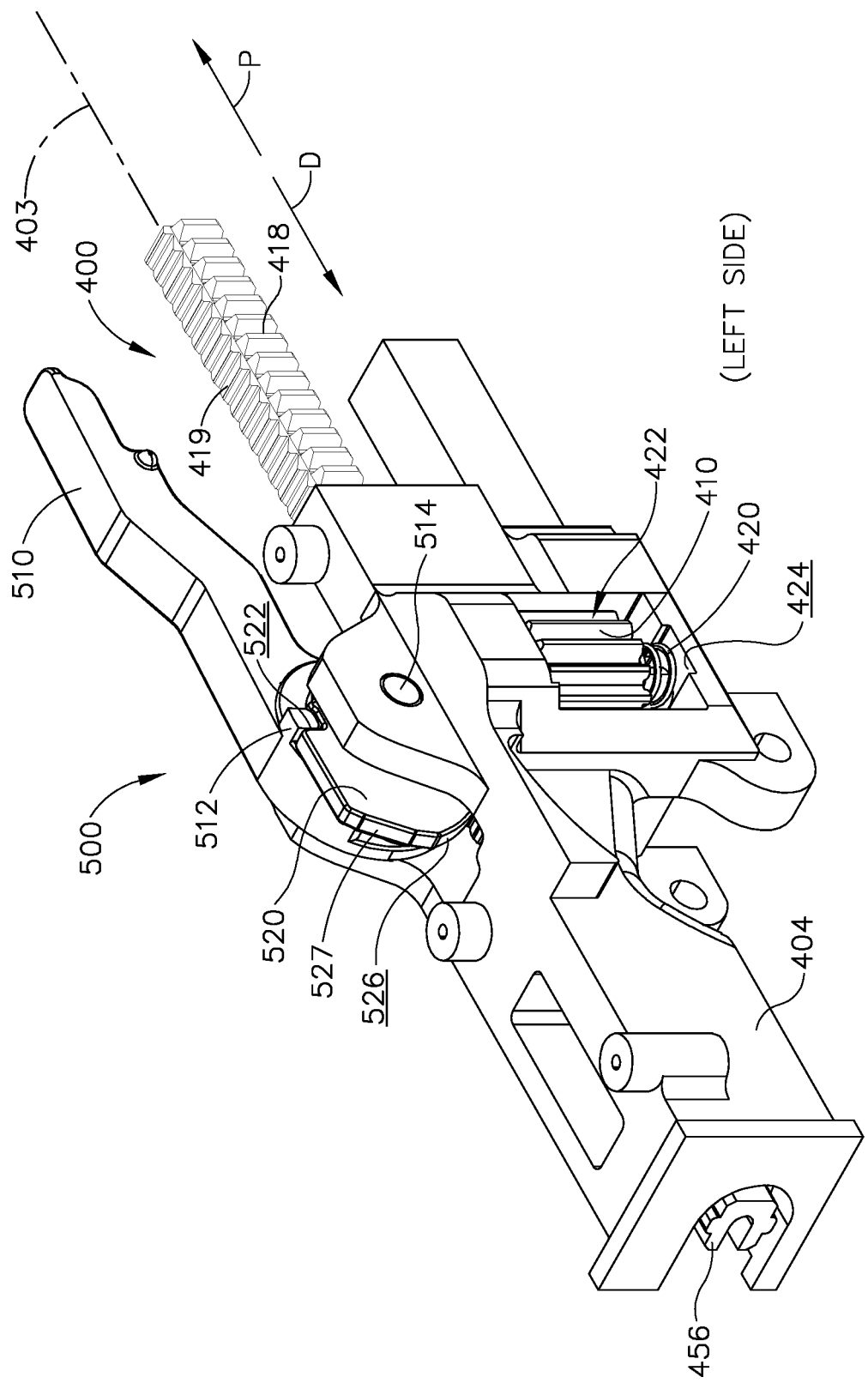
FIG. 43 is a perspective view of a drive shaft and a manual return mechanism of a surgical cutting and fastening instrument according to various embodiments of the present invention.
Figure 46:
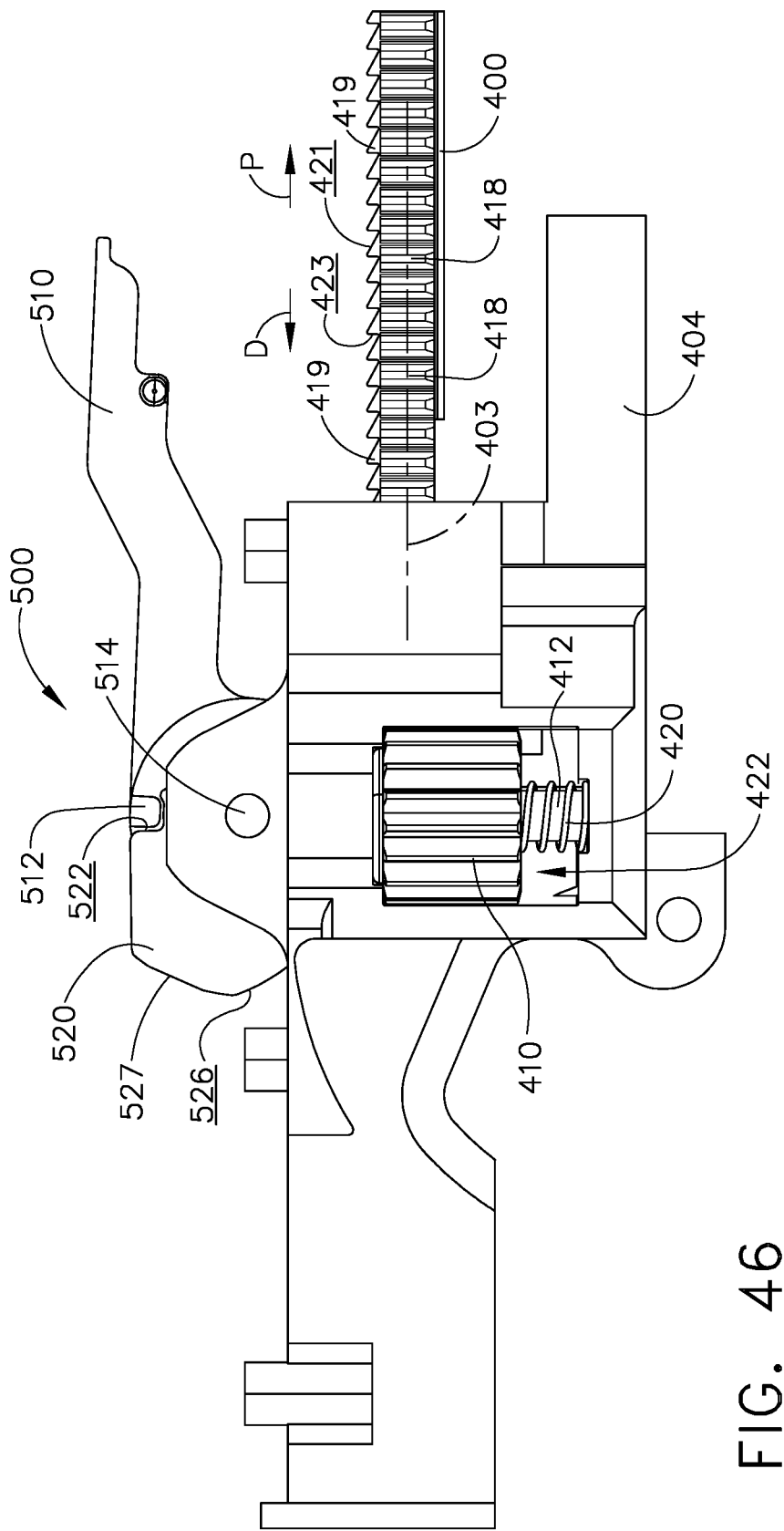
FIG. 46 is an elevational view of the drive shaft and the manual return mechanism of FIG. 43.
Figure 47:
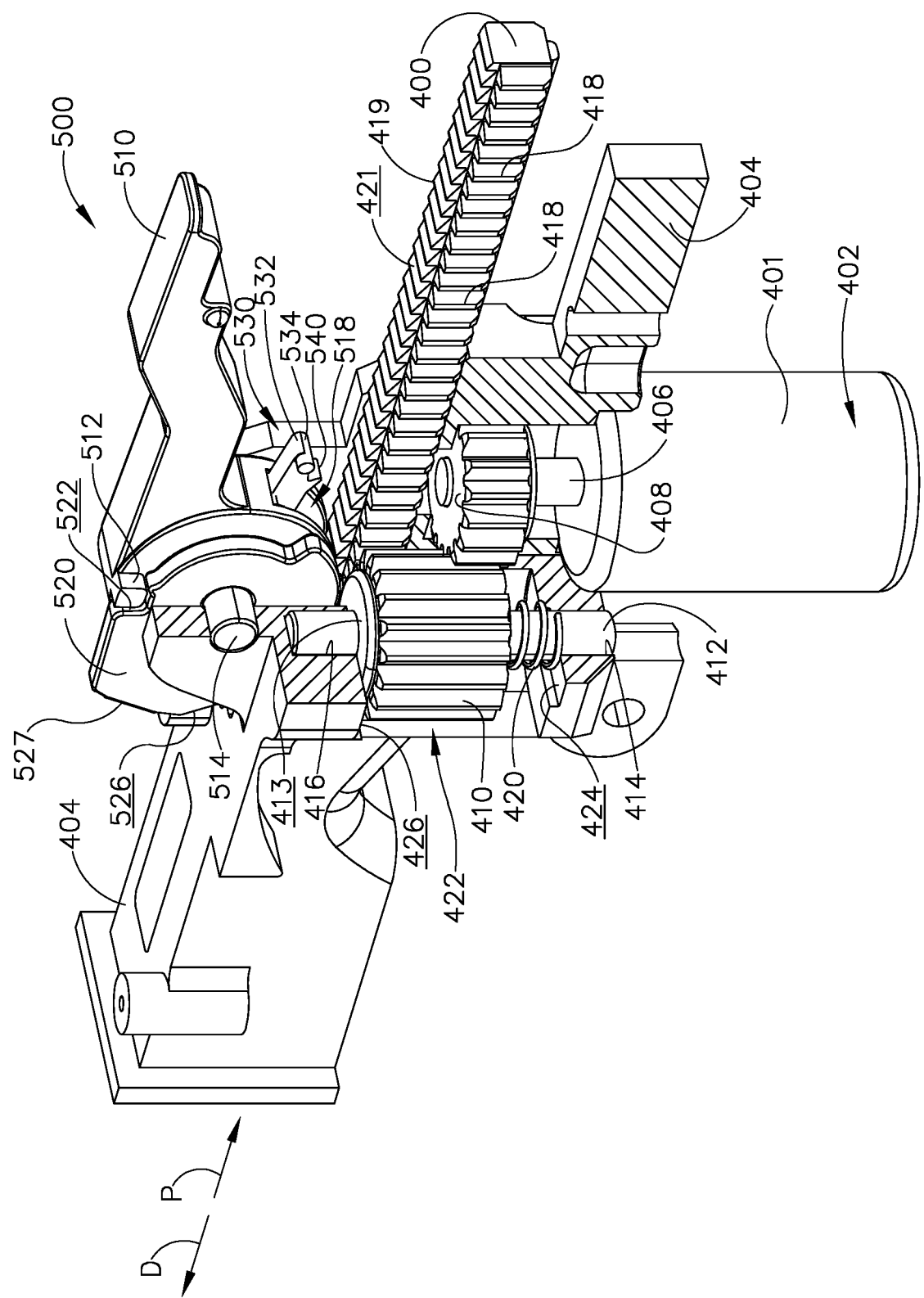
FIG. 47 is a partial cut-away view of the manual return mechanism of FIG. 43 and an electric motor operably engaged with the drive shaft.

In various embodiments, referring to FIG. 43, a surgical instrument, such as a surgical stapler, for example, can include a firing rod, or drive shaft, 400 which can be advanced and/or retracted by a motor, such as electrical motor 402 depicted in FIG. 47, for example. In at least one such embodiment, referring again to FIG. 47, motor 402 can be mounted to, or mounted relative to, frame 404 such that there is no, or at least little, relative movement between frame 404 and motor housing 401. Electrical motor 402 can be configured to receive electrical energy supplied thereto and convert at least a portion of such electrical energy to mechanical energy. In at least one embodiment, electrical motor 402 can be configured to rotate rod 406 and drive gear 408. In certain embodiments, drive gear 408 can be integrally formed with rod 406 or, alternatively, drive gear 408 can be sufficiently or fixedly attached to rod 406 such that the rotation of rod 406 can be transmitted to drive gear 408. In at least one such embodiment, drive gear 408 can include an aperture therein which can be configured to receive rod 406 in a press-fit relationship, for example. In various embodiments, although not illustrated in FIGS. 43-53, a surgical instrument can include a firing trigger, such as firing trigger 20 (FIG. 1), for example, which, when actuated, can allow electrical current to flow to motor 402 and supply motor 402 with electrical power. In certain embodiments, as described above, the surgical instrument can include a battery which can be placed in electrical communication with motor 402 when the trigger is actuated.

Figure 44:
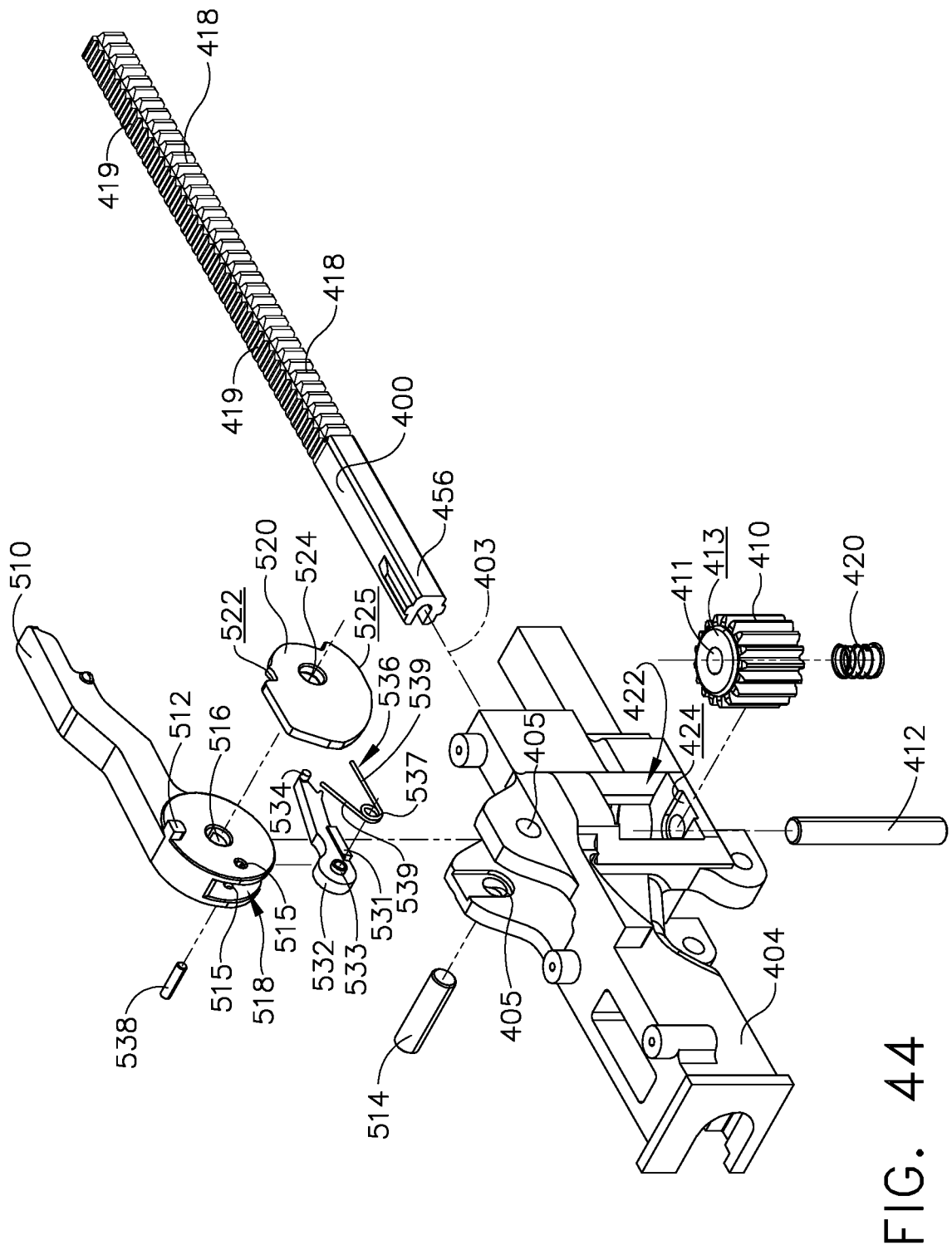
FIG. 44 is an exploded view of the drive shaft and the manual return mechanism of the surgical cutting and fastening instrument of FIG. 43.
Figure 45:
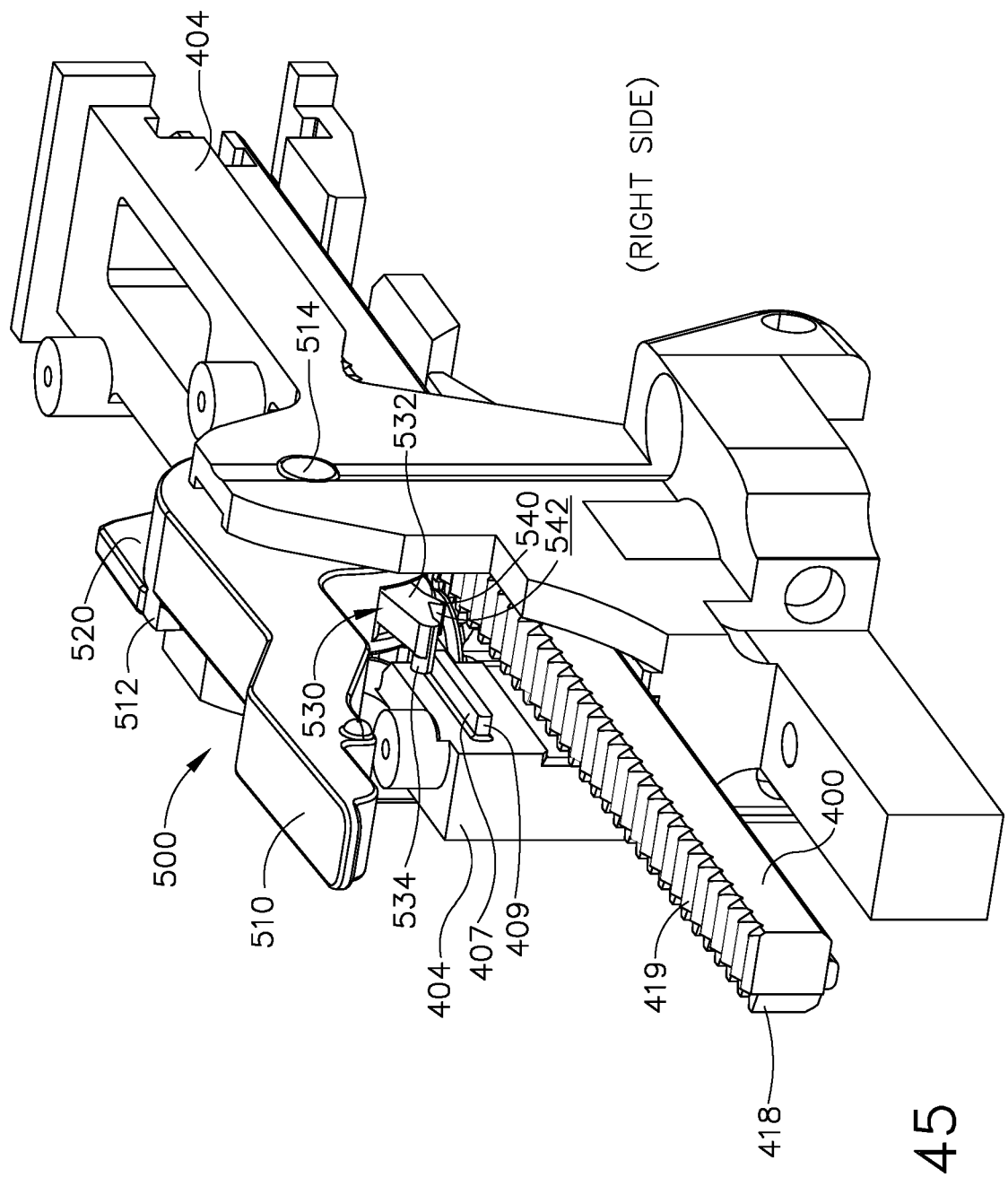
FIG. 45 is another perspective view of the drive shaft and the manual return mechanism of FIG. 43.

In various embodiments, referring again to FIG. 47, drive gear 408 can be operably engaged with pinion gear 410 such that the rotation of drive gear 408 can be transmitted to pinion gear 410. In at least one such embodiment, pinion gear 410 can include teeth which can be meshingly engaged with the teeth of drive gear 408. As illustrated in FIG. 44, pinion gear 410 can include an aperture 411 extending therethrough, or at least partially therethrough, which can be configured to receive pin 412. In at least one such embodiment, although not illustrated, aperture 411 and pin 412 can be sized and configured to permit pinion gear 410 to rotate relative to pin 412 wherein aperture 411 can be configured to closely receive pin 412 such that pin 412 can define an axis about which pinion gear 410 can rotate. In various alternative embodiments, referring again to FIG. 47, pinion gear 410 can be integrally formed with or fixedly mounted to pin 412 such that rotation of pinion gear 410 is transmitted to pin 412. In at least one such embodiment, pin 412 can be press-fit within aperture 411 of pinion gear 410. In certain embodiments, frame 404 can include apertures 414 and 416 which can each be configured to closely receive a portion of pin 412 such that apertures 414 and 416 can define an axis about which pin 412, and pinion gear 410, can rotate.

In certain embodiments, pin 412 can be slidably received within apertures 414 and 416 such that, as described in greater detail below, pinion gear 410 can be selectively engaged and disengaged with drive shaft 400. For the present purposes, though, the arrangement of the surgical instrument as depicted in FIG. 47 depicts pinion gear 410 in operative engagement with drive shaft 400. The various circumstances in which pinion gear 410 may be operatively disengaged from drive shaft 400 will be addressed further below. Referring primarily to FIGS. 43-47, pinion gear 410 can be operably engaged with drive shaft 400 such that the rotation of drive gear 408 can be transmitted to drive shaft 400. In at least one embodiment, drive shaft 400 can include a first rack portion comprising a plurality of first drive teeth 418 which can be configured to be meshingly engaged with the teeth of pinion gear 410 such that the rotation of pinion gear 410 can translate, or displace, drive shaft 400 along a predetermined path. For example, referring to FIGS. 43-47, pinion gear 410 can be configured to move shaft 400 distally along axis 403 in a direction indicated by arrow D and/or proximally along axis 403 in a direction indicated by arrow P, depending on the direction in which drive gear 408, and correspondingly pinion gear 410, are rotated by motor 402. Although the predetermined path can be linear, or at least substantially linear, other embodiments are envisioned in which a drive shaft can be moved along a non-linear path such as a curved, and/or curvi-linear, path, for example.

Referring to FIGS. 46 and 47, a surgical instrument can further include pinion spring 420 which can be configured to bias pinion gear 410 into operative engagement with first drive teeth 418. In various embodiments, the frame 404 can include a pinion gear chamber 422 that can comprise, among other things, a first surface 424 and a second surface 426 between which pinion gear 410 can be positioned. In at least one embodiment, referring to FIG. 47, pinion spring 420 can be positioned intermediate, or compressed between, pinion gear 410 and first surface 424 of chamber 422 such that spring 420 can bias pinion gear 410 against second surface 426 of chamber 422. In certain embodiments, as a result, second surface 426 can provide a datum against which pinion gear 410 can be positioned such that the teeth of pinion gear 410 can be aligned with the first teeth 418 of drive shaft 400, at least until pinion gear 410 is disengaged from drive shaft 400 as described in greater detail below. When pinion gear 410 is positioned against second surface 426, for example, the teeth of pinion gear 410 can be operably engaged with both drive gear 408 and drive shaft 400. Accordingly, motor 402 can be operably engaged with drive shaft 400 via gears 408 and 410 in order to advance drive shaft 400 in direction D and/or retract drive shaft 400 in direction P, for example.

Figure 52:
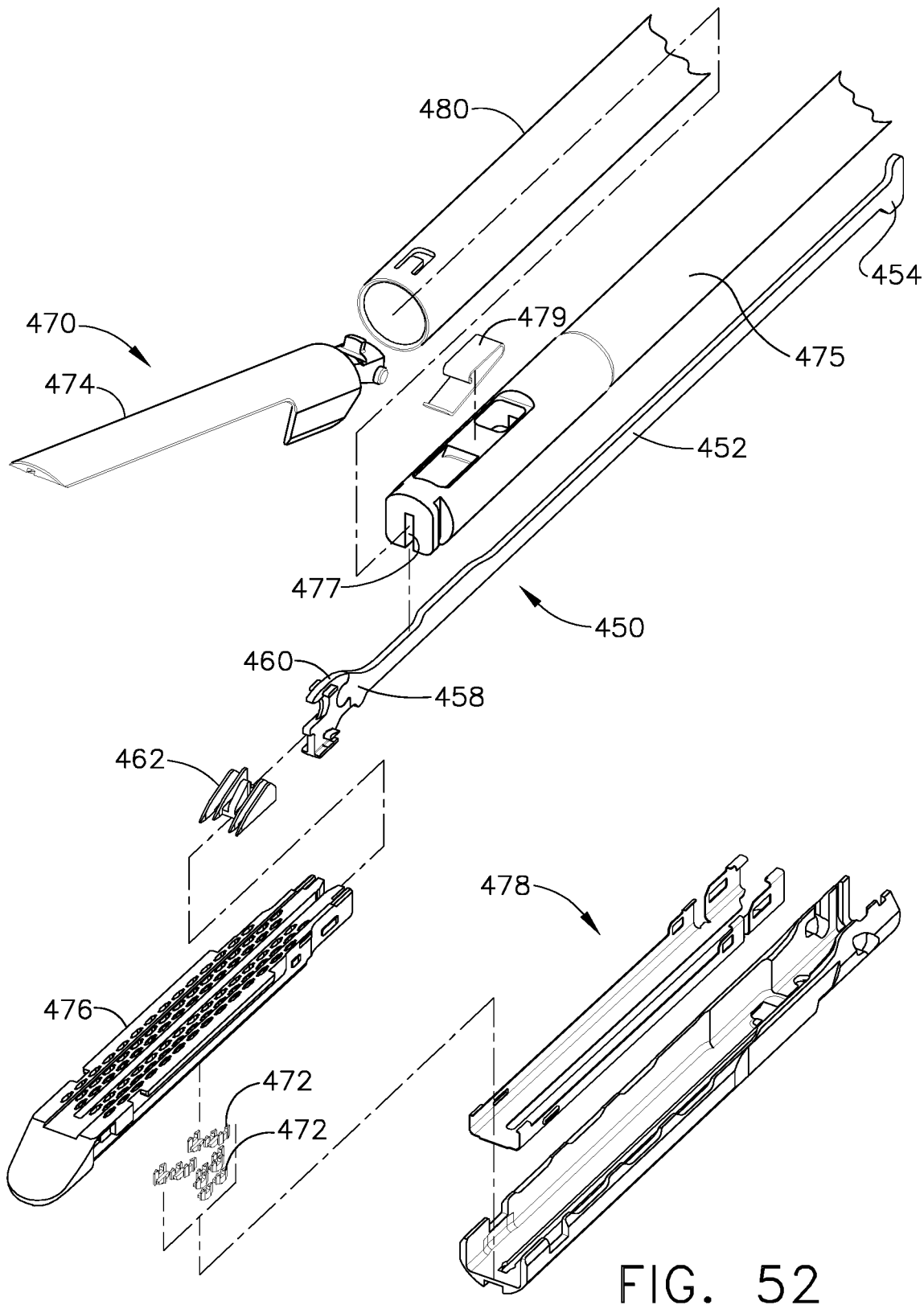
FIG. 52 is an exploded view of an end effector in accordance with an embodiment of the present invention, the end effector including a knife bar configured to be operably coupled with the drive shaft of FIG. 43.
Figure 53:
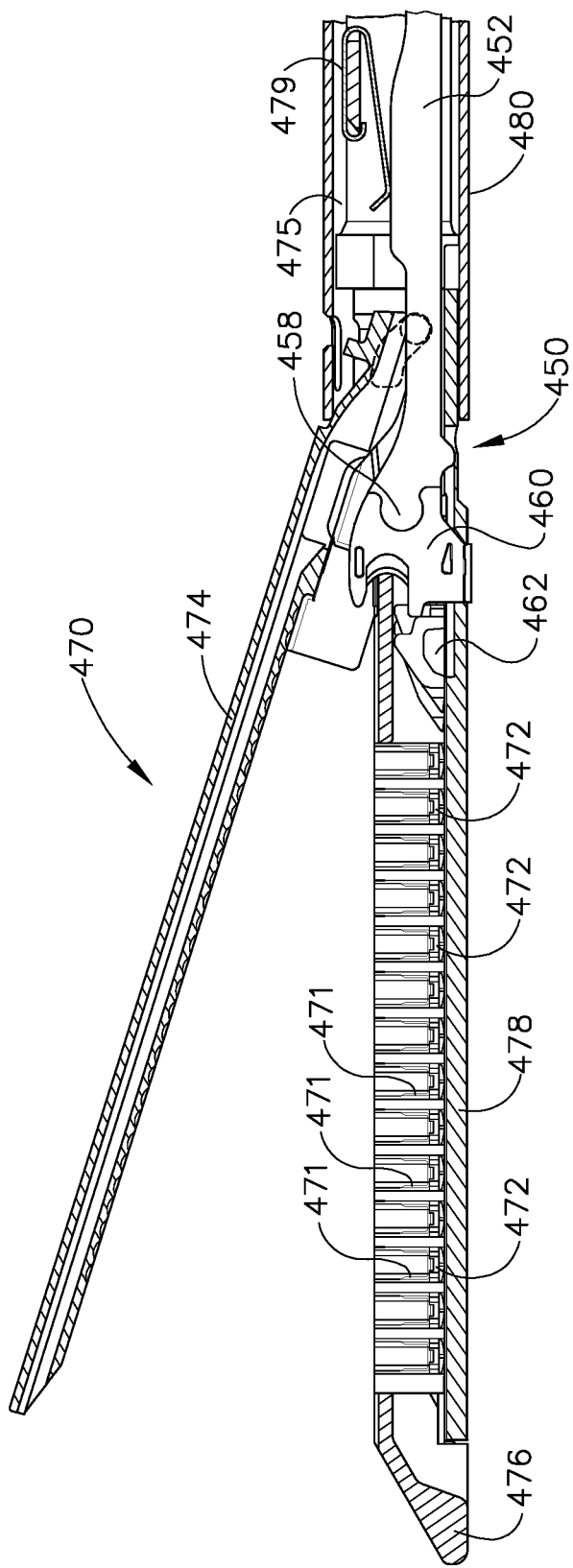
FIG. 53 is a cut-away view of the end-effector of FIG. 52.

In various embodiments, referring to FIGS. 52 and 53, a surgical instrument can further include a knife bar assembly 450, for example, which can be operably coupled with drive shaft 400 such that, when drive shaft 400 is moved by motor 402 as described above, drive shaft 400 can move knife bar assembly 450. In at least one embodiment, knife bar assembly 450 can include a knife bar, or drive bar, 452 having a proximal end 454 connected to distal end 456 of drive shaft 400 either directly and/or by a coupling member (not illustrated). In at least one such embodiment, the surgical instrument can further include spine 475 which can be configured to slidably receive and/or support drive bar 452 within slot 477. In certain embodiments, knife bar assembly 450 can further include cutting instrument 460 operably engaged with distal end 458 of drive bar 452 such that cutting instrument 460 can be moved in a proximal, distal, and/or any other suitable direction relative to end effector 470. In various embodiments, knife bar assembly 450 can further include staple-driving sled 462 that can be advanced in a proximal, distal, and/or any other suitable direction by cutting instrument 460, for example, and can engage drivers 472 supporting staples 471 (FIG. 53) stored within staple cartridge 476. Similar to the above, end-effector 470 can further include staple cartridge channel 478 which can be configured to retain and support staple cartridge 476. In any event, a surgical instrument can further include a spring 479 configured to bias anvil 474 into an open position and, in addition, a closure tube 480 which can be configured to position and hold anvil 474 in a closed position such that anvil 474 can deform staples 471 as they are deployed from staple cartridge 476.

In use, as described above, drive shaft 400 and drive bar 452 can be advanced distally and retracted proximally by motor 402 in order to advance and retract one, or both, of cutting member 460 and/or sled 462 within end-effector 470. In the event, however, that one or more of drive shaft 400, drive bar 452, cutting instrument 460, sled 462, and/or any other portion of the drive, or firing, system becomes stuck, broken, or is otherwise unable to be sufficiently or fully retracted, a manual return system can be utilized to drive one or more of drive shaft 400, drive bar 452, and cutting instrument 460 proximally, for example. In certain embodiments, motor 402 can be operably disengaged from drive shaft 400 before, during, and/or after the engagement of the return system with drive shaft 400, for example. In various embodiments, motor 402 can be disengaged from drive shaft 400 as the manual return system is engaged with drive shaft 400. In at least one embodiment, such an arrangement may assure that the motor does not resist or prevent drive shaft 400, for example, from being driven distally by the return system. In certain embodiments, drive shaft 400, drive bar 452, cutting instrument 460, and/or sled 462 can be operably connected such that, if a retraction force is applied to one or more of these members, the retraction force can be transmitted to one or more of the other members such that they can be retracted together.

In various embodiments, referring to FIG. 44, a return system 500 can include a lever, or handle, 510 and a cam 520, wherein lever 510 can be configured to move cam 520. In at least one embodiment, referring to FIG. 48, lever 510 can be rotated in a first direction, represented by arrow 1, in order to move cam 520 between a first position (FIG. 48) and a second position (FIG. 49). In various embodiments, referring to FIG. 44, lever 510 can be rotatably mounted to frame 404 by pivot pin 514, wherein pivot pin 514 can define an axis about which lever 510 can be rotated. In at least one such embodiment, lever 510 can further include aperture 516 which can be aligned with apertures 405 in frame 404 to permit pin 514 to be inserted therethrough. In various embodiments, pin 514 and one or more apertures 405 can be configured such that there is a snug fit, or even press-fit, therebetween in order to prevent, or at least inhibit, pin 514 from sliding out of apertures 405 and 516. Although not illustrated, one or more fasteners can be utilized to retain pin 514 within apertures 405 and 516. In any event, lever aperture 516 can be sized and configured such that there is sufficient clearance between the sidewalls of aperture 516 and pin 514 to permit sliding movement therebetween yet limit, or prevent, translation therebetween. In at least one alternative embodiment, lever 510 can be mounted to pin 514 such that pin 514 can rotate with lever 510. In certain embodiments, referring to FIG. 48 once again, lever 510 can include cam driver 512 extending therefrom which can be configured to engage at least a portion of cam 520, such as a drive surface, or drive pocket, 522 and rotate cam 520 in the first direction (indicated by arrow 1) when lever 510 is rotated in the first direction. In at least one embodiment, referring once more to FIG. 44, cam 520 can be rotatably mounted to frame 404 by pin 514 which, similar to lever 510, can be inserted through cam aperture 524 and define an axis about which cam 520 can be rotated.

Figure 48:
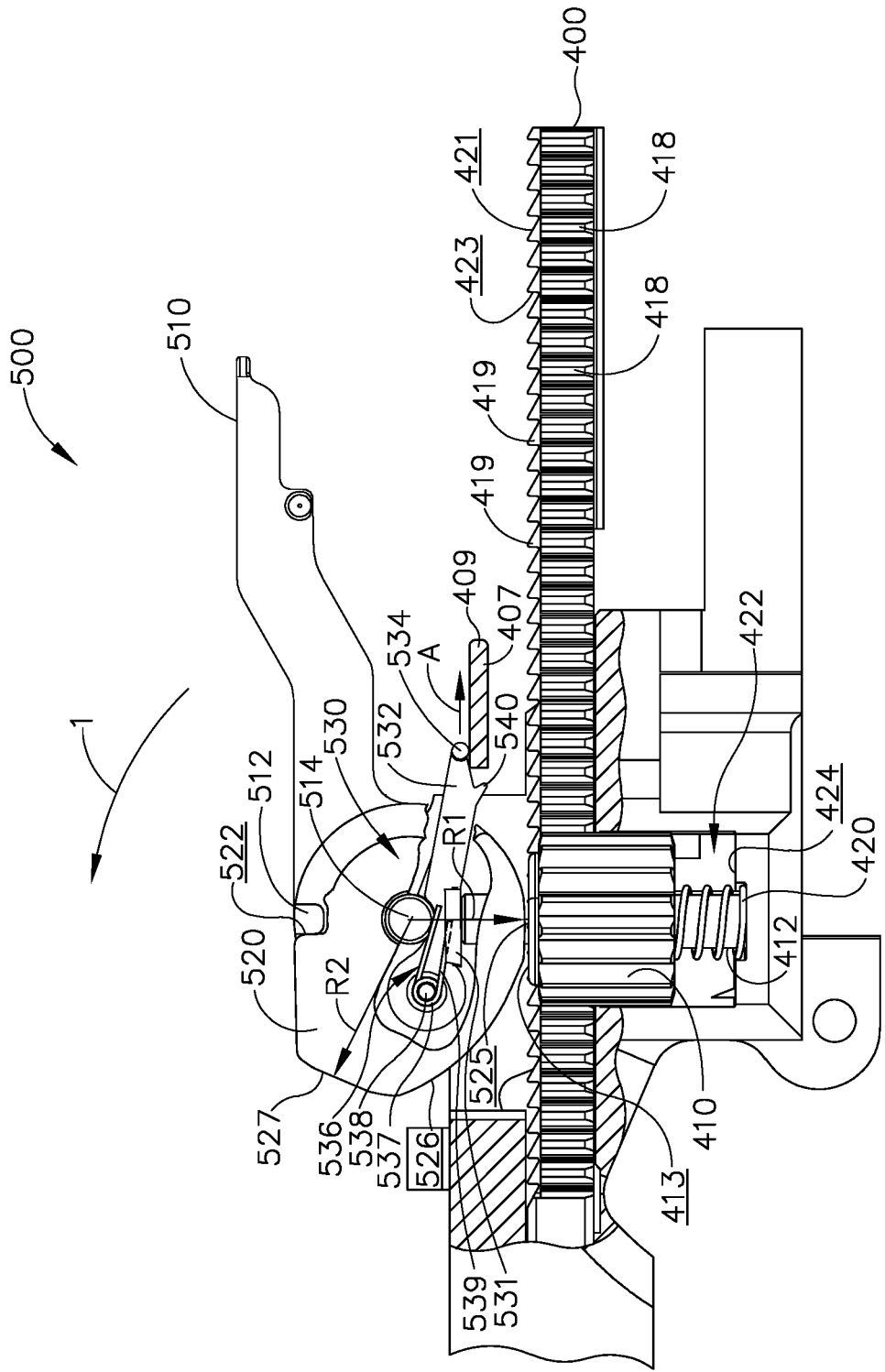
FIG. 48 is another partial cut-away view of the manual return mechanism of FIG. 43 illustrating a lever, a cam in a first position, and a pawl pivotably mounted to the lever where the pawl is being held in a disengaged position.
Figure 49:
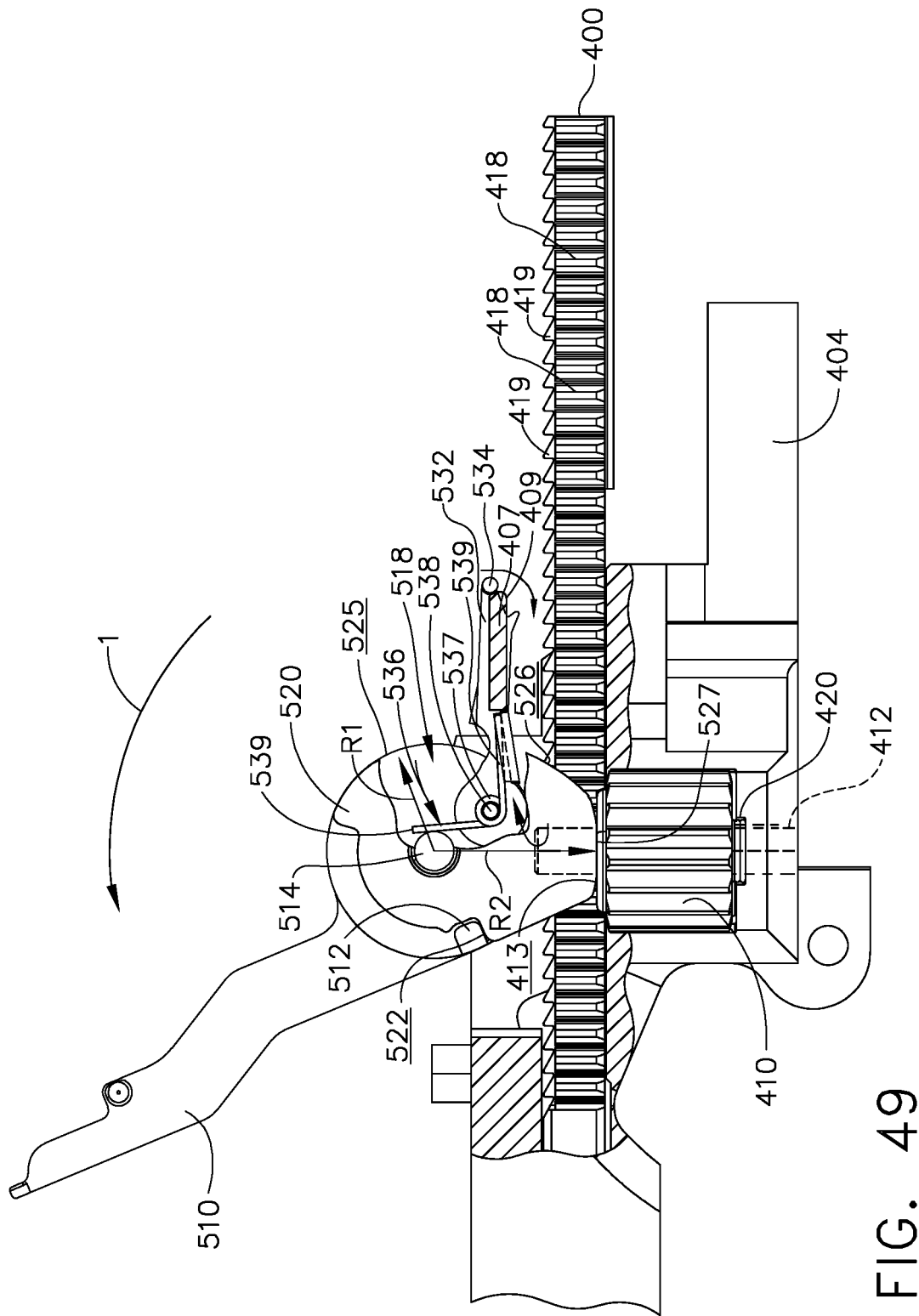
FIG. 49 is another partial cut-away view of the manual return mechanism of FIG. 43 illustrating the lever rotated in a first direction, the cam nearly in a second position, and the pawl on the verge of being moved into an engaged position with the drive shaft by a pawl spring.

In various embodiments, referring to FIG. 48, cam 520 can include first cam surface 525 which can be positioned and configured to permit spring 420 to bias gear 410 into engagement with drive shaft 400 when cam 520 is in its first position as illustrated in FIG. 48. In at least one embodiment, first cam surface 525 can be configured such that there is clearance between cam 520 and pinion gear 410 when cam 520 is in its first position. As cam 520 is rotated into its second position by lever 510, as described above and referring to FIG. 49, a portion of cam 520 can contact pinion gear 410 and move pinion gear 410 out of engagement with drive shaft 400. More particularly, in at least one embodiment, cam 520 can include second cam surface 526 which, when in it comes into contact with surface 413 of pinion gear 410, can force or move pinion gear 410 toward first surface 424 in pinion gear chamber 422 and, correspondingly, compress spring 420. In various embodiments, cam surfaces 525 and 526 can define one or more arcuate and/or linear contours, or profiles, which can permit relative sliding movement between cam 520 and pinion gear 410. In at least one such embodiment, cam surface 526, for example, can define a profile in which the distance, or radius, between cam surface 526 and the axis of pin 514 can gradually increase between first cam surface 525 and stop point 527. In various embodiments, stop point 527 can define the end of second cam surface 526 and/or the furthest point on second cam surface 526 which contacts pinion gear 410. In certain embodiments, referring to FIGS. 48 and 49, cam surface 526 can be at least partially defined by a first radius of curvature R1 and a second radius of curvature R2, wherein R2 can be larger than R1. In at least one embodiment, R1 and R2 can be selected such that the net difference between R1 and R2, or throw, can be sufficient to displace pinion gear 410 such that pinion gear 410 is no longer operably engaged with drive shaft 400 when cam 520 is in its second position and/or stop point 527 of cam 520 is in contact with surface 413 of pinion gear 410.

In various embodiments, when lever 510 is moved in the first direction (arrow 1) to rotate cam 520 between its first (FIG. 48) and second (FIG. 49) positions by lever 510 as described above, lever 510 can move retraction pawl assembly 530 into engagement with drive shaft 400. Referring to FIG. 48, which illustrates lever 510 before it is moved in the first direction, retraction pawl assembly 530 is illustrated as being held out of engagement with drive shaft 400. More particularly, referring to FIG. 45, pawl 532 of pawl assembly 530 is illustrated as being held in a disengaged position by ledge 407 extending from frame 404. In certain embodiments, still referring to FIG. 45, pawl 532 can include projection 534 extending therefrom which can be configured to slide along ledge 407. In at least one such embodiment, referring again to FIG. 48, pawl 532 can be slid in a proximal direction along ledge 407, indicated by arrow A, when lever 510 is rotated in the first direction. At, or near, the same time as cam 520 is rotated into its second position as illustrated in FIG. 49, projection 534 can slide off of end 409 of ledge 407. In various embodiments, retraction pawl assembly 530 can further include pawl spring 536 which can be configure to bias pawl 532 into engagement with drive shaft 400 when projection 534 has slid off of, or cleared, end 409 of ledge 407. In such an embodiment, the retraction pawl 532 can be engaged with drive shaft 400 at the same time, or at least nearly the same time, as pinion gear 410 is disengaged from drive shaft 400. In various alternative embodiments, ledge 407 can be configured such that projection 534 slides off of, or clears, ledge 407 prior to, and possibly just prior to, cam 520 being fully rotated into its second position and pinion gear 410 being completely disengaged from drive shaft 400. Alternatively, projection 534 can slide off of, or clear, ledge 407 after, and possibly just after, cam 520 is full rotated into its second position and pinion gear 410 is disengaged from shaft 400. In any event, the disengagement of the motor 402 from drive shaft 400 and the engagement of pawl assembly 530 with drive shaft 400 can allow drive shaft 400 to be retracted without resistance or interference from motor 402.

As described above, pawl 532 can be pivoted into engagement with drive shaft 400. In various embodiments, referring to FIGS. 49 and 50, pawl assembly 530 can further include pivot pin 538 which can be configured to pivotably mount pawl 532 within slot 518 in lever 510. In at least one embodiment, referring to FIG. 44, pivot pin 538 can be inserted into pin apertures 515 in lever 510 and aperture 533 in pawl 532 in order to rotatably retain pawl 532 to lever 510 and define an axis about which pawl 532 can rotate. In certain embodiments, referring to FIGS. 44 and 48, pawl spring 536 can comprise a torsion spring, for example, which can include a central portion 537 positioned around pivot pin 538 and, in addition, legs 539 which can be configured to apply biasing, or compressive, forces against pin 514, and/or any other suitable portion of lever 510, and pawl 532 such that pawl 532 can be biased toward drive shaft 400. In at least one embodiment, referring to FIG. 44, pawl 532 can include channel 531 which can be configured to receive and/or capture a leg 539 of spring 536 such that the leg 539 does not slip relative to, or become operably disengaged from, pawl 532.

Figure 50:
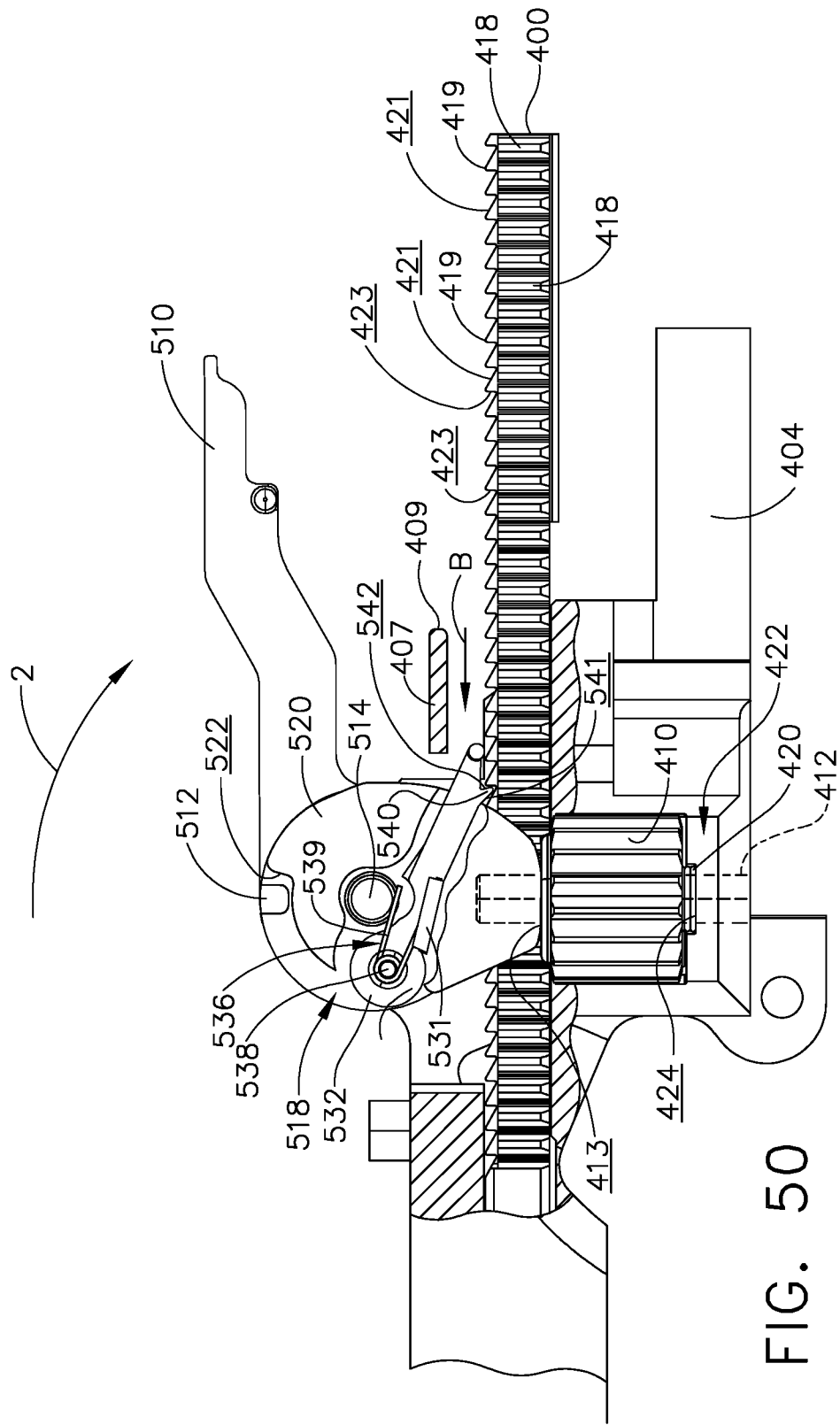
FIG. 50 is another partial cut-away view of the manual return mechanism of FIG. 43 illustrating the lever rotated in a second direction which is opposite the first direction, the cam still in its second position, and the pawl being slid along a plurality of teeth on the drive shaft.
Figure 51:
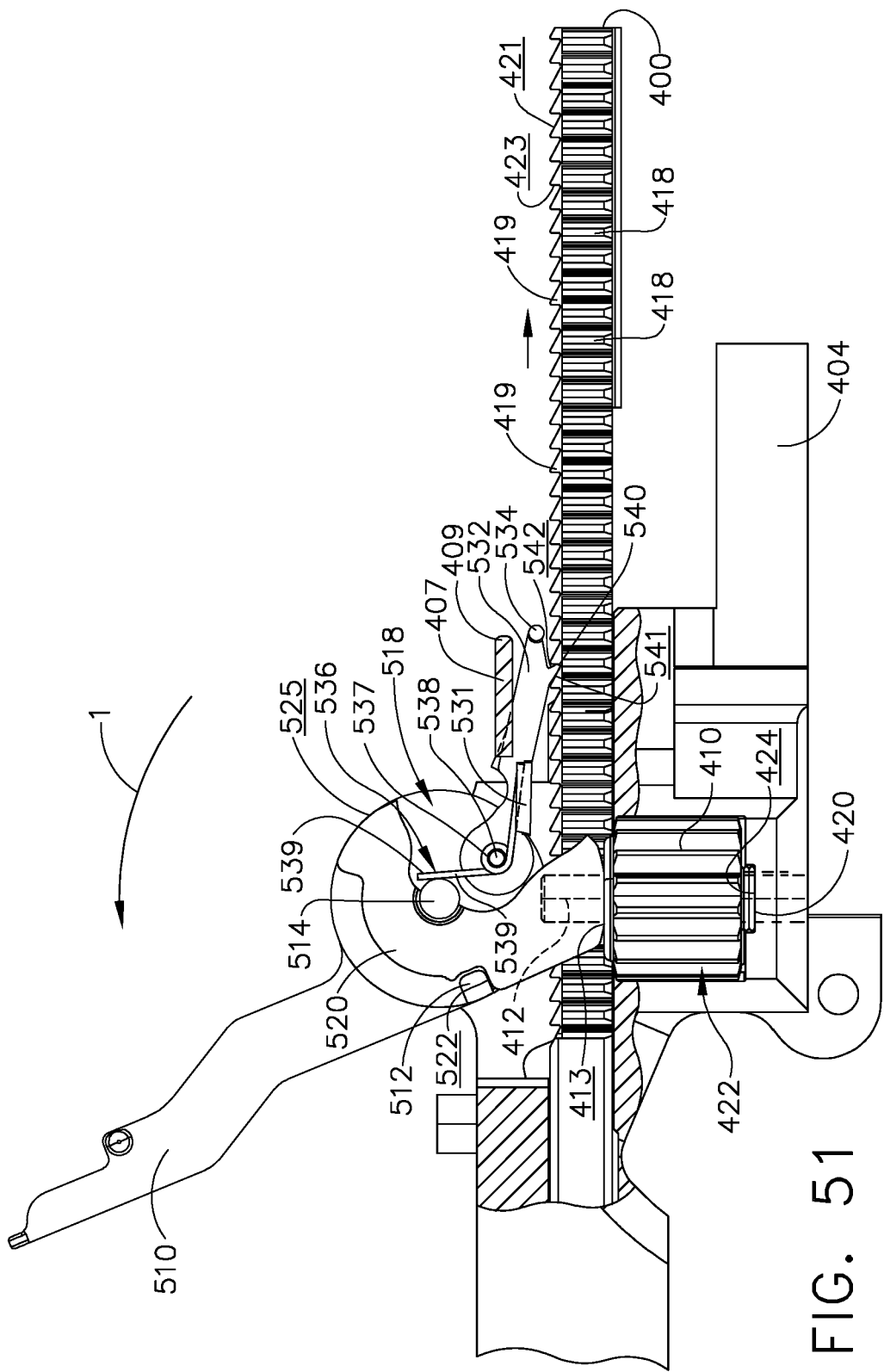
FIG. 51 is another partial cut-away view of the manual return mechanism of FIG. 43 illustrating the lever rotated in the first direction once again, the cam still in its second position, and the pawl being used to retract the drive shaft.

In any event, once pawl 532 has been slid off of, or has cleared, ledge 407, lever 510, referring to FIG. 50, can be rotated in a second direction, indicated by arrow 2, which is opposite the first direction. When lever 510 is rotated in the second direction, lever 510 can pull pawl 532 distally in a direction indicated by arrow B. In various embodiments, as illustrated in FIG. 50, lever 510 can pull pawl 532 such that it is slid over a plurality of second drive teeth 419 extending from drive shaft 400. In at least the illustrated embodiment, second drive teeth 419 can be positioned on a different side of drive shaft 400 than first drive teeth 418, although other various arrangements of the first and second drive teeth are envisioned which can place them on the same side or opposite sides of the drive shaft. In certain embodiments, the first and second drive teeth may comprise one set of teeth, or first and second portions of a set of teeth. In any event, pawl 532 can include one or more pawl teeth, such as pawl tooth 540, for example, which can be configured to slide over second drive teeth 419 when pawl 532 is moved in direction B. In various embodiments, referring to FIG. 50, pawl tooth 540 can include a first side 541 which can be configured to slide over the angled, or beveled, sides 421 of second teeth 419 without moving, or at least substantially moving, drive shaft 400 in a proximal and/or distal direction. When lever 510 is rotated in the first direction once again and pawl 532 is moved in a proximal direction as illustrated in FIG. 51, a second side 542 of pawl tooth 540 can engage a flat, or at least substantially flat, second side 423 of a second tooth 419. Once side 542 of pawl tooth 540 is engaged with side 423 of a second tooth 419, the proximal movement of pawl 532 can be transmitted to drive shaft 400 and move drive shaft 400 proximally. In embodiments where one or more of drive shaft 400, drive bar 452, cutting instrument 460, and/or sled 462, for example, are stuck, a surgeon can apply a force to lever 510 in order to dislodge the stuck component and retract drive shaft 400, drive bar 452, cutting instrument 460, and/or sled 462 in a proximal direction. In certain embodiments, only one stroke of lever 510 may be required to retract drive shaft 400 after pawl 532 has been engaged with drive shaft 400. In other embodiments, however, multiple strokes may be required. In such embodiments, lever 510 may be repeatedly moved in the first and second directions in order to ratchet drive shaft 400 proximally to a sufficient position.

In various embodiments, further to the above and referring to FIGS. 48-51, the initial rotation of lever 510 in the first direction (arrow 1) can set cam 520 in its second position and disengage pinion gear 410 from drive shaft 400 as described above. When lever 510 is then rotated in the second direction (arrow 2), however, cam 520 can remain in its second position. In at least one such embodiment, although cam driver 512 extending from lever 510 may be configured to abut drive surface 522 and move cam 520 from its first position (FIG. 48) into its second position (FIG. 49) as described above, cam driver 512 can be configured such it can be rotated away from drive surface 522 when lever 510 is rotated in the second direction. In such embodiments, as a result, lever 510 can thereafter be repeatedly moved in the first and second directions to retract drive shaft 400 while pinion gear 410 remains disengaged from drive shaft 400. In at least one such embodiment, once cam 520 has been rotated into its second position, it may not be possible to return cam 520 to its first position and/or move cam 520 into any other position. As a result, cam 520 may permanently hold out pinion gear 410 out of engagement with drive shaft 400. In various circumstances, such a feature may be useful as it is often the case that a manual return, or 'bail-out', system does not need to be used unless the surgical cutting and stapling instrument is defective in some manner. Such a feature could prevent the surgical instrument from being reused unless the surgical instrument is examined and reset by a qualified technician, for example.

Figure 54:
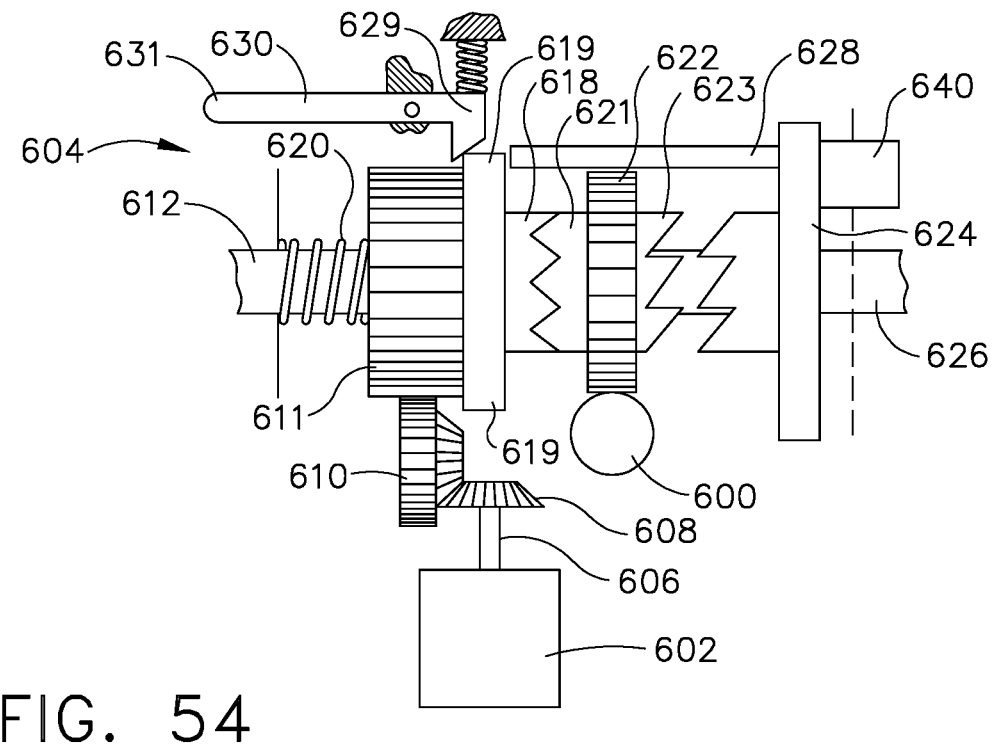
FIG. 54 is a diagram of a drive shaft and a manual return mechanism of a surgical cutting and fastening instrument according to alternative embodiments of the present invention illustrating an electric motor operably engaged with a drive shaft.

In certain embodiments, as described above, once a manual return, or 'bail-out', system has been operably engaged with a drive system, the manual return system may not be disengageable from the drive system and/or the drive system may otherwise be prevented from advancing a drive rod, for example, once again. In other various embodiments, the manual return system can be reset and the surgical instrument can be used once again. FIG. 54 is a diagram of a motor drive system and a portion of a manual return system of a surgical instrument in accordance with such an embodiment of the present invention. In at least one embodiment, the instrument can include drive shaft 600 which, similar to the above, can be configured to advance and/or retract a cutting instrument and/or staple-driving sled within an end effector, for example. Also similar to the above, as illustrated in FIG. 54, the instrument can include a motor 602 configured to rotate a drive gear 608 via a drive shaft 606. In various embodiments, drive gear 608 can be operably engaged with an intermediate gear 610 such that rotation of drive shaft 606 can be transmitted to intermediate gear 610. Although gears 608 and 610 can comprise spur gears, or gears similar to the gears illustrated in FIGS. 43-53, for example, gears 608 and 610 can comprise co-operating bevel gear portions, for example. Regardless of the type of gears used, intermediate gear 610 can include a portion configured to be operatively engaged with shaft gear 611. In various embodiments, shaft gear 611 can be freely rotated about shaft 612, although shaft 612 can be closely received within an aperture in shaft gear 611 such that shaft 612 can define an axis about which shaft gear 611 can be rotated. In certain embodiments, shaft gear 611 can be mounted to shaft 612 such that the rotation of intermediate gear 610 can be transmitted to shaft 612. As illustrated in FIG. 54, shaft 612 can be rotatably supported by frame 604 and/or any other suitable portion of the surgical instrument.

In various embodiments, further to the above, the drive system can further include motor crown gear 618 mounted to drive shaft 612 and/or shaft gear 611 such that the rotation of intermediate gear 610 can be transmitted to crown gear 618. In at least one embodiment, the drive system can further include spring 620 which can be configured to apply a biasing force to shaft gear 611, for example, such that one or more of shaft gear 611, shaft 612, and crown gear 618 can be biased toward central gear 622. When it is desirable to have motor 602 operatively engaged with drive shaft 600, for example, spring 620 can be permitted to push crown gear 618 into operative engagement with central gear 622. In at least one such embodiment, central gear 622 can include a crown gear portion 621 extending therefrom which can be configured to intermesh with crown gear 618. In embodiments where shaft gear 611 is slidably retained to shaft 612, central gear 622 can be fixedly mounted to shaft 612 and shaft 612 can be prevented, or at least inhibited, from sliding relative to frame 604. In at least one such embodiment, central gear 622 can be supported in position relative to drive shaft 600 by shaft 612.

Figure 55:
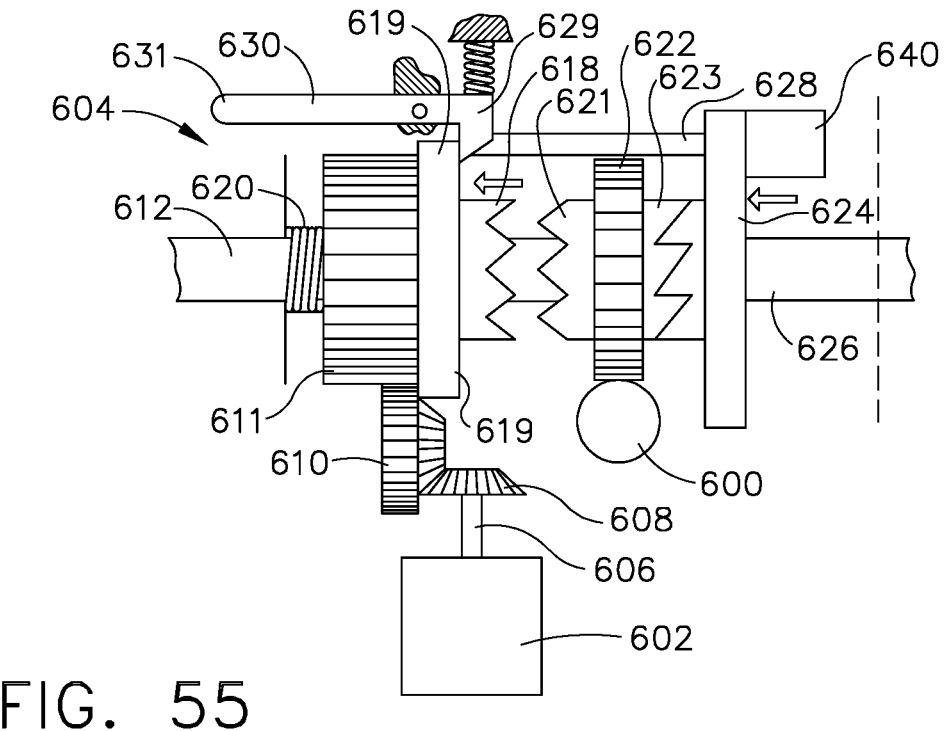
FIG. 55 is another diagram of the surgical instrument of FIG. 54 illustrating the manual return mechanism operably engaged with the drive shaft and the electric motor operably disengaged from the drive shaft.

Similar to the embodiments described above, circumstances may arise when it may be desirable to engage a manual return system with drive shaft 600. Also similar to the embodiments described above, it may also be desirable to operably disconnect motor 602 from drive shaft 600 when the manual return system is engaged therewith. In various embodiments, referring to FIG. 55, a lever (not illustrated) of the manual return mechanism can be moved, operated, or manipulated such that the lever can move lever crown gear 624 into engagement with central gear 622, or at least a crown gear portion 623 extending therefrom, and simultaneously, or at least substantially simultaneously, disengage motor crown gear 618 from central gear 622. In at least one embodiment, lever crown gear 624 can be slidably mounted to shaft portion 626 wherein, in at least one such embodiment, shaft portion 626 can comprise a portion of shaft 612. In various embodiments, lever crown gear 624 can include a cam surface, such as cam surface 640, for example, which can be engaged by a cam extending from the manual retraction lever, for example, such that a biasing force can be applied to lever crown gear 624 via cam surface 640. In at least one embodiment, push bar 628, which can also be mounted to lever crown gear 624 and/or slidably mounted to shaft 626, can be slid toward motor crown gear 618 until push bar 628 contacts a portion thereof. In certain embodiments, lever crown gear 624 and push bar 628 can be configured such that crown gear 624 is engaged with central gear 622 at, or near, the same time that crown gear 618 is pushed away from central gear 622.

In various embodiments, further to the above, the surgical instrument can further include a catch, or lock, 630 which can be configured to capture motor crown gear 618 when it is disengaged from crown gear 622 and, in addition, hold crown gear 618 in place as the manual return lever is used to drive crown gear 624 and central gear 622. In at least one such embodiment, lock 630 can include a hook 629, for example, which can be lifted upwardly when crown gear 618, or a rim 619 surrounding crown gear 618, contacts hook 629. In certain embodiments, hook 629 can snap over rim 619 owing to a biasing force applied to lock 630 by return spring 632. At some point, a surgeon may desire to re-engage motor 602 with drive shaft 600 and may push downwardly, for example, on end 631 of lock 630 such that lock 630 can pivot and, as a result, lift hook 629 upwardly and out of engagement with crown gear 618. At such point, spring 620 may expand and bias crown gear 618 into engagement with central gear 622 once again. Correspondingly, spring 620 may also apply a sufficient force to crown gear 618 in order to disengage or push crown gear 624 away from central gear 622 via push bar 628.

Figure 61:
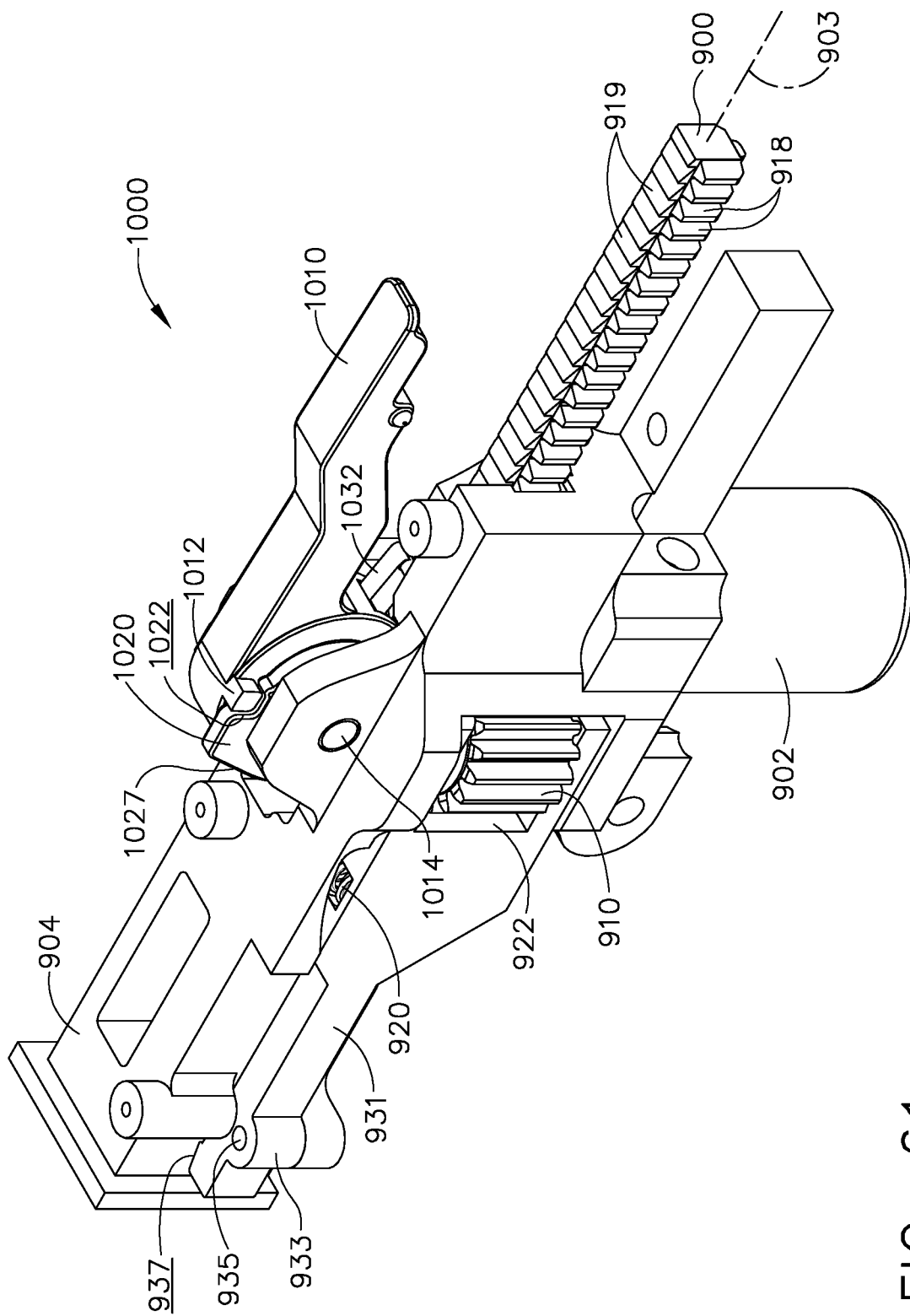
FIG. 61 is a perspective view of a drive shaft and a manual return mechanism of a surgical cutting and fastening instrument according to various embodiments of the present invention, the diagram illustrating a pinion gear rotatably supported by a swing arm wherein the pinion gear is operably engaged with a motor and the drive shaft.
Figure 62:
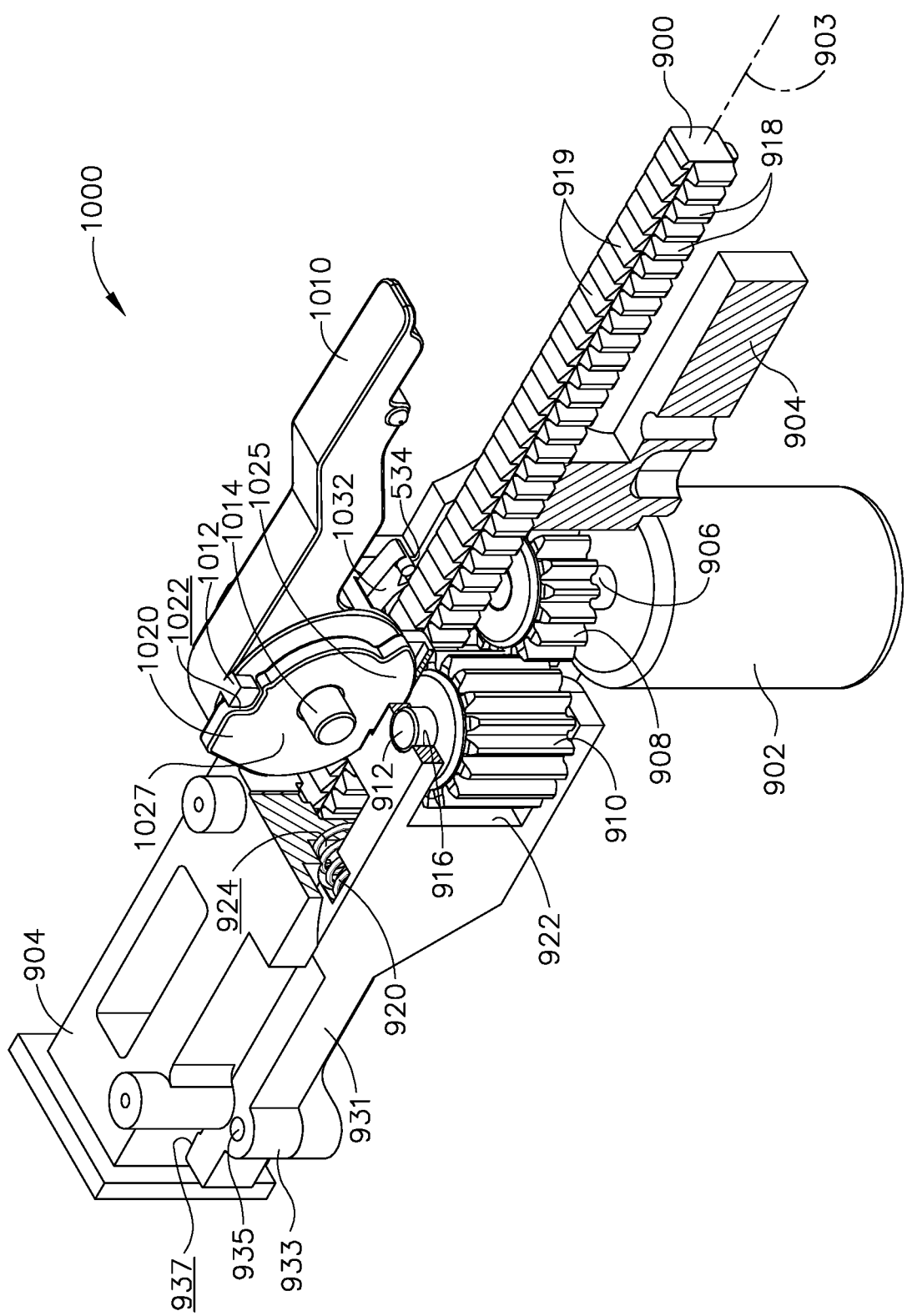
FIG. 62 is a partial cut-away view of the manual return mechanism of FIG. 61.
Figure 63:
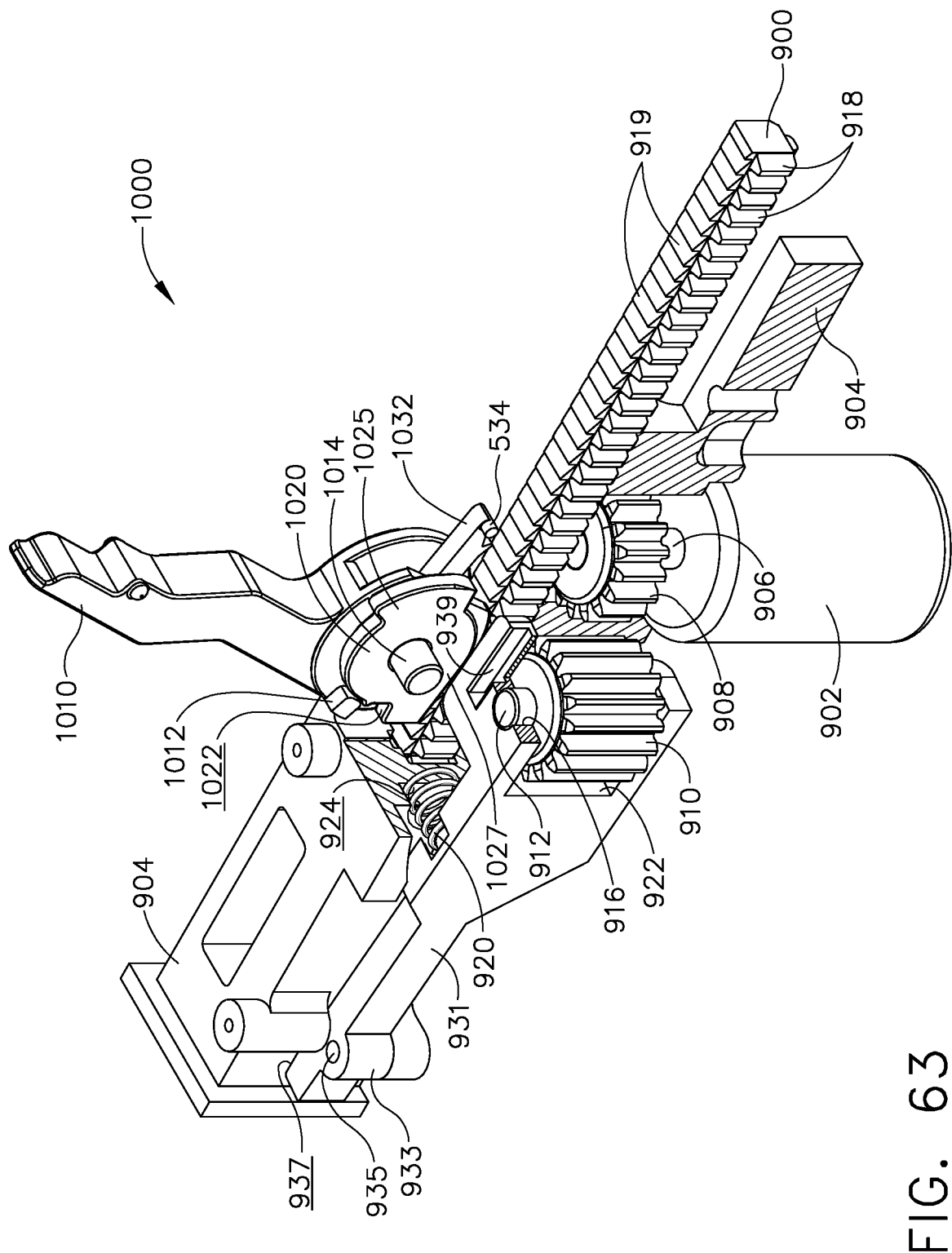
FIG. 63 is a partial cut-away view of the manual return mechanism of FIG. 61 illustrating a lever rotated in a first direction in order to disengage the lever from the swing arm and allow a spring to bias the pinion gear and the swing arm away from the drive shaft.
Figure 64:
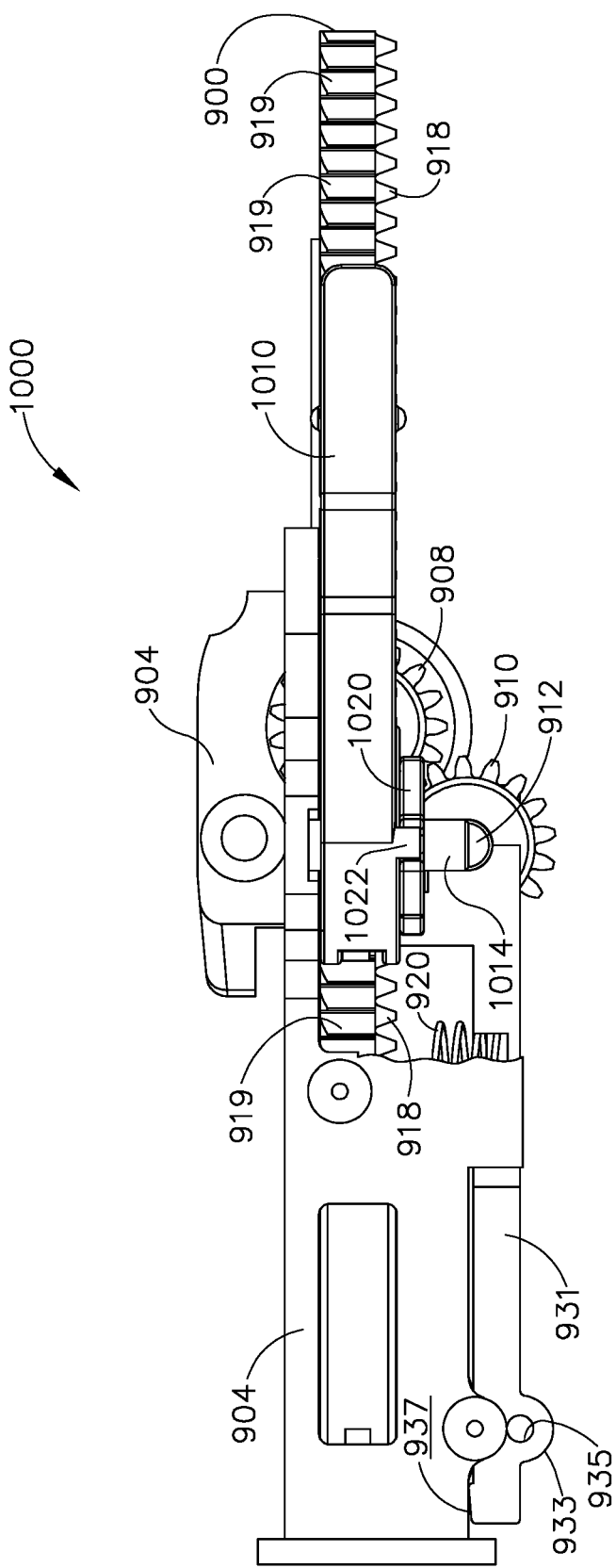
FIG. 64 is a top view of the drive shaft and the manual return mechanism of FIG. 61 illustrating the pinion gear engaged with the drive shaft and the motor.
Figure 65:
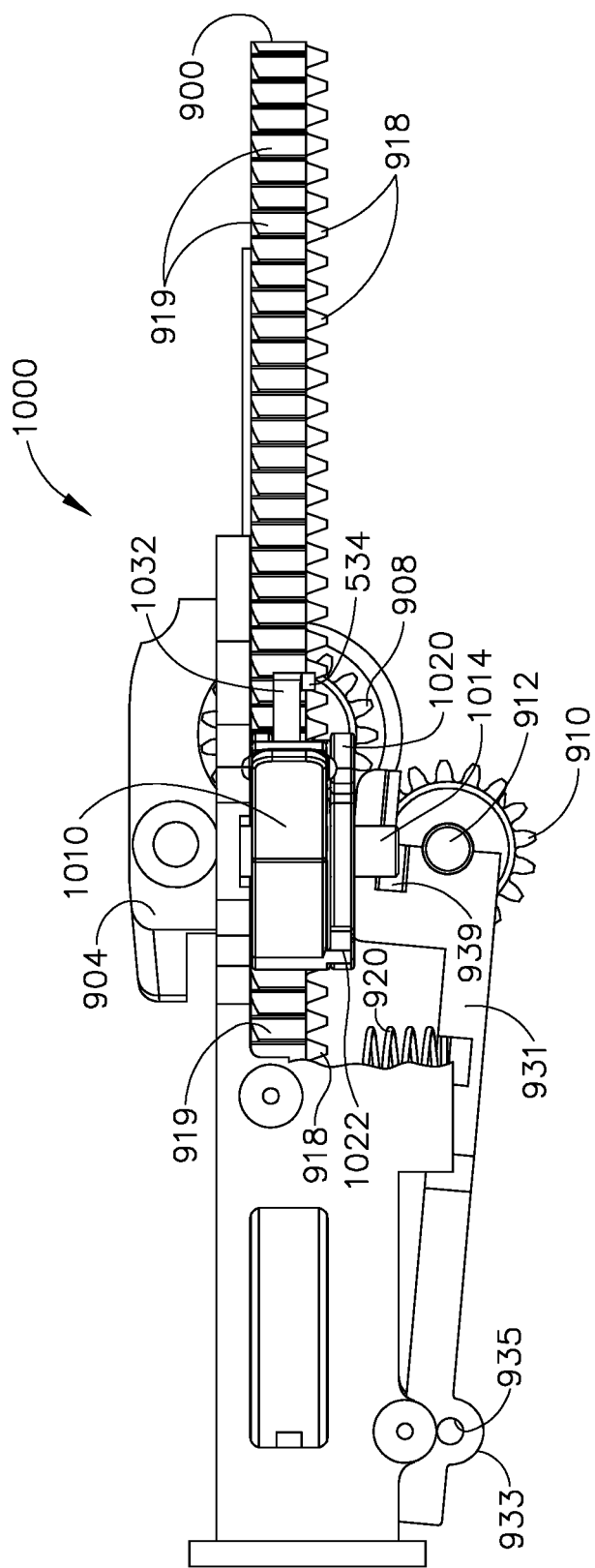
FIG. 65 is a top view of the drive shaft and the manual return mechanism of FIG. 61 illustrating the pinion gear disengaged from the drive shaft and the motor.
Figure 66:
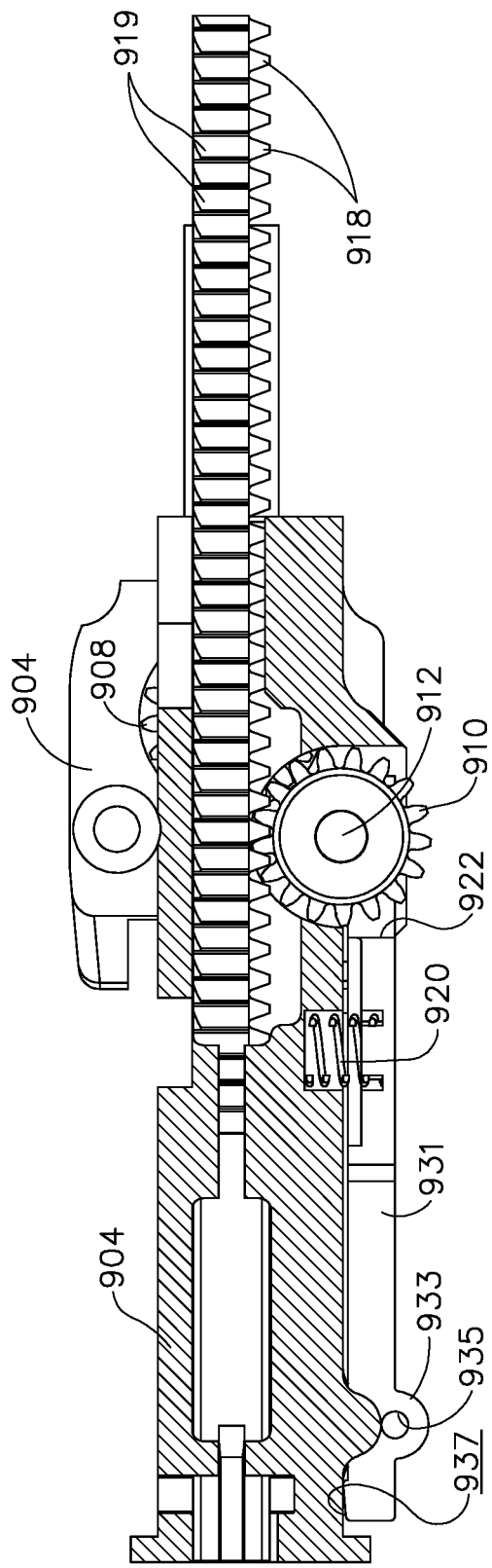
FIG. 66 is a partial cut-away view of the drive shaft and the manual return mechanism of FIG. 61 illustrating the pinion gear engaged with the drive shaft and the motor.
Figure 67:
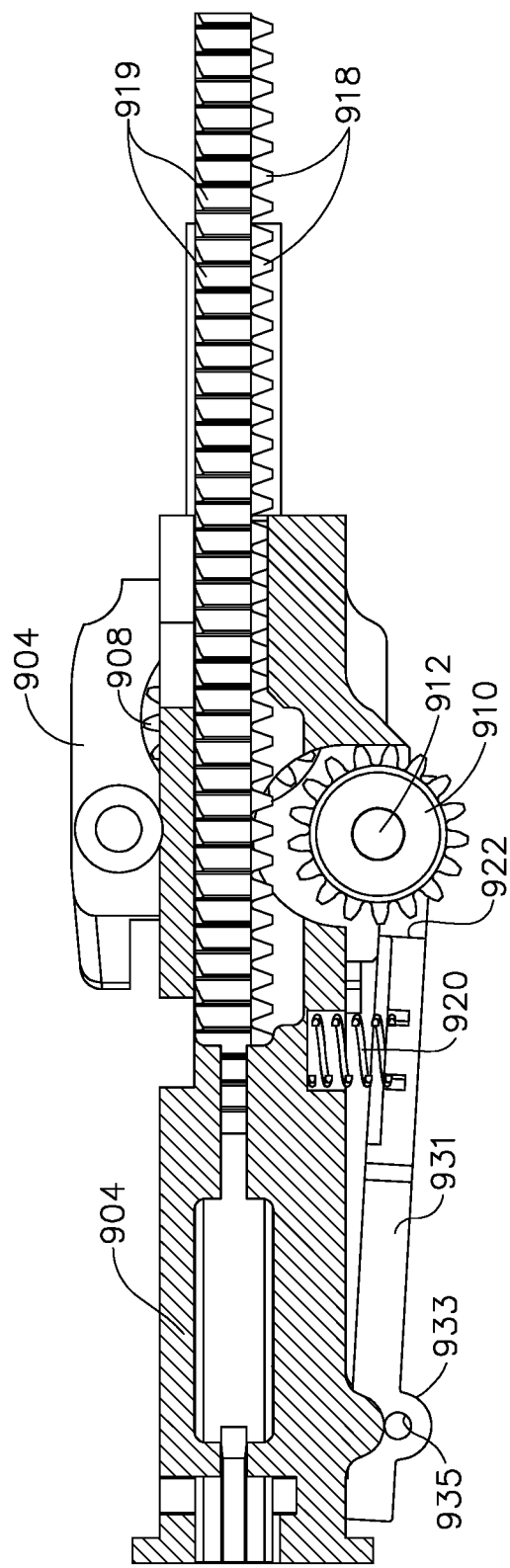
FIG. 67 is a partial cut-away view of the drive shaft and the manual return mechanism of FIG. 61 illustrating the pinion gear disengaged from the drive shaft and the motor.

In various embodiments, a surgical instrument can include a drive system and a manual return mechanism as illustrated in FIGS. 61-67, for example. Referring to FIGS. 61 and 62, the drive system can include a motor 902 configured to rotate motor drive shaft 906 and motor drive gear 908. In certain embodiments, the drive system can further include pinion gear 910 which can be selectively engaged with drive shaft 900 as described in greater detail below. In at least one embodiment, pinion gear 910 can be rotatably mounted to swing arm 931 via pin 912 and one or more pin apertures 916 such that, when swing arm 931 is in a first position as illustrated in FIG. 62, the teeth of pinion gear 910 can be meshingly engaged with the teeth of drive gear 908 and, in addition, first teeth 918 on drive shaft 900.

When swing arm 931 is in its first position, as a result, motor 902 can be configured to rotate drive gear 908 in a first direction so as to move drive shaft 900 in a distal direction along axis 903, for example, and, at other times, rotate drive gear 908 in a second direction so as to retract drive shaft 900 proximally, for example. In various embodiments, swing arm 931 can be selectively held in its first position and, in some embodiments, swing arm 931 can be releasably held in its first position by cam 1020. In at least one such embodiment, swing arm 931 can include a retention slot 939 configured to receive a least a portion of cam 1020 when cam 1020 is also in a first position as described in greater detail below.

Referring again to FIGS. 61-67, manual return mechanism 1000 can be selectively engaged with drive shaft 900 in order to manually retract drive shaft 900. In various embodiments, manual return mechanism 1000 can be similar in design and operation to manual return mechanism 500, for example, wherein manual return mechanism 1000 can include lever 1010 and pawl 1032 which can be configured to engage second teeth 919 on drive shaft 900 and retract drive shaft 900 proximally. A detailed disclosure of manual return mechanism 500, among others, is provided throughout the present application and the reader will appreciate that such disclosure can be applicable to the design and operation of manual return mechanism 1000. In at least one embodiment, lever 1010 can be rotated in a first direction from a first position, illustrated in FIG. 62, into a second position, illustrated in FIG. 63. When lever 1010 is moved in its first direction, lever 1010 can move pawl 1032 into engagement with second teeth 919 and, in addition, move cam 1020 between its first position, illustrated in FIG. 62, and a second position, illustrated in FIG. 63. In at least one embodiment, similar to the above, cam 1020 can include a drive surface 1022, for example, which can be contacted by a cam driver 1012, for example, extending from lever 1010 in order to rotate cam 1020 into its second position about an axis defined by pin 1014. When cam 1020 is rotated into its second position, cam 1020 can be disengaged from retention slot 939 in swing arm 931. More particularly, in at least one embodiment, cam 1020 can include a first portion 1025 which can be sized and configured to be received within retention slot 939 when cam 1020 is in its first position wherein, when lever 1010 is rotated in its first direction, first cam portion 1025 can be rotated out of retention slot 939. As cam 1020 is moved into its second position, second cam portion 1027 can be positioned over, but not positioned within, retention slot 939. In at least one embodiment, second cam portion 1027 may be positioned within retention slot 939 but may not be able to hold swing arm 931 in position.

In various embodiments, swing arm 931 can be rotatably mounted to frame 904 such that, when cam 1020 is sufficiently disengaged from retention slot 939, swing arm 931 can be pivoted in order to move pinion gear 910 away from and out of engagement with drive shaft 900 and/or drive gear 908. In at least one embodiment, referring to FIGS. 63, 65, and 67, proximal end 933 of swing arm 931 can be pivotably mounted to frame 904 via a hinge 935. In use, as outlined above, swing arm 931 can be held in its first position by cam 1020 until lever 1010 is utilized to disengage cam 1020 from swing arm 931 such that swing arm 931 can be moved into a second position. In at least one embodiment, referring to FIG. 34, manual return mechanism 1000 can further include at least one spring, such as spring 920, for example, which can be configured to bias swing arm 931 into its second position. Spring 920 can be configured such that it is compressed intermediate swing arm 931 and frame 904, for example, when swing arm 931 is in its first position, wherein spring 920 can be permitted to expand and move swing arm 931 into its second position when cam 1020 is moved into its second position. In at least one embodiment, the range of motion of swing arm 931 can be confined. In some embodiments, the proximal end 933 of swing arm 931 can further include one or more stop surfaces, such as stop surface 937, for example, which can be configured to engage frame 904, for example, in order to limit the range of motion of swing arm 931. In any event, once swing arm 931 has been moved into its second position, pinion gear 910 may no longer be operably engaged with drive gear 908 and/or first teeth 918 of drive shaft 900. In such circumstances, the rotation of drive gear 908 by motor 902 may not be transmitted to drive shaft 900 and the retraction of drive shaft 900 by lever 1010 and pawl 1032 may be performed without interference, or at least substantial interference, from motor 902.

In various embodiments, further to the above, the movement of lever 1010 in its first direction can both engage manual return mechanism 1000 with drive shaft 900 and operably disengage motor 902 from drive shaft 900. After being moved in its first direction, lever 1010 can be rotated in a second direction to return lever 1010 to its starting position wherein, similar to the above, lever 1010 can be rotated away from cam 1020 such that cam 1020 is left in its second position. At such point, lever 1010 can be repeatedly ratcheted in its first and second directions in order to suitably retract drive shaft 900. In at least one embodiment, manual return mechanism 1000 can be configured such that a surgeon, or another operator of the instrument, is not afforded the opportunity to reset the instrument and, as a result, motor 902 cannot be utilized once again to move drive shaft 900. In at least one other embodiment, manual return mechanism 1000 can be reset by pushing swing arm 1031 back into its first position and rotating cam 1020 into its first position such that first cam portion 1025 is engaged with retention slot 939 once again.

Figure 56:
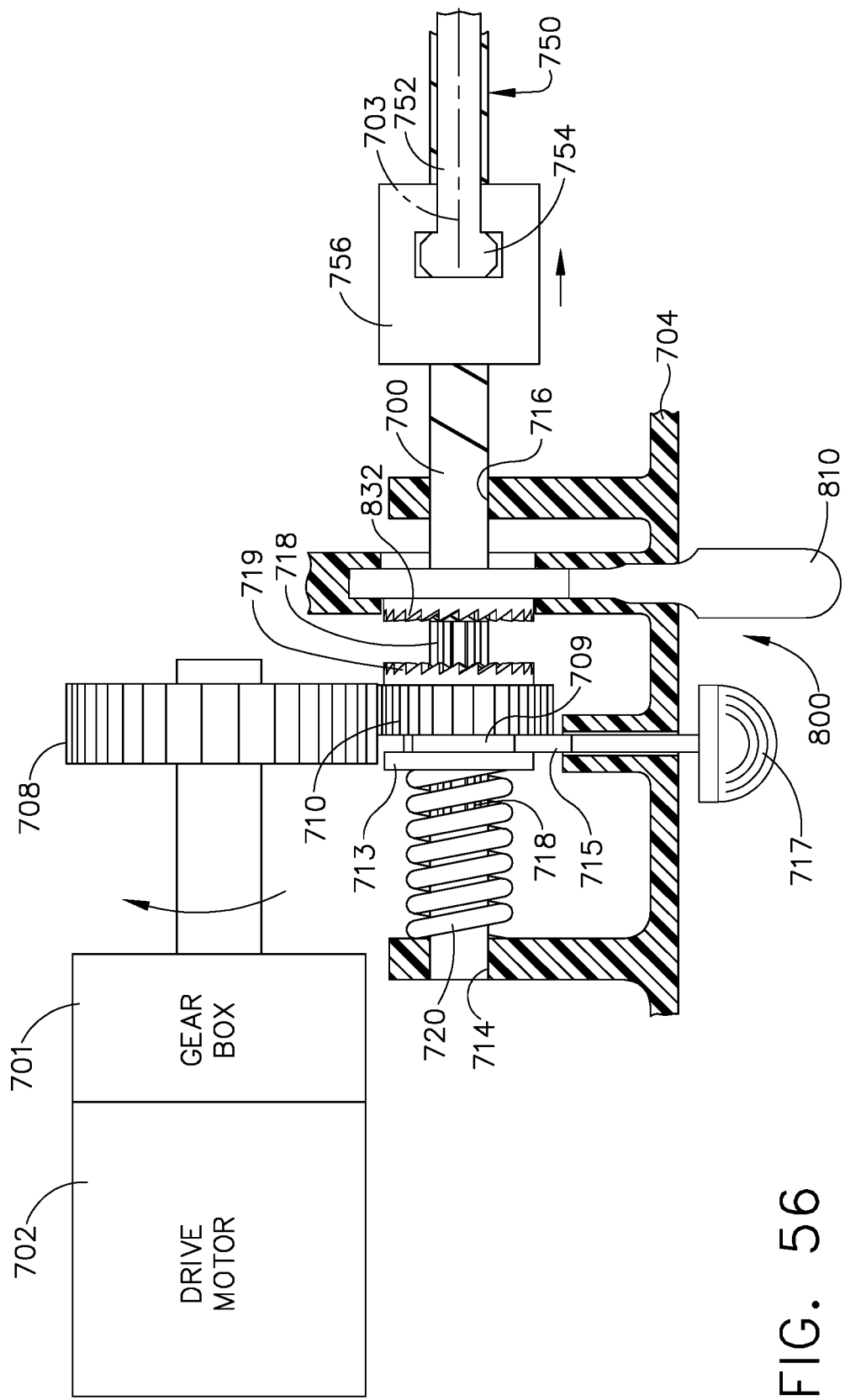
FIG. 56 is a diagram of a rotatable drive shaft and a manual return mechanism of a surgical cutting and fastening instrument according to various embodiments of the present invention, the diagram illustrating a pinion gear operably engaged with a gear box and a motor via a drive gear.
Figure 57:
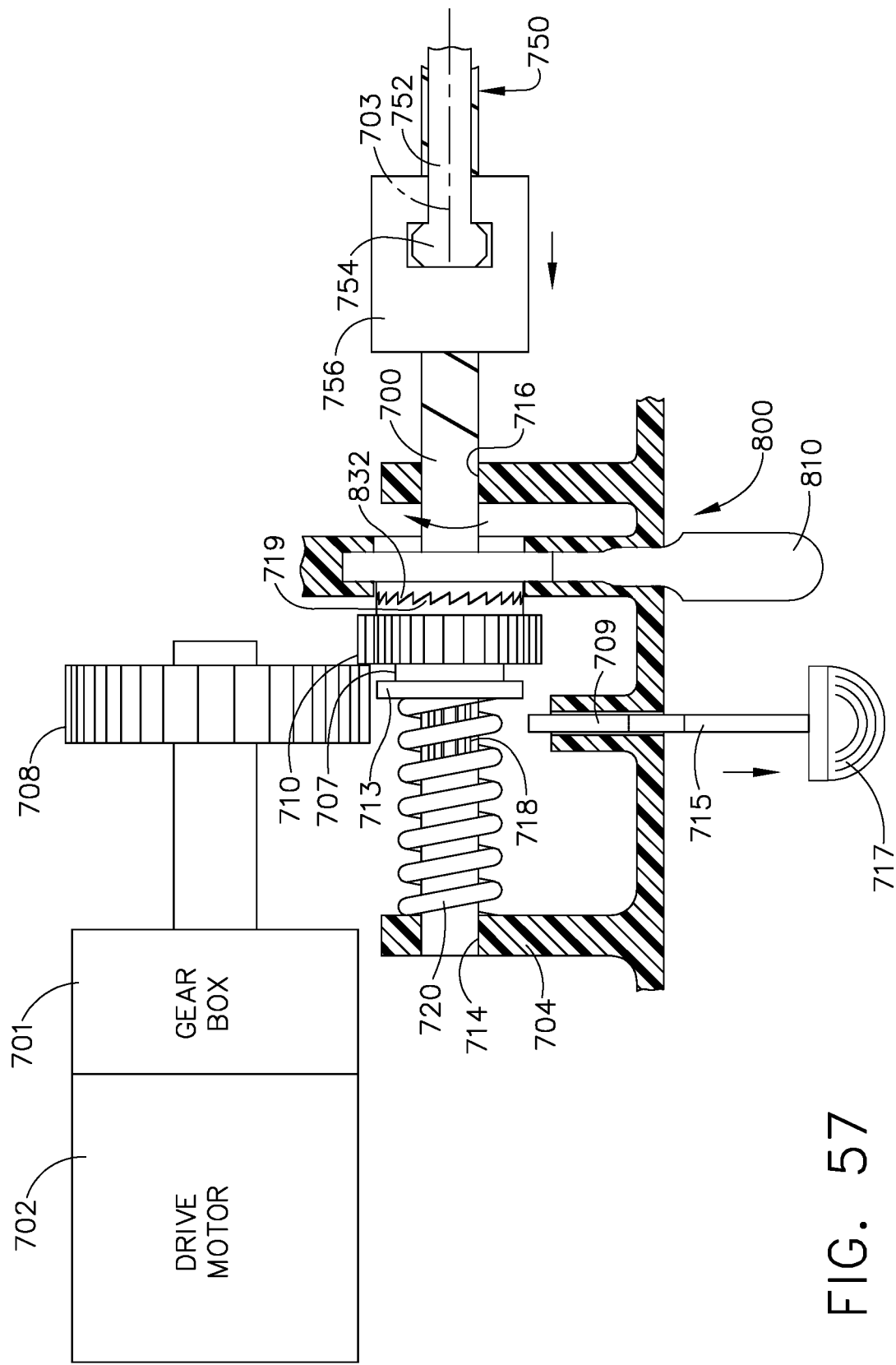
FIG. 57 is a diagram of the manual return mechanism of FIG. 56 illustrating a yoke disengaged from the pinion gear in order to allow a pinion gear spring to bias the pinion gear into engagement with a lever of the manual return mechanism and, in addition, bias the pinion gear out of engagement with the drive gear, the diagram further illustrating the lever in a starting position.
Figure 58:
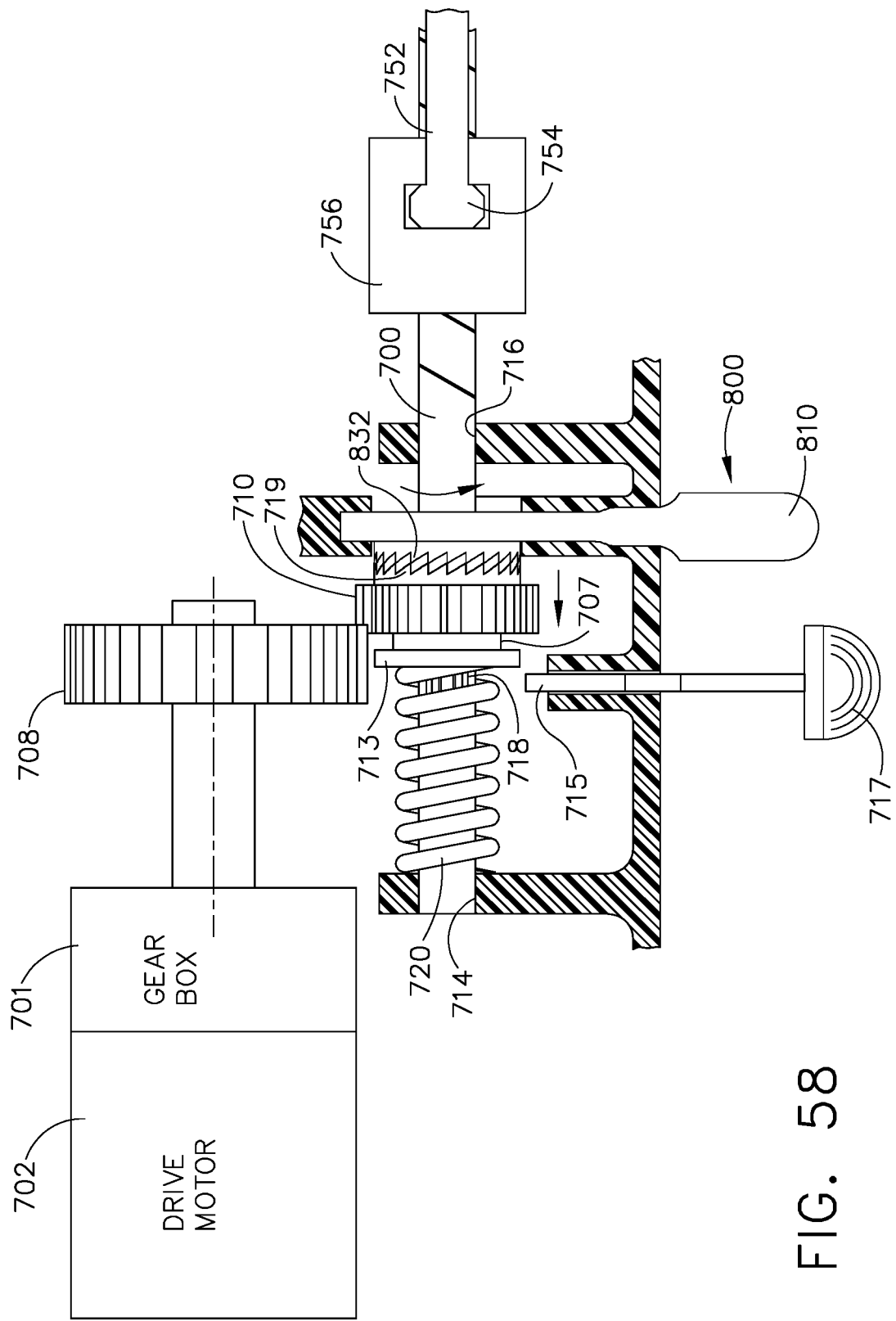
FIG. 58 is a diagram of the manual return mechanism of FIG. 56 illustrating the lever being ratcheted back into its starting position and the pinion gear partially engaged with the drive gear.

In various embodiments, referring to FIGS. 56-58, a surgical instrument can include a rotatable drive shaft and a manual return mechanism configured to rotate the drive shaft. In at least one embodiment, referring to FIG. 56, rotatable drive shaft 700 can be rotatably supported in apertures 714 and 716 of frame 704, for example. In certain embodiments, the surgical instrument can further include a drive system configured to rotate drive shaft 700, wherein the drive system can comprise a drive gear 708, a motor 702 for rotating drive gear 708, and a gear box 701 which can be configured to provide a gear reduction and/or otherwise allow motor 702 and drive gear 708 to rotate at different speeds. The surgical instrument can further include a pinion gear 710 which, when positioned in a first position as illustrated in FIG. 56, can be configured to transmit the rotational motion of drive gear 708 to drive shaft 700. In various embodiments, drive shaft 700 can include a spline portion 718 which can comprise one or more projections and/or one or more recesses which can be closely received by the sidewalls of an aperture (not illustrated) extending through pinion gear 710. In at least one such embodiment, the perimeter of the pinion gear aperture can be configured such that it matches, or at least substantially matches, the perimeter of spline portion 718. Owing to the co-operating features of the pinion gear aperture and spline portion 718, motor 702 can be operably engaged with drive shaft 700 such that the rotational motion of drive gear 708 can be transmitted to drive shaft 700. When drive shaft 700 is rotated in a first direction, drive shaft 700 can be configured to advance drive nut 756, and knife bar assembly 750 attached thereto, along drive shaft 700. More particularly, in at least one embodiment, the outer surface of drive shaft 700 can comprise a helical drive thread which, when rotated relative to drive nut 756, can be configured to convert the rotational movement of drive shaft 700 to the translational movement of drive nut 756 such that drive nut 756 is advanced along shaft axis 703. Correspondingly, when drive shaft 700 is rotated in an opposite direction, the helical thread can retract drive nut 756. As illustrated in FIG. 56, the proximal end 754 of knife bar 752 can be attached to and/or otherwise suitably engaged with drive nut 756 such that, when drive nut 756 is advanced distally and/or retracted proximally by drive shaft 700, knife bar 752 can be moved along with drive nut 756 in order to move a cutting member and/or staple sled associated therewith within an end effector.

Figure 59:
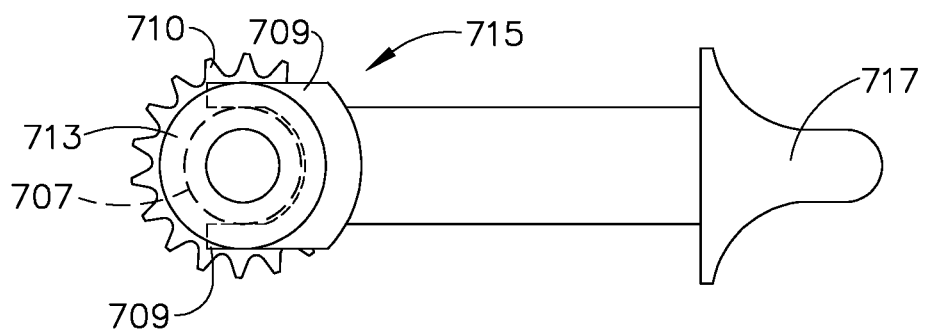
FIG. 59 is an end view of the yoke and pinion gear of FIG. 57.

In use, as outlined above, motor 702 can rotate drive shaft 700 in a first direction in order to advance knife bar assembly 750 and, in addition, rotate drive shaft 700 in a second direction in order to retract knife bar assembly 750. In the event, however, that motor 702 becomes inoperable and/or knife bar assembly 750 becomes stuck, for example, manual retraction mechanism 800 can be operably engaged with drive shaft 700 in order to rotate drive shaft 700 in its second, or retraction, direction. In various embodiments, referring to FIGS. 56 and 57, a surgeon, or another operator of the instrument, can pull yoke 715 out of engagement with pinion gear 710 such that pinion gear 710 can be displaced, or slid, between its first position in which it is engaged with drive gear 708 and spline portion 718 and a second position in which it is engaged with spline portion 718 and lever 810. In at least one embodiment, pinion gear 710 can be moved from its first position, as illustrated in FIG. 56, into its second position, as illustrated in FIG. 57, by spring 718 after yoke 715 has been disengaged from collar 713 of pinion gear 710. In certain embodiments, referring now to FIG. 59, yoke 715 can include handle 717 which can be configured to be grasped by the surgeon such that one or more projections, or tines, 709 extending from yoke 715 can be disengaged from recess 707 defined within collar 713. In any event, once pinion gear 710 has been moved into its second position, as illustrated in FIG. 57, pinion gear 710 can be operably engaged with retraction lever 810. In certain embodiments, spring 710 can bias pinion gear 710 against retraction lever 710 such that ratchet face 719 on pinion gear 710 is operably engaged with ratchet face 832 on lever 810.

In various embodiments, further to the above, pinion gear 710 can be moved out of engagement with drive gear 708 at the same time as pinion gear 710 is moved into engagement with lever 810. In certain embodiments, pinion gear 710 can be moved out of engagement with drive gear 708 before pinion gear 710 is moved into engagement with lever 810. In any event, in at least one embodiment, the rotation of lever 810 can be transmitted to pinion gear 710 via the co-operating ratchet teeth on ratchet faces 719 and 832, wherein the rotation of pinion gear 710 can be transmitted to drive shaft 700 via spline portion 712. In certain embodiments, only one rotation, or less than one rotation, of lever 810 may be required to sufficiently retract drive shaft 700 although, in other embodiments, more than one rotation of lever 810 may be required. In various embodiments, referring to FIG. 58, the ratchet faces of lever 810 and pinion gear 710 can be configured to allow lever 810 to be rotated in a second direction, i.e., a direction opposite the first direction, in order to return lever 810 to its starting position such that lever 810 can be rotated in its first direction once again. In at least one embodiment, pinion gear 710 and/or drive shaft 700 can be held in position while lever 810 is ratcheted back into its starting position, for example, so as to prevent, or at least inhibit, drive shaft 700 from simply moving back and forth with lever 810. In at least one such embodiment, referring to FIG. 58, the rotation of lever 810 in its second direction can displace pinion gear 710 into at least partial engagement with drive gear 708 such that drive gear 708, gear box 701, and motor 702 can hold pinion gear 710 in position while lever 810 is rotated in its second direction. In certain embodiments, the gear ratios between pinion gear 710 and drive gear 708, and/or within gear box 701, can be such that the rotation of pinion gear 710 is prevented, or at least inhibited, absent the application of a significant mechanical advantage and/or force to lever 810, which may not occur under most circumstances.

In various embodiments, further to the above, the lever 810 can be ratcheted in its first and second directions as many times as needed in order to rotate drive shaft 700 in its second direction such that knife assembly 750 is sufficiently retracted. In at least one embodiment, manual retraction mechanism 800 can be configured such that pinion gear 710 cannot be returned to its first position after being moved into its second position. In such embodiments, motor 702 cannot be used to rotate drive shaft 900 once again. In certain other embodiments, pinion gear 710 can be returned to its first position and yoke 715 can be re-engaged with collar 713 such that pinion gear 710 can be held in operative engagement with drive gear 708 and, correspondingly, motor 702.

Figure 60:
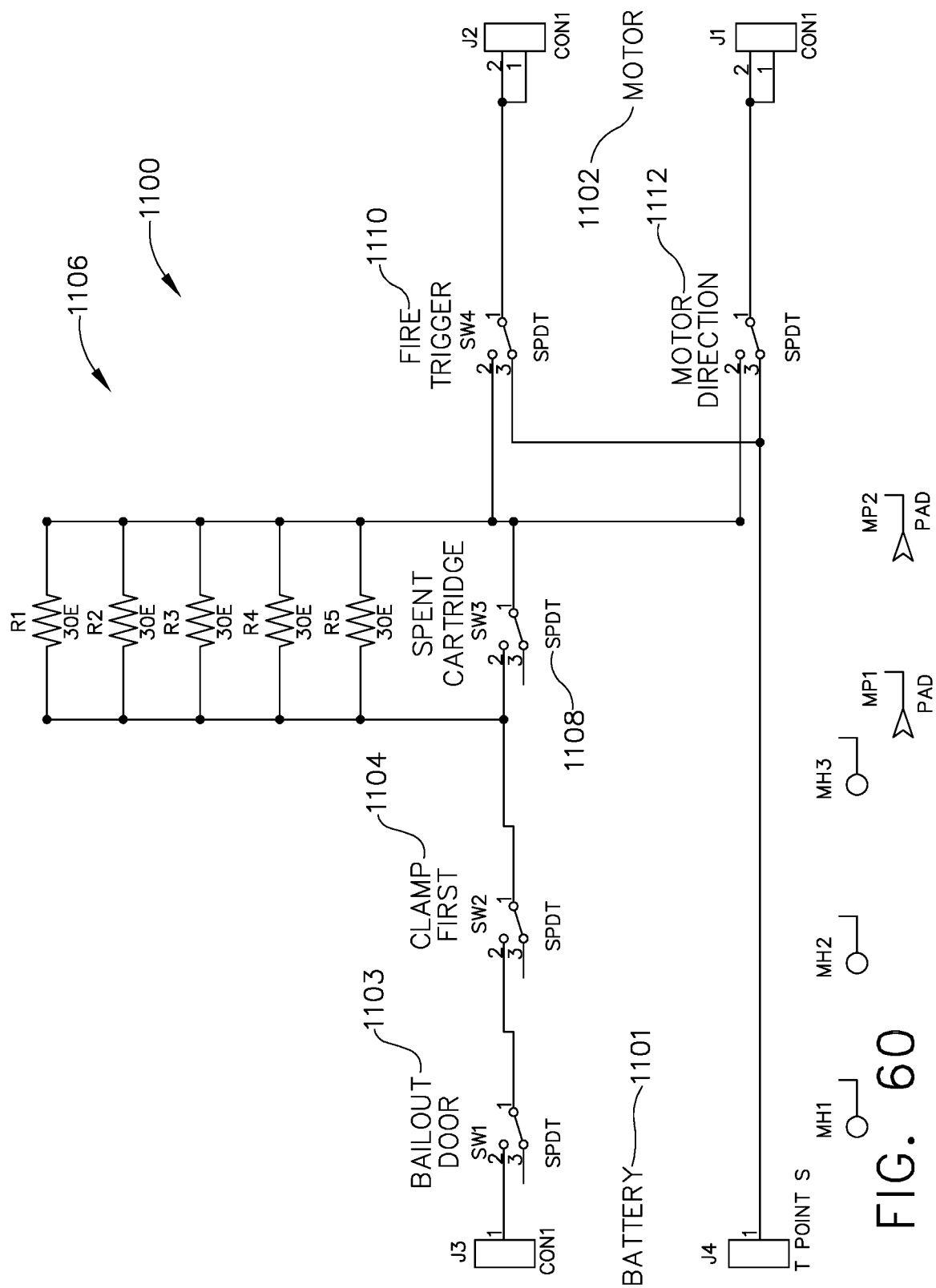
FIG. 60 is a schematic diagram of a circuit including a switch configured to be actuated by the lever of the manual retraction mechanism of FIG. 56, wherein the actuation of the switch operably disengages the motor.

In various embodiments, as described above, the operation, or actuation, of a manual retraction lever can operably disengage a motor from a drive shaft such that the motor does not resist or impede the movement of the manual retraction lever. In several such embodiments, the operation of the retraction lever can mechanically decouple the motor from the drive shaft. Such embodiments may provide an advantage in that, even if the motor continues to rotate, the rotation of the motor cannot be transmitted to the drive shaft. In certain embodiments, the operation of a manual retraction lever can electrically decouple the motor from a power source. Such embodiments may provide an advantage in that the motor cannot rotate without power from the battery regardless of whether the motor and the drive shaft have been mechanically decoupled. In some embodiments, the operation of a manual retraction lever can cause the actuation of an electro-mechanical device, such as a solenoid, for example, which can electrically decouple, mechanically decouple, and/or lock a drive shaft in position. In various embodiments, a manual retraction system can include a mechanical decoupling arrangement, an electrical decoupling arrangement, and/or an electro-mechanical decoupling arrangement. In at least one embodiment, referring to circuit 1100 illustrated in FIG. 60, a surgical instrument can include a battery 1101, a motor 1102, and one or more switches, such as bail-out, or manual return, lever switch 1103, for example, which can be configured to electrically couple/decouple battery 1101 and motor 1102. In various embodiments, switch 1103 can comprise a single pole—single throw switch, and/or any other suitable switch, wherein the operation of a bail-out, or manual return lever, such as lever 810, for example, can open the switch 1103 and electrically decouple battery 1101 from motor 1102. In certain embodiments, switch 1103 can comprise a single pole—double throw switch as illustrated in FIG. 60. In at least one such embodiment, the operation of the manual return lever can manipulate the switch 1103 between a first condition in which contacts 1 and 2 are in electrical communication with one another such that current can flow to motor 1102 and a second condition in which contact 1 is connected to contact 3 (which may be grounded) and, as a result, current cannot flow from battery 1101 to motor 1102. In various embodiments, the initial operation of the manual return lever can manipulate switch 1103 between its first and second conditions, wherein, in at least one embodiment, switch 1103 cannot be closed, or reset, after it has been opened and, as a result, motor 1102 cannot be used to move the drive shaft of the surgical instrument once again. In other embodiments, however, switch 1103 can be reset, or closed, and power can be supplied to motor 1102 from battery 1101 once again. In at least one such embodiment, although not illustrated, the drive shaft, and/or a knife assembly engaged with the drive shaft, can reset the switch after it has been retracted a sufficient distance. Although mechanical switches can be utilized in various embodiments, solid state or electromechanical switches, a processor-based controller, and sensor systems can be utilized to detect the movement of the manual retraction lever.

Referring once again to circuit 1100, although only one manual return lever switch 1103 is illustrated in FIG. 60, two or more switches can be utilized. In at least one such embodiment, although not illustrated, such switches can provide for a redundant system. In various embodiments, circuit 1100 can further include a clamp switch 1104 which can be configured to detect whether the anvil of an end effector has been closed. More particularly, in at least one embodiment, switch 1104 can be configured such that it is in a normally-open condition wherein current cannot flow to motor 1162 unless switch 1104 has been closed by the anvil. In various embodiments, circuit 1100 can further include a switch arrangement 1106 which can be utilized to detect (i) whether a staple cartridge positioned within an end effector has been previously-used and/or (ii) information regarding the position of a cutting member within the end effector. In at least one embodiment, switch arrangement 1106 can include a spent cartridge switch 1108 which is in a normally-closed condition, i.e., until the staple cartridge has been at least partially expended after which switch 1108 can be in a normally-open condition. In certain embodiments, switch 1108 can be opened by a cutting member when it reaches the end of its stroke within an end effector. When spent cartridge switch 1108 is in a closed condition, most of the current can flow directly from clamp switch 1104 to fire trigger switch 1110 through the low-resistance conduction path of the switch 1108, for example. When spent cartridge switch 1108 is in an open condition, the battery current flows through a network comprising parallel-connected resistors R1, R2, R3, R4, and R5, for example. The resistance of the resistor network may be sufficiently high to substantially lower the current flowing to motor 1102. In such circumstances, the lowered current can be insufficient to operate motor 1102 but can still provide a sufficient current which can be detected. In various embodiments, the lowered current can be evaluated by a microprocessor (not illustrated) to determine the current level through the various resistors and, in view of such information and/or other provided information, determine which type of staple cartridge is present in the end effector. Various embodiments are disclosed in commonly-owned, U.S. patent application Ser. No. 12/235,782, entitled MOTOR-DRIVEN SURGICAL CUTTING INSTRUMENT, which was filed on Sep. 23, 2008, now U.S. Pat. No. 8,210,411, the entire disclosure of which is hereby incorporated by reference herein.

In various embodiments, further to the above, circuit 1100 can further include a firing trigger switch 1110 which can be switched from a normally-open condition to a closed condition when a firing trigger is actuated to fire, or deploy, the staples. In at least one embodiment, such a firing trigger can comprise a lever, which can be squeezed by the surgeon, and/or any other suitable trigger, such as a push-button trigger, for example. In any event, contacts 1 and 2 of switch 1110 can be placed in electrical communication with one another when the firing trigger is actuated such that the current can flow though motor 1102. In certain embodiments, though, circuit 1100 can further include motor direction switch 1112 which can be configured to change the polarity of the voltage applied to motor 1102 and, as a result, change the direction in which motor 1102 is rotated. As illustrated in FIG. 60, contacts 1 and 3 of motor direction switch 1112 can be in electrical communication with one another to cause motor 1102 to rotate in such a direction so as to advance a cutting member and/or staple sled within an end effector. In order to retract the cutting member and/or staple sled, motor direction switch 1112 can be reconfigured such that contacts 1 and 2 are in electrical communication with one another and the polarity of the voltage applied to motor 1102 can be reversed.

The various embodiments of the present invention have been described above in connection with cutting-type surgical instruments. It should be noted, however, that in other embodiments, the inventive surgical instrument disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc. Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Furthermore, the present invention has been discussed in terms of endoscopic procedures and apparatuses. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

Further to the above, the various staple cartridges disclosed herein can be disposable. In at least one embodiment, an expended staple cartridge, or an at least partially expended staple cartridge, can be removed from a surgical stapler and replaced with another staple cartridge. In other various embodiments, the staple cartridge may not be removable and/or replaceable during the ordinary use of the surgical instrument but, in some circumstances, may be replaceable while and/or after the surgical stapler is reconditioned as described in greater detail below. In various embodiments, the staple cartridge can be part of a disposable loading unit or end-effector which can further include a staple cartridge carrier, anvil, cutting member, and/or staple driver. In at least one such embodiment, the entire, or at least a portion of, the disposable loading unit or end-effector can be detachably connected to a surgical instrument and can be configured to be replaced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

What is claimed is:

1. An apparatus, comprising:
   (a) an end effector comprising:
      (i) a first jaw,
      (ii) a second jaw configured to cooperate with the first jaw to clamp and staple tissue with a plurality of staples, and
      (iii) a firing driver actuatable through a firing stroke to eject the staples into the clamped tissue;
   (b) a motor operable to actuate the firing driver through the firing stroke; and
   (c) a manual actuator, wherein the manual actuator is selectively movable by a user to mechanically decouple the motor from the firing driver and manually actuate the firing driver.

2. The apparatus of claim 1, wherein the manual actuator is operable to retract the firing driver after the firing driver has completed at least a portion of the firing stroke.

3. The apparatus of claim 1, wherein the manual actuator is movable to permit mechanical recoupling of the motor with the firing driver after the motor has been mechanically decoupled from the firing driver.

4. The apparatus of claim 1, further comprising a drive shaft operatively coupled with the firing driver.

5. The apparatus of claim 4, wherein the manual actuator is movable relative to the drive shaft from a disengaged position to an engaged position to mechanically decouple the motor from the firing driver, wherein the manual actuator in the engaged position is actuatable by a user to manually actuate the firing driver, wherein the manual actuator is movable from the engaged position to the disengaged position to permit mechanical recoupling of the motor with the firing driver.

6. The apparatus of claim 5, further comprising:
   (a) a motor gear operatively associated with the motor;
   (b) a manual actuator gear operatively associated with the manual actuator; and
   (c) a drive shaft gear operatively associated with the drive shaft;
   wherein the motor gear is configured to engage the drive shaft gear and thereby drive the drive shaft when the manual actuator is in the disengaged position, wherein the manual actuator gear is configured to engage the drive shaft gear and thereby drive the drive shaft when the manual actuator is in the engaged position.

7. The apparatus of claim 6, wherein the motor gear is translatable relative to the drive shaft gear between a coupled position in which the motor gear is coupled with the drive shaft gear, and a decoupled position in which the motor gear is decoupled from the drive shaft gear, wherein the motor gear is configured to assume the decoupled position when the manual actuator is in the engaged position.

8. The apparatus of claim 7, wherein the motor gear is rotatable about a first axis and translatable along a second axis perpendicular to the first axis between the coupled position and the decoupled position.

9. The apparatus of claim 7, wherein the manual actuator includes a protrusion configured to directly contact and translatably drive the motor gear from the coupled position to the decoupled position when the manual actuator is moved from the disengaged position to the engaged position.

10. The apparatus of claim 7, further comprising a lock configured to releasably retain the motor gear in the decoupled position when the manual actuator is in the engaged position.

11. The apparatus of claim 10, wherein the motor gear is resiliently biased toward the coupled position, wherein the lock is selectively actuatable by a user to release the motor gear from the decoupled position such that the motor gear resumes the coupled position and simultaneously drives the manual actuator from the engaged position to the disengaged position.

12. An apparatus, comprising:
   (a) an end effector comprising:
      (i) a first jaw,
      (ii) a second jaw configured to cooperate with the first jaw to clamp and staple tissue with a plurality of staples, and
      (iii) a firing driver actuatable through a firing stroke to eject the staples into the clamped tissue;
   (b) a motor operable to actuate the firing driver through the firing stroke; and
   (c) a manual actuator, wherein the manual actuator is movable from a disengaged position to an engaged position to mechanically decouple the motor from the firing driver, wherein the manual actuator in the engaged position is actuatable by a user to manually actuate the firing driver, wherein the manual actuator is movable from the engaged position to the disengaged position to permit mechanical recoupling of the motor with the firing driver.

13. The apparatus of claim 12, further comprising a drive shaft operatively coupled with the firing driver, wherein the manual actuator in the disengaged position is operatively disengaged from the drive shaft, wherein the manual actuator in the engaged position is operatively engaged with the drive shaft.

14. The apparatus of claim 13, further comprising:
(a) a motor gear assembly operatively associated with the motor;
(b) a manual actuator gear assembly operatively associated with the manual actuator; and
(c) a drive shaft gear assembly operatively associated with the drive shaft;
wherein the motor gear assembly is configured to engage the drive shaft gear assembly and thereby drive the drive shaft when the manual actuator is in the disengaged position, wherein the manual actuator gear assembly is configured to engage the drive shaft gear assembly and thereby drive the drive shaft when the manual actuator is in the engaged position.

15. The apparatus of claim 14, wherein the motor gear assembly comprises a first crown gear, the manual actuator gear assembly comprises a second crown gear, and the drive shaft gear assembly comprises a pair of third crown gear configured to engage the first and second crown gears.

16. The apparatus of claim 14, wherein the motor gear assembly is translatable relative to the drive shaft gear assembly between a coupled position in which the motor gear assembly is coupled with the drive shaft gear assembly, and decoupled position in which the motor gear assembly is decoupled from the drive shaft gear assembly, wherein the motor gear assembly is configured to assume the decoupled position when the manual actuator is in the engaged position.

17. The apparatus of claim 16, wherein the motor gear assembly is resiliently biased toward the coupled position.

18. The apparatus of claim 17, further comprising a lock configured to releasably retain the motor gear assembly in the decoupled position when the manual actuator is in the engaged position, wherein the lock is selectively actuatable by a user to release the motor gear assembly from the decoupled position.

19. An apparatus, comprising:
(a) an end effector comprising:
(i) a first jaw,
(ii) a second jaw configured to cooperate with the first jaw to clamp and staple tissue with a plurality of staples, and
(iii) a firing driver actuatable through a firing stroke to eject the staples into the clamped tissue;
(b) a drive shaft operatively coupled with the firing driver;
(c) a motor;
(d) a motor gear translatable relative to the drive shaft between a coupled position and a decoupled position, wherein in the coupled position the motor is operatively coupled with the drive shaft such that the motor is configured to drive the firing driver through the firing stroke, wherein in the decoupled position the motor is operatively decoupled from the drive shaft such that the motor is incapable of driving the firing driver; and
(e) a manual actuator, wherein the manual actuator is selectively movable relative to the drive shaft from a disengaged position to an engaged position to translatably drive the motor gear from the coupled position to the decoupled position, wherein the manual actuator in the engaged position is actuatable by a user to manually actuate the firing driver.

20. The apparatus of claim 19, wherein the manual actuator is translatable relative to the drive shaft between the disengaged position and the engaged position, wherein the motor gear is resiliently biased toward the coupled position and is configured to translatably drive the manual actuator from the engaged position to the disengaged position in response to a user input.

* * * * *